(12) United States Patent
Podack et al.

(10) Patent No.: US 8,968,720 B2
(45) Date of Patent: Mar. 3, 2015

(54) HEAT SHOCK PROTEIN GP96 VACCINATION AND METHODS OF USING SAME

(75) Inventors: Eckhard R. Podack, Coconut Grove, FL (US); Joseph R. Rosenblatt, Hollywood, FL (US)

(73) Assignee: University of Miami, Miami, FL (US)

( * ) Notice: Subject to any disclaimer, the term of this patent is extended or adjusted under 35 U.S.C. 154(b) by 302 days.

(21) Appl. No.: 12/933,567

(22) PCT Filed: Mar. 19, 2009

(86) PCT No.: PCT/US2009/001727
§ 371 (c)(1),
(2), (4) Date: Mar. 21, 2011

(87) PCT Pub. No.: WO2009/117116
PCT Pub. Date: Sep. 24, 2009

(65) Prior Publication Data
US 2011/0171211 A1  Jul. 14, 2011

Related U.S. Application Data

(60) Provisional application No. 61/038,313, filed on Mar. 20, 2008.

(51) Int. Cl.
*A01N 63/00* (2006.01)
*A61K 39/395* (2006.01)
*C12N 15/63* (2006.01)
*A61K 38/17* (2006.01)
*A61K 39/00* (2006.01)
*C07K 16/28* (2006.01)
*C12N 5/16* (2006.01)
*A61K 35/12* (2006.01)

(52) U.S. Cl.
CPC .............. *A61K 38/1709* (2013.01); *C12N 5/16* (2013.01); *A61K 39/395* (2013.01); *C12N 15/63* (2013.01); *A61K 35/12* (2013.01); *A61K 39/0011* (2013.01); *A61K 2039/505* (2013.01); *A61K 2039/5152* (2013.01); *A61K 2039/5156* (2013.01); *A61K 2039/6043* (2013.01); *C07K 16/2887* (2013.01)
USPC .................. 424/93.21; 424/155.1; 424/174.1; 435/455

(58) Field of Classification Search
CPC ........ C12N 5/16; C12N 15/63; A61K 39/395; A61K 39/0011; A61K 38/1709; A61K 2039/5152; A61K 2039/6043
USPC .................. 424/93.21, 155.1, 174.1; 435/455
See application file for complete search history.

(56) References Cited

U.S. PATENT DOCUMENTS

| | | |
|---|---|---|
| 4,215,051 A | 7/1980 | Schroeder et al. |
| 4,690,915 A | 9/1987 | Rosenberg |
| 5,108,921 A | 4/1992 | Low et al. |
| 5,137,819 A | 8/1992 | Kilburn |
| 5,168,062 A | 12/1992 | Stinski |
| 5,188,964 A | 2/1993 | McGuire |
| 5,202,247 A | 4/1993 | Kilburn |
| 5,217,891 A | 6/1993 | Brake |
| 5,232,833 A | 8/1993 | Sanders |
| 5,284,656 A | 2/1994 | Platz et al. |
| 5,348,945 A | 9/1994 | Berberian |
| 5,385,839 A | 1/1995 | Stinski |
| 5,399,346 A | 3/1995 | Anderson |
| 5,444,087 A | 8/1995 | Patel |
| 5,451,569 A | 9/1995 | Wong et al. |
| 5,496,934 A | 3/1996 | Shoseyov |
| 5,580,859 A | 12/1996 | Felgner |
| 5,719,044 A | 2/1998 | Shoseyov |
| 5,747,332 A | 5/1998 | Wallen |
| 5,750,119 A | 5/1998 | Srivastava |
| 5,830,464 A | 11/1998 | Srivastava |
| 5,837,251 A | 11/1998 | Srivastava |
| 5,948,646 A | 9/1999 | Srivastava |
| 5,961,979 A | 10/1999 | Srivastava |
| 5,985,270 A | 11/1999 | Srivastava |
| 5,997,873 A | 12/1999 | Srivastava |
| 6,007,821 A | 12/1999 | Srivastava |
| 6,017,540 A | 1/2000 | Srivastava |
| 6,017,544 A | 1/2000 | Srivastava |
| 6,030,618 A | 2/2000 | Srivastava |
| 6,048,530 A | 4/2000 | Srivastava et al. |
| 6,051,424 A | 4/2000 | Kato et al. |
| 6,130,087 A | 10/2000 | Srivastava |
| 6,136,315 A | 10/2000 | Srivastava |

(Continued)

FOREIGN PATENT DOCUMENTS

| | | |
|---|---|---|
| CA | 2158655 | 9/1994 |
| CN | 101057975 | 10/2009 |

(Continued)

OTHER PUBLICATIONS

McCluskie et al., 1999, Molecular Medicine, vol. 5, p. 287-300.*
Tollefsen et al., 2003, Scandinavian Journal of Immunology, vol. 57, p. 229-238.*
Arnold, D. et al., "Influences of Transporter Associated with Antigen Processing (TAP) on the Repertoire of Peptides Associated with the Endoplasmic Reticulum-resident Stress Protein gp96," J. Exp. Med., 1997, vol. 186, No. 3:461-466.
Ausubel, et al., "Current Protocols in Molecular Biology," 1988, vol. 3, Chapter 13, published by Wiley, John & Sons, Incorporated (Abstract).

(Continued)

*Primary Examiner* — Shin Lin Chen
(74) *Attorney, Agent, or Firm* — Fish & Richardson P.C.

(57) ABSTRACT

The invention provides a tumor cell genetically modified to express a nucleic acid encoding a secreted form of a heat shock protein (hsp) gp96 polypeptide. The invention also provides a method of stimulating an immune response to a tumor by administering a tumor cell genetically modified to express a nucleic acid encoding a secreted form of a gp96 polypeptide.

12 Claims, 20 Drawing Sheets

(56) References Cited

U.S. PATENT DOCUMENTS

| | | | |
|---|---|---|---|
| 6,156,302 | A | 12/2000 | Srivastava |
| 6,162,436 | A | 12/2000 | Srivastava |
| 6,168,793 | B1 | 1/2001 | Srivastava |
| 6,322,790 | B1 | 11/2001 | Srivastava |
| 6,328,957 | B1 | 12/2001 | Colston |
| 6,331,299 | B1 | 12/2001 | Rothman |
| 6,383,493 | B1 | 5/2002 | Srivastava |
| 6,383,494 | B1 | 5/2002 | Srivastava |
| 6,387,374 | B1 | 5/2002 | Srivastava |
| 6,399,070 | B1 | 6/2002 | Srivastava |
| 6,403,095 | B1 | 6/2002 | Srivastava |
| 6,406,700 | B1 | 6/2002 | Srivastava |
| 6,410,026 | B1 | 6/2002 | Srivastava |
| 6,410,027 | B1 | 6/2002 | Srivastava |
| 6,410,028 | B1 | 6/2002 | Srivastava |
| 6,436,404 | B1 | 8/2002 | Srivastava |
| 6,447,780 | B1 | 9/2002 | Srivastava |
| 6,447,781 | B1 | 9/2002 | Srivastava |
| 6,451,316 | B1 | 9/2002 | Srivastava |
| 6,455,048 | B1 | 9/2002 | Srivastava |
| 6,455,503 | B1 | 9/2002 | Srivastava |
| 6,461,615 | B1 | 10/2002 | Srivastava |
| 6,468,540 | B1 | 10/2002 | Srivastava |
| 6,475,490 | B1 | 11/2002 | Srivastava |
| 6,605,464 | B1 | 8/2003 | Rothman |
| 6,610,659 | B1 | 8/2003 | Pramod |
| 6,641,812 | B2 | 11/2003 | Rothman |
| 6,651,655 | B1 | 11/2003 | Licalsi et al. |
| 6,656,679 | B2 | 12/2003 | Rothman |
| 6,663,868 | B1 | 12/2003 | Rothman |
| 6,673,348 | B2 | 1/2004 | Rothman |
| 6,719,974 | B1 | 4/2004 | Rothman |
| 6,761,892 | B1 | 7/2004 | Rothman |
| 6,797,480 | B1 | 9/2004 | Srivastava |
| 6,797,491 | B2 | 9/2004 | Neefe et al. |
| 7,132,109 | B1 | 11/2006 | Srivastava |
| 7,601,359 | B1 | 10/2009 | Srivastava |
| 8,475,785 | B2 | 7/2013 | Podack et al. |
| 8,685,384 | B2 | 4/2014 | Podack et al. |
| 2003/0133930 | A1 | 7/2003 | Goldenberg |
| 2003/0170756 | A1 | 9/2003 | Berd |
| 2004/0052812 | A1 | 3/2004 | Hoe et al. |
| 2005/0019752 | A1 | 1/2005 | Franchini |
| 2007/0141666 | A1 | 6/2007 | Dupraz et al. |
| 2008/0019972 | A1 | 1/2008 | Andrieu |
| 2008/0026012 | A1 | 1/2008 | Podack |
| 2008/0089901 | A1 | 4/2008 | Hanke |
| 2009/0148471 | A1 | 6/2009 | Wu et al. |
| 2009/0162404 | A1* | 6/2009 | Podack |
| 2011/0223196 | A1 | 9/2011 | Podack |
| 2011/0250229 | A1 | 10/2011 | Podack |
| 2011/0287057 | A1 | 11/2011 | Podack |
| 2013/0302376 | A1 | 11/2013 | Podack et al. |
| 2014/0037682 | A1 | 2/2014 | Podak et al. |
| 2014/0286991 | A1 | 9/2014 | Podack et al. |

FOREIGN PATENT DOCUMENTS

| | | |
|---|---|---|
| CN | 102223894 | 10/2011 |
| GB | 2251186 | 7/1992 |
| JP | 2002-506005 | 2/2002 |
| JP | 2007-532681 | 11/2007 |
| WO | 8912455 | 12/1989 |
| WO | 9002564 | 3/1990 |
| WO | 9102077 | 2/1991 |
| WO | 9115572 | 10/1991 |
| WO | 9201717 | 2/1992 |
| WO | 9208484 | 5/1992 |
| WO | 9208488 | 5/1992 |
| WO | 9314118 | 7/1993 |
| WO | 9317712 | 9/1993 |
| WO | 9318146 | 9/1993 |
| WO | 9318147 | 9/1993 |
| WO | 9321529 | 10/1993 |
| WO | 9403208 | 2/1994 |
| WO | 9403599 | 2/1994 |
| WO | 9404676 | 3/1994 |
| WO | 9411513 | 5/1994 |
| WO | WO9500654 | 1/1995 |
| WO | 9504824 | 2/1995 |
| WO | 9506725 | 3/1995 |
| WO | WO9522618 | 8/1995 |
| WO | 9524923 | 9/1995 |
| WO | 9601611 | 1/1996 |
| WO | 9602143 | 2/1996 |
| WO | 9610411 | 4/1996 |
| WO | 9610419 | 4/1996 |
| WO | 9631613 | 10/1996 |
| WO | 9706685 | 2/1997 |
| WO | 9706821 | 2/1997 |
| WO | 9706828 | 2/1997 |
| WO | 9710000 | 3/1997 |
| WO | 9710001 | 3/1997 |
| WO | 9710002 | 3/1997 |
| WO | 9726910 | 7/1997 |
| WO | 9735619 | 10/1997 |
| WO | 9823735 | 6/1998 |
| WO | 9942121 | 8/1999 |
| WO | WO0054437 | 9/2000 |
| WO | 03005964 | 1/2003 |
| WO | 2004032865 | 4/2004 |
| WO | 2005030136 | 4/2005 |
| WO | 2005092373 | 10/2005 |
| WO | WO2005113003 | 12/2005 |
| WO | WO2005120558 | 12/2005 |
| WO | 2009114085 | 9/2009 |
| WO | WO2009117116 | 9/2009 |
| WO | WO2009118247 | 10/2009 |
| WO | WO2009118733 | 10/2009 |
| WO | WO2009121483 | 10/2009 |
| WO | 2010060026 | 5/2010 |
| WO | WO2010081738 | 7/2010 |
| WO | 2011146828 | 11/2011 |

OTHER PUBLICATIONS

Barrios, C. et al., "Heat shock proteins as carrier molecules: in vivo helper effect mediated by *Escherichia coli* GroEL and DnaK proteins requires cross-linking with antigen," Clin Exp Immunol, 1994, vol. 98:229-233.

Barrios, C. et al., "Mycobacterial heat-shock proteins as carrier molecules. II: The use of the 70-kDa mycobacterial heat-shock protein as carrier for conjugated vaccinescan circumvent the need for adjuvants and Bacillus Calmette Guerin priming)," European Journal of Immunology, 1992, vol. 22, Issue 6:1365-1372 (Abstract).

Barrios, C. et al., "Specificity of antibodies induced after immunization of mice with the mycobacterial heat shock proteinof 65 kD," Clin Exp Immunol, 1994, 98:224-228.

Blachere, Nathalie E. et al., "Heat shock protein-peptide complexes, reconstituted in vitro, elicit peptide-specific cytotoxic T lymphocyte response and tumor immunity," J. Exp. Med., 1997, vol. 186, No. 8:1315-1322.

Bowen, MA et al., "Structure and expression of murinje CD30 and its role in cytokine production," The Journal of Immunology, 1996, vol. 156, No. 442-449 (Abstract).

Craig, E A., "Chaperones: Helpers Along the Pathways to Protein Folding," Science, 1993, vol. 260, No. 5:1902-1903 (Abstract).

Flynn, et al., "Peptide-binding specificity of the molecular chaperone BiP," Nature, 1991, vol. 353:726-730 (Abstract).

Flynn, et al., "Peptide binding and release by proteins implicated as catalysts of protein assembly," Science, 1989, vol. 245, No. 4916:385-390 (Abstract).

Gething, MJ: "Protein folding in the cell," Nature, 1992, vol. 355:33-45 (Abstract).

Jakob, U. et al: "Small Heat Shock Proteins Are Molecular Chaperones," The Journal of Biological Chemistry, 1993, vol. 268, No. 3:1517-1520.

Lakey, E.K. et al: "Identification of a peptide binding protein that plays a role in antigen presentation," Proc. Natl. Aced. Sci, 1987, vol. 84:1659-1663.

(56) References Cited

OTHER PUBLICATIONS

Lanzavecchia, A.: "Identifying strategies for immune intervention," Science, 1993, vol. 260, No. 5110:937-944 (Abstract).

Li, Z. and Srivastava, P.K.: Tumor rejection antigen gp96/grp94 is an ATPase: implications for protein folding and antigen presentation, The EMBO Journal, 1993, vol. 12, No. 8:3143-3151.

Lindquist, S. "The heat-shock proteins,", Annu. Rev. Genet., 1988, vol. 22:631-77.

Lukacs, L.V. et al: "Tumor cells transfected with a bacterial heat-shock gene lose tumorigenicity and induce protection against tumors," J. Exp. Med, 1993, vol. 178:343-348.

Lussow, A.R. et al: "Mycobacterial heat-shock proteins as carrier molelcules," Eur J Immunol, 1991, vol. 21:2297-302 (Abstract).

Maki, R.G. et al: "Human homologue of murine tumor rejection antigen gp96: 5'-Regulatory and coding regions and relationship to stress-induced proteins," Proc. Nat. Acad. Sci, 1990, vol. 87:5658-5662.

Maki, R.G. et al: "Mapping of the genes for human endoplasmic reticular heat shock protein gp96/grp94," Somatic Cell and Molecular Genetics, 1993, vol. 19, No. 1:73-81 (Abstract).

McCall, C.A. et al: "Biotherapy: A new dimension in cancer treatment," 1989, Nature Biotechnology 7231-240 (Abstract).

Menoret, A. et al: "Co-segregation of tumor immunogenicity with expression of inducible but not constitutive hsp70 in rat colon carcinomas," The Journal of Immunology, 1995, vol. 155, No. 2:740-747 (Abstract).

Munro, Sean and Pelham, H. R.B.: "A C-terminal signal prevents secretion of luminal ER proteins," Cell, 1987, vol. 48, Issue 5:899-907 (Abstract).

Pidoux, A.L. and Armstrong, J.: "Analysis of the BiP gene and identification of an ER retenton signal in *Schizosaccharomyces pombe*," The EMBO Journal, 1992, vol. 11, No. 4:1583-1591.

Rothman, J.E.: "Polypeptide chain binding proteins: catalysts of protein folding and related processes in cells," Cell, 1989, vol. 59, No. 4:591-601 (Abstract).

Srivastava, P.K., et al: "Heat shock proteins transfer peptides during antigen processing and CTL priming," Immunogenetics, 1994, vol. 39:93-98.

Srivastava, P.K., et al: "Chromosomal assignment of the gene encoding the mouse tumor rejection antigen gp96," Immunogenetics, 1988, vol. 28:205-207.

Srivastava, P.K., et al: "Tumor rejection antigens of chemically induced sarcomas of inbred mice," Proc. Natl. Acad. Sci, 1986, vol. 83: 3407-3411.

Srivastava, P.K. and Das, M.R.: "The serologically unique cell surface antigen of zajdela ascitic hepatoma is also its tumor-associated transplantation antigen," International Journal of Cancer, 1984, vol. 33, Issue 3:417-422 (Abstract).

Srivastava, P.K. and Old, L.J.: "Individually distinct transplantation antigens of chemically induced mouse tumors," Immunology Today, 1988, vol. 9, Issue 3:78-83 (Abstract).

Suto, R. and Srivastava, P.K.: "A mechanism for the specific immunogenicity of heat shock protein-chaperoned peptides," Science, 1995, vol. 269, No. 5230:1585-1588 (Abstract).

Udono, H., et al: "Cellular requirements for tumor-specific immunity elicited by heat shock proteins: tumor rejection antigen gp96 primes CD8+ T cells in vivo," Proc. Natl. Acad. Sci, 1994, vol. 91:3077-3081.

Udono, H. and Srivastava, P.K.: "Heat shock protein 70-associated peptides elicit specific cancer immunity," J. Exp. Med., 1993, vol. 178:1391-1396.

Udono, H. and Srivastava, P.K.: Comparison of tumor-specific immunogenicities of stress-induced proteins gp96, hsp90, and hsp70, The Journal of Immunology, 1994, vol. 152, No. 11:5398-5403 (Abstract).

Ullrich, S.J. et al: "A mouse tumor-specific transplantation antigen is a heat shock-related protein," Biochemistry, 1986, Proc. Natl. Acad. Sci., 1986, vol. 83:3121-3125.

Van Den Eynde, B. et al: "The gene coding for a major tumor rejection antigen of tumor P815 is identical to the normal gene of syngeneic DBA/2 Mice," J. Exp. Med., 1991, vol. 173:1373-1384.

Vanbuskirk, A. et al: "A peptide binding protein having a role in antigen presentation is a member of the HSP70 heat shock family," J. Exp. Med., 1989, vol. 170:1799-1809.

Welch, W.J. and Feramisco, J.R.: "Rapid purification of mammalian 70,000-dalton stress proteins: affinity of the proteins for nucleotides," Mol. Cell. Biol., 1985, vol. 5, No. 6:1229-1237 (Abstract).

Welch, W.J. and Suhan, J.P.: "Morphological study of the mammalian stress response: characterization of changes in cytoplasmic organelles, cytoskeleton, and nucleoli, and appearance of intranuclear actin filaments in rat fibroblasts after heat-shock treatment," The Journal of Cell Biology, 1985, vol. 101, No. 4:1198-1211 (Abstract).

Janetzki, S. et al: "Immunization of cancer patients with autologous cancer-derived heat shock protein gp96 preparations: a pilot study," Int. J. Cancer, 2000, vol. 88:232-238.

Tamura, Y. et al: "Immunotherapy of tumors with autologous tumor-derived heat shock protein preparations," Science Magazine, 1997, vol. 278:117-120 (Abstrct).

Meerovitch, K. et al: "Proparathyroid hormone-related protein is associated with the chaperone protein BiP and undergoes proteasome-mediated degradation," The Journal of Biological Chemistry, vol. 273:21025-21030.

Bodey, B. et al: Failure of cancer vaccines: the significant limitations of this approach to immunotherapy,: Anticancer Research, 2000, vol. 20:2665-2676.

Boon, T.: "Toward a genetic analysis of tumor rejection antigens," Avances in Cancer Research, 1992, vol. 58:177-210.

Breloer, M. et al: "Isolation of processed, H-2K-binding ovalbumin-derived peptides associated withthe stress proteins HSP70 and GP96," Eur. J. Immunol., 1998, vol. 28:1018-1021.

Dai, J. et al: "Cell surface expression of heat shock protein gp96 enhances cross-presentation of cellular antigens and the generation of tumor-specific T cell memory," Cancer Immunity, 2003, vol. 3:1-11.

De Gruijl, T. and Curiel, D.T.: "Cancer vaccine strategies get bigger and better," Nature Medicine, 1999, vol. 5, No. 10:1124-1125.

Evans, T.R.J. and Kaye, S.B.: "Vaccine therapy for cancer—fact or fiction," 1999, Q.J. Med., vol. 92:299-307.

Heike et al. "Heat shock protein-peptide complexs for use in vaccines" J. Leukocyte Biol., vol. 60, No. 2, pp. 153-158 (1996).

Oizumi, et al. "Molecular and cellular requirements for enhanced antigen cross-presentation to CD8 cytotoxic T lymphocytes" J. Immunol., vol. 179, No. 4, pp. 2310-2317 (2007).

Štrbo et al. "Heat shock fusion protein gp96-lg mediates strong CD8 CTL expansion in vivo" Am. J. Reprod., Immunol., vol. 48, No. 4, pp. 220-225 (2002).

Yamazaki et al. "Tumor secreted heat shock-fusion protein elicits CD8 cells for rejection" J. Immunol., vol. 163, No. 10, pp. 5178-5182 (1999).

Int'l Search Report for PCT/US2009/001727, mailed Dec. 2, 2009.

Written Opinion for PCT/US2009/001727, mailed Dec. 2, 2009.

Podack, ER et al.: "Immunotherapy for lung tumors: M17-01," Journal of Thoracic Oncology, 2007, vol. 2(8), Supplement 4: 5197-5198.

Yu, W. et al: "Clinical trials with oncolytic adenovirus in China," Current Cancer Drug Targets, 2007, vol. 7:141-148.

Podack, ER et al: "Allogeneic tumor-cell-based vaccines secreting endoplasmic reticulum chaperone gp96," Expert Opin. Biol. Ther., 2007, vol. 7 (11):1679-1688.

Raez, Luis E. et al.: "Lung cancer immunotherapy," Clinical Medicine & Research, 2005, vol. 3, No. 4:221-228.

Ezzell, C.: "Cancer "vaccines": an idea whose time has come?", The Journal of Research, 1995, vol. 7:46-49.

Gaiger, A. et al: "Immunity to WT1 in the animal model and in patients with acute myeloid leukemia," Blood, 2000, vol. 95, No. 4:1480-1489.

Gullo, C. and Teoh, G.: "Heat shock proteins: to present or not, that is the question," Immunology Letters, 2004, vol. 94:1-10.

(56) References Cited

OTHER PUBLICATIONS

Heike, M. et al: Protective cellular immunity against a spontaneous mammary carcinoma from ras Transgenic Mice, Immunobiology, 1994, vol. 190:411-423 (Abstract).
Inoue, S. et al: "Inhibitory effects of B cells on antitumor immunity," Cancer Res, 2005, vol. 66:7741-7747.
Li, J. et al: "Heat shock protein 70 fused to or complexed with hantavirus nucleocapsid protein significantly enhances specific humoral and cellular immune responses in C57BL/6 mice," Vaccine, 2008, vol. 26:3175-3187.
Lucacs, KV et al: "In vivo gene therapy of malignant tumours with heat shock protein-65 gene," Gene Therapy, 1997, vol. 4:346-350.
Multhoff, G. et al: "Heat shock protein 72 tumor cells," The Journal of Immunology, 1997, vol. 158:4341-4350.
Nicchitta, C.V.: "Biochemical, cell biological and immunological issues surrounding the endoplasmic reticulum chaperone GRP94/gp96," Current Opinion in Immunology, 1998, vol. 10:103-109.
Srivastava, P.K. et al: Identification of a human homologue of the murine tumor rejection antigen GP96, Cancer Res, 1989, vol. 49:1341-1343.
Oizumi, S. et al: "Surmounting tumor-induced immune suppression by frequent vaccination or immunization in the absence of B cells," J. Immunotherapy, 2008, vol. 31:394-401.
Philip, R. et al: "Efficient and sustained gene expression in primary T lymphocytes and primary and cultured tumor cells mediated by adeno-associated virus plasmid DNA complexed to cationic liposomes," Molecular and Cellular Biology, 1994:2411-2418.
Podack, E. et al: "Mucosal HIV immunity generated by gp96-SIV/HIV peptide complexes secreted by allogeneic cell," AIDS Research and Human Retroviruses, vol. 24, No. Suppl. 1, p. 91, XP008143997 (Abstract).
Segal, B.H. et al: "Heat shock proteins as vaccine adjuvants in infections and cancer," Drug Discovery Today, 2006, vol. 11:534-540.
Spitler, L.E.: "Cancer Vaccines: The Interferon Analogy," Cancer Biotherapy, 1995, vol. 10:1-3.
Srivastava, P.K.: "Peptide-binding heat shock proteins in the endoplasmic reticulum: role in immune response to cancer an in antigen presentations," Advances in Cancer Research, 1993 (Abstract).
Strbo, N. et al: "Cell-secreted Gp96-Ig-peptide complexes induce lamina propria and intraepithelial CD8+ cytotoxic T lymphocytes in the intestinal mucosa," Immunology, 2010, vol. 3, No. 2 :182-192.
Strbo, N. et al: "Gp96SIV Ig immunization induces potent polyepitope specific, multifunctional memory responses in rectal and vaginal mucosa," Vaccine, 2011, vol. 29, No. 26:2619-2626.
Zuegel, U. et al: "gp96-peptide vaccination of mice against intracellular bacteria," Infect. Immun., 2001, vol. 69 (6):4164-4167.
Strbo, N. et al: "OAO5-04. Gp96-Ig-SIV vaccines induce predominant immune responses at mucosal sites," Retrovirology, 2009, vol. 6:1.
Strbo, N. and Podack, ER.: "Secreted heat shock protein gp96-Ig: an innovative vaccine approach," American Journal of Reproductive Immunology, 2008, vol. 59:407-416.
Strbo, N. et al: "Secreted gp-96-Ig mediates CD8 and NK cell expansion," FASEB Journal, vol. 16, No. 4, 2002, XP008143902 (Abstract).
Strbo, N. et al: "SIV-gp96-Ig vaccine induces high levels of adaptive mucosal CD8 effector cells in rhesus macaques," Journal of Medical Primatology, 2010, vol. 39, X008143996 (Abstract).
Yamazaki, K. et al: "Induction of tumor immunity by gp96 secreted from engineered tumor cells," 2000, Lung Cancer, vol. 29, No. 1, XP027413932 (Abstract).
Zheng, H. et al: "Cell surface targeting of heat shock protein gp96 induces dendritic cell maturation and antitumor immunity," The Journal of Immunology, 2001, vol. 167:6731-6735.
Zinn, K. et al: "Regulated expression of an extrachromosomal human β-interferon gene in mouse cells," Proc. Natl. Acad. Sci, 1982, vol. 79:4897-4901.

Wang, X-Y. et al: "Characterization of heat shock protein 110 and glucose-regulated protein 170 as cancer vaccines and the effect of fever-range hyperthermia on vaccine activity," J Immunol, 2001, vol. 166:490-497.
Young, R.A.: "Stress proteins and immunology," Annu. Rev. Immunol., 1990, vol. 8:401-420.
Welch, W.J. et al: "Purification of the major mammalian heat shock proteins," The Journal of Biological Chemistry, 1982, vol. 257, No. 24:14949-14959.
Viitanen, Paul V. et al: "Mammalian mitochondrial chaperonin 60 functions as a single toroidal ring", The Journal of Biological Chemistry, 1992, vol. 267, No. 2:695-698.
Wheeler, CM.: "Preventive vaccines for cervical cancer," Salud Publica Mex, 1997, vol. 39:283-287.
Burton, D.R. et al: "Why do we not have an HIV vaccine and how can we make one?," Nature Medicine, 1998, vol. 4:495-498.
Desrosiers, Ronald C.: "Prospects for an AIDS vaccine", Nature Medicine, Mar. 2004, vol. 10, No. 3:221-223.
Girard, M.P. et al: "A review of vaccine research and development: the human immunodeficiency virus (HIV)," Vaccine, 2006, vol. 24:4062-4081.
Matthews, T.J. et al: "Prospects for development of a vaccine against HTLV-III-related disorders," AIDS Research and Human Retroviruses, 1987, vol. 3:197-206.
Strbo, Natasa, et al.: "HLA A2 restricted HIV specific mucosal and systemic immunity induced with secreted heat shock protein gp96-Ig," The FASER Journal, 2008, vol. 22.
Anonymous, Novel tumor vaccine pg96-Ig fusion protein in advanced (stage IIIB), relapsed or metastatic (stage IV) non-small cell lung cancer (NSCLC) patients who have failed first line chemotherapy, ClinicalTrials.gov archive, Dec. 27, 2007; <<http://clinicaltrials.gov/archive/NCT00503568/2007_12_27>>.
Kovalchin, J. T. et al., "Determinants of efficacy of immunotherapy with tumor-derived heat shock protein gp96.", Cancer Immunity, Apr. 27, 2001, vol. 1:7.
"Vaccine therapy in treating patients with Stage III, Stage IV, or relapsed non-small cell lung cancer treated with first-line chemotherapy," Jul. 18, 2007. Retrieved from the Internet: URL: http://clinicaltrials.gov/archive/NCT00503568.
Abbas et al., "Functional diversity of helper T lymphocytes," *Nature*, 383(6603):787-793, Oct. 1996.
Adams et al., "Molecular cloning of mouse immunoglobulin heavy chain messenger ribonucleic acids coding for mu, alpha, gamma 1, gamma 2a, and gamma 3 chains," *Biochemistry*, 19(12):2711-2719, Jun. 10, 1980.
Adams et al., "The c-myc oncogene driven by immunoglobulin enhancers induces lymphoid malignancy in transgenic mice," *Nature*, 318(6046):533-538, Dec. 12-18, 1985.
Adjei and Garren, "Pulmonary delivery of peptide drugs: effect of particle size on bioavailability of leuprolide acetate in healthy male volunteers," *Pharm Res.*, 7(6):565-569, Jun. 1990.
Adjei et al., "Bioavailability of leuprolide following intratracheal administration to beagle dogs," *Int. J. Pharmaceutics*, 63(1-2):135-144, Jun. 11, 1990.
Alexander et al., "Expression of the c-myc oncogene under control of an immunoglobulin enhancer in E mu-myc transgenic mice," *Mol Cell Biol.*, 7(4): 1436-1444, Apr. 1987.
Altmeyer et al., "Tumor-specific cell surface expression of the-KDEL containing, endoplasmic reticular heat shock protein gp96," *Int J Cancer.*, 69(4):340-349, Aug. 22, 1996.
Ames, "Identifying environmental chemicals causing mutations and cancer," *Science*, 204(4393):587-593, May 11, 1979.
Ausubel et al., ed., 1999, Short Protocols in Molecular Biology (4th Edition, John Wiley & Sons. Inc., New York) Unit 10.11, pp. 10-86 to 10-88.
Banchereau and Steinman, "Dendritic cells and the control of immunity," *Nature*, 1988, 392(6673):245-252, Mar. 19, 1998.
Bardwell and Craig, "Major heat shock gene of *Drosophila* and the *Escherichia coli* heat-inducible dnaK gene are homologous," *Proc Natl Acad Sci U S A.*, 81(3):848-852, Feb. 1984.
Barrios et al., "Mycobacterial heat-shock proteins as carrier molecules. II: The use of the 70-kDa mycobacterial heat-shock protein as

(56) References Cited

OTHER PUBLICATIONS carrier for conjugated vaccines can circumvent the need for adjuvants and Bacillus Calmette Guérin priming," *Eur J Immunol.,* 22(6):1365-1372, Jun. 1992.
Bartlett, "Effect of host immunity on the antigenic strength of primary tumors," *J Natl Cancer Inst.,* 49(2):493-504, Aug. 1972.
Belli et al., "Vaccination of metastatic melanoma patients with autologous tumor-derived heat shock protein gp96-peptide complexes: clinical and immunologic findings," *J Clin Oncol.,* 20(20):4169-4180, Oct. 15, 2002.
Beltràn and Colomer, "Does HER-2 status predict only a decreased response to hormone therapy in advanced breast cancer, or does it also predict the extent of metastatic disease?" *J Clin Oncol.,* 20(23):4605-4610, Dec. 1, 2002.
Belyaysky et al., "PCR-based cDNA library construction: general cDNA libraries at the level of a few cells," *Nucleic Acids Res.,* 17(8):2919-2932, Apr. 25, 1989.
Benhamou and Siraganian, "Protein-tyrosine phosphorylation: an essential component of Fc epsilon RI signaling," *Immunol Today,* 13(6):195-197, Jun. 1992.
Benoist and Chambon, "In vivo sequence requirements of the SV40 early promotor region," *Nature,* 290(5804):304-310, Mar. 26, 1981.
Benton and Davis, "Screening lambdagt recombinant clones by hybridization to single plaques in situ," *Science,* 196(4286):180-182, Apr. 8, 1977.
Bernard et al., 1981, "Plasmacytomas with more than one immunoglobulin kappa mRNA: implications for allelic exclusion", *Proc Natl Acad Sci U S A.,* 78(9):5812-5816, Sep. 1981.
Bernhardt et al., "Telomerase peptide vaccination of patients with non-resectable pancreatic cancer: A dose escalating phase I/II study," *Br J Cancer.,* 95(11):1474-1482, Epub Oct. 24, 2006.
Bitter et al., "[33] Expression and secretion vectors for yeast," *Methods Enzymol.,* 153:516-544, 1987.
Bitter, "[70] Heterologous gene expression in yeast," *Methods Enzymol.,* 152: 673-684, 1987.
Blachere et al., "Heat shock protein vaccines against cancer," *J Immunother Emphasis Tumor Immunol.,* 14(4):352-356, Nov. 1993.
Blachere et al., "Immunization with GP96 heat shock proteins isolated from tumors or influenza virus infected cells elicits MHC-restricted, antigen-specific cytotoxic T lymphocytes against the corresponding cells/antigens" *J. Cell. Biochem.,* 53 (S17D):124, Abstract NZ 502, Mar. 13, 1993.
Boesen et al., "Circumvention of chemotherapy-induced myelosuppression by transfer of the mdrl gene," *Biotherapy,* 6(4):291-302, 1994.
Boon et al., "Tumor antigens recognized by T lymphocytes," *Annu. Rev. Immunol.,* 12:337-365, Apr. 1994.
Bowen et al., "Structure and expression of murine CD30 and its role in cytokine production," *J Immunol.,* 156(2):442-449, Jan. 15, 1996.
Braquet et al., "Effect of endothelin-1 on blood pressure and bronchopulmonary system of the guinea pig," *J Cardiovasc Pharmacol.,* 13(Suppl. 5):S143-S146, 1989.
Brinster et al., "Regulation of metallothionein—thymidine kinase fusion plasmids injected into mouse eggs," *Nature,* 296(5852):39-42, Mar. 4, 1982.
Bumol et al., "Characterization of the human tumor and normal tissue reactivity of the KS1/4 monoclonal antibody," *Hybridoma,* 7(4):407-415, Aug. 1988.
Cappechi, "High efficiency transformation by direct microinjection of DNA into cultured mammalian cells," *Cell,* 22(2 Pt 2):479-488, Nov. 1980.
Carswell et al., "Immunogenic properties of reticulum cell sarcomas of SJL/J mice," *J Natl Cancer Inst.,* 44(6):1281-1288, Jun. 1970.
Catalona et al., "Detection of organ-confined prostate cancer is increased through prostate-specific antigen-based screening," JAMA, 270(8):948-954, Aug. 25, 1993.
Chang et al., "Synergistic effect of 4-hydroperoxycyclophosphamide and etoposide on a human promyelocytic leukemia cell line (HL-60) demonstrated by computer analysis," *Cancer Res.* 45:2434-2439, Jun. 1985.

Chen et al., "Expression of ssDNA in mammalian cells," *Biotechniques,* 34(1):167-71, Jan. 2003.
Choulika et al., "Transfer of single gene-containing long terminal repeats into the genome of mammalian cells by a retroviral vector carrying the cre gene and the loxP site," *J Virol.,* 70(3):1792-1798, Mar. 1996.
Cline, "Perspectives for gene therapy: inserting new genetic information into mammalian cells by physical techniques and viral vectors," *Pharmac. Ther.,* 29(1):69-92, 1985.
Clontech catalog 1995-1996, Table of Contents, and pp. 137-138.
Clontech catalog 1997-1998, p. 146, 147, 149, 150, 151, 153.
Clontech catalog, "Talon Metal Affinity Resin", 1997-1998, 2 pages.
Colbère-Garapin et al., "A new dominant hybrid selective marker for higher eukaryotic cells," *J Mol Biol.,* 150(1):1-14, Jul. 25, 1981.
Colombo et al., "Direct in vivo DC targeting by cellular vaccines engineered to express OX-40UGM-CSF or soluble HSP70", 93rd Annual Meeting of the American Association of Cancer Research. Mar. 2002, Abstract #3370.
Cotten et al., "[42] Receptor-mediated transport of DNA into eukaryotic cells," *Methods Enzymol.,* 217:618-644, 1993.
Craig, "Chaperones: helpers along the pathways to protein folding" *Science,* 260(5116):1902-1903, Jun. 25, 1993.
Curiel et al., "Adenovirus enhancement of transferrin-polylysine-mediated gene delivery," *Proc Natl Acad Sci U S A.,* 88(19):8850-8854, Oct. 1, 1991.
Current Protocols in Molecular Biology, vol. 3, Nov. 1988, 1 page [synopsis].
Davidson et al., "A model system for in vivo gene transfer into the central nervous system using an adenoviral vector," *Nat Genet.,* 3(3):219-223, Mar. 1993.
Davis et al., "Direct gene transfer into skeletal muscle in vivo: factors affecting efficiency of transfer and stability of expression," *Hum Gene Ther.,* 4(2):151-159, Apr. 1993.
de Boer et al., "The tac promoter: a functional hybrid derived from the trp and lac promoters," *Proc Natl Acad Sci U S A.,* 80(1):21-25, Jan. 1983.
Debs et al., "Lung-specific delivery of cytokines induces sustained pulmonary and systemic immunomodulation in rats," *J. Immunol.,* 140(10):3482-3488, May 15, 1988.
Demotz et al, "Characterization of a naturally processed MHC class II-restricted T-cell determinant of hen egg lysozyme," *Nature,* 342(6250):682-684, Dec. 7, 1989.
di Guan et al., "Vectors that facilitate the expression and purification of foreign peptides in *Escherichia coli* by fusion to maltose-binding protein," *Gene,* 67(1):21-30, Jul. 15, 1988.
Dolby et al., "Cloning and partial nucleotide sequence of human immunoglobulin mu chain cDNA from B cells and mouse-human hybridomas," *Proc Natl Acad Sci U S A.,* 77(10):6027-6031, Oct. 1980.
Dols et al., "Vaccination of women with metastatic breast cancer, using a costimulatory gene (CD80)-modified, HLA-A2-matched, allogeneic, breast cancer cell line: clinical and immunological results," *Hum Gene Ther.,* 14(11):1117-1123, Jul. 20, 2003.
Domec et al., "cDNA library construction from small amounts of unfractionated RNA: association of cDNA synthesis with polymerase chain reaction amplification," *Anal Biochem.,* 188(2):422-426, Aug. 1, 1990.
Ebert et al., "Characterization of an immunosuppressive factor derived from colon cancer cells," *J Immunol.,* 138(7):2161-2168, Apr. 1, 1987.
Elliott et al., "Antigen presentation. Naturally processed peptides," *Nature,* 348(6298):195-197, Nov. 15, 1990.
Estin et al., "Transfected mouse melanoma lines that express various levels of human melanoma-associated antigen p97," *J Natl Cancer Inst.,* 81(6):445-448, Mar. 15, 1989.
Falk et al., "Allele-specific motifs revealed by sequencing of self-peptides eluted from MHC molecules" *Nature,* 351(6324):290-296, May 23, 1991.
Falk et al., "Cellular peptide composition governed by major histocompatibility complex class I molecules," *Nature,* 348(6298):248-251, Nov. 15, 1990.
Falkner and Zachau, "Expression of mouse immunoglobulin genes in monkey cells," *Nature,* 298(5871):286-288, Jul. 15, 1982.

(56) References Cited

OTHER PUBLICATIONS

Feldweg and Srivastava, "Evidence for biochemical heterogeneity of gp96 heat shock protein/tumor rejection antigen," *J Cell Biochem.*, Suppl. 17D:108, Abstract NZ 206, 1993.
Feldweg and Srivastava, "Molecular heterogeneity of tumor rejection antigen/heat shock protein GP96," *Int J Cancer.*, 63(2):310-314, Oct. 9, 1995.
Flynn, et al., "Peptide binding and release by proteins implicated as catalysts of protein assembly," *Science*, 245(4916):385-390, Jul. 28, 1989.
Flynn, et al., "Peptide-binding specificity of the molecular chaperone BiP," *Nature*, 353(6346):726-730, Oct. 24, 1991.
Fong and Engleman, "Dendritic cells in cancer immunotherapy," *Annu Rev Immunol.*, 18:245-273, 2000.
Franklin, "Making vaccines fit the cancer," *New Scientist*, 140:17, 1993.
Geller and Freese, "Infection of cultured central nervous system neurons with a defective herpes simplex virus 1 vector results in stable expression of *Escherichia coli* beta-galactosidase," *Proc Natl Acad Sci U S A*, ;87(3):1149-1153, Feb. 1990.
Geller et al., "An HSV-1 vector expressing tyrosine hydroxylase causes production and release of L-dopa from cultured rat striatal cells," *J. Neurochem*, 64:487-496, Feb. 1995.
Geller et al., "Long-term increases in neurotransmitter release from neuronal cells expressing a constitutively active adenylate cyclase from a herpes simplex virus type 1 vector," *Proc Natl Acad Sci U S A*, 90(16):7603-7607, Aug. 15, 1993.
Genebank Accession M16370, GI:200582, "Mouse polymorphic tumor rejection antigen (gp96), 5' end," Apr. 27, 1993, 1 page.
Genebank Accession M19645, GI:183644, "Human 78 kdalton glucose-regulated protein (GRP78) gene, complete cds," Nov. 8, 1994, 3 pages.
Genebank Accession M24743, GI:188527, "Human MHC class III heat shock protein HSP70-1 gene, 5' end," Jan. 7, 1995, 1 page.
Genebank Accession M35021, GI:194022, "Mouse heat shock protein 70.1 (hsp70.1) gene, complete cds," Mar. 26, 1994, 2 pages.
Genebank Accession U16277, GI:829364, "Mus musculus 78 kDa glucose-regulated protein (grp78) gene, promoter region and partial cds," Sep. 29, 1995, 2 pages.
Genebank Accession X15187, GI:37260, "Human tra1 mRNA for human homologue of murine tumor rejection antigen gp96," Mar. 31, 1995, 2 pages.
Gething and Sambrook, "Protein folding in the cell," *Nature*, 355(6355):33-45, Jan. 2, 1992.
Gething et al., "Expression of wild-type and mutant forms of influenza hemagglutinin: the role of folding in intracellular transport," *Cell*, 46(6):939-50, Sep. 12, 1986.
Glasebrook and Fitch, "Alloreactive cloned T cell lines. I. Interactions between cloned amplifier and cytolytic T cell lines," *J Exp Med.*, 151(4):876-895, Apr. 1, 1980.
Gorman, "Mammalian cell expression," *Curr Opin Biotechnol.*, 1(1):36-47, Oct. 1990.
Gough et al., "Molecular cloning of seven mouse immunoglobulin kappa chain messenger ribonucleic acids," *Biochemistry*, 19(12):2702-2710, Jun. 10, 1980.
Graham et al., "Characteristics of a human cell line transformed by DNA from human adenovirus type 5," *J Gen Virol.*, 36(1):59-74, Jul. 1977.
Grosschedl et al., "Introduction of a mu immunoglobulin gene into the mouse germ line: specific expression in lymphoid cells and synthesis of functional antibody," *Cell*, 38(3):647-658, Oct. 1984.
Grossman and Wilson, "Retroviruses: delivery vehicle to the liver," *Curr Opin Genet Dev.*, 3(1):110-114, Feb. 1993.
Grunstein and Hogness, "Colony hybridization: a method for the isolation of cloned DNAs that contain a specific gene," *Proc Natl Acad Sci U S A*, 72(10):3961-3965, Oct. 1975.
Haas and Meo, "cDNA cloning of the immunoglobulin heavy chain binding protein," *Proc Natl Acad Sci U S A*, 85(7):2250-2254, Apr. 1988.
Haas and Wabl, "Immunoglobulin heavy chain binding protein," *Nature*, 306(5941):387-389, Nov. 24-30, 1983.
Hamer et al., "SV40 recombinants carrying rabbit beta-globin gene coding sequences," *Cell*, 17(3):725-735, Jul. 1979.
Hanahan, "Heritable formation of pancreatic beta-cell tumours in transgenic mice expressing recombinant insulin/simian virus 40 oncogenes," *Nature*, 315(6015):115-22, May 9-15, 1985.
Hauser et al., "Secretory heat-shock protein as a dendritic cell-targeting molecule: a new strategy to enhance the potency of genetic vaccines," *Gene Ther.*, 11:924-932. Jun. 2004.
Healthcare Professionals—Results of Past Trials, Retrieved from Website of Antigenics Inc. on the Internet at: <URL: www.antiqenics.com/p healthcare03.html> on Oct. 19, 2001, 10 pages.
Heike et al., "Protective cellular immunity against a spontaneous mammary carcinoma from ras transgenic mice," *Immunobiology*, 190(4-5):411-423, Jun. 1994.
Henttu and Vihko, "cDNA coding for the entire human prostate specific antigen shows high homologies to the human tissue kallikrein genes," *Biochem Biophys Res Commun.* 160(2):903-910, Apr. 28, 1989.
Hickey et al., "Sequence and regulation of a gene encoding a human 89-kilodalton heat shock protein," *Mol Cell Biol.*, 9(6):2615-2626, Jun. 1989.
Hickey, "Basic principles of immunological surveillance of the normal central nervous system," *Glia*, 36(2):118-124, Nov. 2001.
Hill et al., "Mutagenesis with degenerate oligonucleotides: an efficient method for saturating a defined DNA region with base pair substitutions," *Methods Enzymol.*, 155:558-568, 1987.
Ho et al., "Site-directed mutagenesis by overlap extension using the polymerase chain reaction," *Gene*, 77(1):51-59, Apr. 15, 1989.
Holmskov et al., "Collectins: collagenous C-type lectins of the innate immune defense system," *Immunol Today*, 15(2):67-74, Feb. 1994.
Hoover et al., "Adjuvant active specific immunotherapy for human colorectal cancer: 6.5-year median follow-up of a phase III prospectively randomized trial," *J Clin Oncol.*, 11(3):390-399, Mar. 1993.
Hunt and Morimoto, "Conserved features of eukaryotic hsp70 genes revealed by comparison with the nucleotide sequence of human hsp70," *Proc Natl Acad Sci U S A*, 82(19):6455-6459, Oct. 1985.
Hutchison et al., "Mutagenesis at a specific position in a DNA sequence," *J Biol Chem.*, 253(18):6551-6560, Sep. 25, 1978.
Israeli et al., "Molecular cloning of a complementary DNA encoding a prostate-specific membrane antigen," *Cancer Res.*, 53(2):227-230, Jan. 15, 1993.
Jardetzky et al., "Identification of self peptides bound to purified HLA-B27," *Nature* 353(6342):326-329, Sep. 26, 1991.
Jindal et al., "Primary structure of a human mitochondrial protein homologous to the bacterial and plant chaperonins and to the 65-kilodalton mycobacterial antigen," *Mol Cell Biol.*, 9(5):2279-2283, May 1989.
Kaplitt et al., "Long-term gene expression and phenotypic correction using adeno-associated virus vectors in the mammalian brain," *Nat Genet.*, 8(2):148-154, Oct. 1994.
Karasuyama and Melchers, "Establishment of mouse cell lines which constitutively secrete large quantities of interleukin 2, 3, 4 or 5, using modified cDNA expression vectors," *Eur J Immunol.*, 18(1):97-104, Jan. 1988.
Kelsey et al., "Species- and tissue-specific expression of human alpha 1-antitrypsin in transgenic mice," *Genes Dev.*, 1(2):161-171, Apr. 1987.
Kimmel and Berger, "[32] Preparation of cDNA and the generation of cDNA libraries: Overview" *Methods Enzymol*, 152:307-316, 1987.
Klein et al., "Demonstration of resistance against methylcholanthrene-induced sarcomas in the primary autochthonous host," *Cancer Res.*, 20:1561-1572, Dec. 1960.
Kleman et al., "Optimal conditions for freezing CHO-S and HEK293-EBNA cell lines: influence of Me2S0, freeze density, and PEI-mediated transfection on revitalization and growth of cells, and expression of recombinant protein," *Biotechnology and Bioengineering*, 100(5):911-922, Aug 1, 2008.
Koff et al., Replicating viral vectors as HIV vaccines: Summary Report from IAVI Sponsored Satellite Symposium, International AIDS Society Conference, Jul. 22, 2007, *Biologicals*, 36(5):277-286.

(56) References Cited

OTHER PUBLICATIONS

Kollias et al., "Regulated expression of human A gamma-, beta-, and hybrid gamma beta-globin genes in transgenic mice: manipulation of the developmental expression patterns," *Cell*, 46(1):89-94, Jul. 4, 1986.

Kos, "Regulation of adaptive immunity by natural killer cells," *Immunol Res.*, 17(3):303-312, 1998.

Kripke, "Antigenicity of murine skin tumors induced by ultraviolet light," *J Natl Cancer Inst.*, 53(5):1333-1336, Nov. 1974.

Krumlauf et al., "Developmental regulation of alpha-fetoprotein genes in transgenic mice," *Mol Cell. Biol.*, 5(7):1639-1648, Jul. 1985.

Lai et al., "Quantitation and intracellular localization of the 85K heat shock protein by using monoclonal and polyclonal antibodies," *Mol Cell Biol.*, 4(12):2802-2810, Dec. 1984.

Langone, "Use of labeled protein A in quantitative immunochemical analysis of antigens and antibodies," *J Immunol Methods*, 51(1):3-22, 1982.

Lanzavecchia, "Identifying strategies for immune intervention," *Science*, 260(5110):937-944, May 14, 1993.

Leder et al., "Consequences of widespread deregulation of the c-myc gene in transgenic mice: multiple neoplasms and normal development," *Cell*, 45(4):485-495, May 23, 1986.

Lee et al., "The genomic organization of the CD28 gene. Implications for the regulation of CD28 mRNA expression and heterogeneity," *J Immunol.*, 145(1):344-352, Jul. 1, 1990.

Levinson et al., "Metal binding drugs induce synthesis of four proteins in normal cells," *Biol Trace Elem Res.*, 1(1):15-23, Mar. 1979.

Lévy et al., "ATP is required for in vitro assembly of MHC class I antigens but not for transfer of peptides across the ER membrane," *Cell*, 67(2):265-274, Oct. 18, 1991.

Liu, "Treg suppress CTL responses upon immunization with HSP gp96," *Eur J Immunol.*, 39(11):3110-3120, Nov. 2009.

Loeffler and Behr, "[41] Gene transfer into primary and established mammalian cell lines with lipopolyamine-coated DNA," *Methods Enzymol.*, 217:599-618, 1993.

Logan and Shenk, "Adenovirus tripartite leader sequence enhances translation of mRNAs late after infection," *Proc Natl Acad Sci U S A.*, 81(12):3655-3659, Jun. 1984.

Lowy et al., "Isolation of transforming DNA: cloning the hamster aprt gene," *Cell*, 22(3):817-823, Dec. 1980.

Luescher et al., "Specific binding of antigenic peptides to cell-associated MHC class I molecules," *Nature*, 351(6321):72-74, May 2, 1991.

Lussow et al., "Mycobacterial heat-shock proteins as carrier molecules," *Eur J Immunol.*, 21(10):2297-2302, Oct. 1991.

MacDonald et al., "Expression of the pancreatic elastase I gene in transgenic mice," *Hepatology*, 7(1 Suppl):42S-51S, Jan.-Feb. 1987.

Machamer et al., "Heavy chain binding protein recognizes incompletely disulfide-bonded forms of vesicular stomatitis virus G protein," *J Biol Chem.*, 265(12):6879-6883, Apr. 25, 1990.

Mackett et al., "General method for production and selection of infectious vaccinia virus recombinants expressing foreign genes," *J Virol.*, 49(3):857-864, Mar. 1984.

Mackett et al., "Vaccinia virus: a selectable eukaryotic cloning and expression vector," *Proc Natl Acad Sci U S A.*, 79(23):7415-7419, Dec. 1982.

Madden et al., "The structure of HLA-B27 reveals nonamer self-peptides bound in an extended conformation," *Nature*, 353(6342):321-325, Sep. 26, 1991.

Magram et al., "Developmental regulation of a cloned adult beta-globin gene in transgenic mice," *Nature*, 315(6017):338-340, May 23-29, 1985.

Maki et al., "Mapping of the genes for human endoplasmic reticular heat shock protein gp96/grp94," *Somat Cell Mol Genet.*, 19(1):73-81, Jan. 1993.

Makrides, "Strategies for achieving high-level expression of genes in *Escherichia coli*," *Microbiol Rev.*, 60(3):512-538, Sep. 1996.

Massarelli et al., "A retrospective analysis of the outcome of patients who have received two prior chemotherapy regimens including platinum and docetaxel for recurrent non-small-cell lung cancer," *Lung Cancer*, 39(1): 55-61, 2003.

Mather, "Establishment and characterization of two distinct mouse testicular epithelial cell lines," *Biol. Reprod.*, 23:243-251, Aug. 1980.

Mazzaferro et al., "Vaccination with Autologous Tumor-derived Heat-Shock Protein Gp96 after Liver Resection for Metastatic Colorectal Cancer," *Clin Cancer Res.*, 9:3235-3245, Aug. 2003.

McCall et al, "Biotherapy: A new dimension in cancer treatment," *Nature Biotechnology* 7:231-240, 1989.

McLaughlin et al., "Adeno-associated virus general transduction vectors: analysis of proviral structures," *J Virol.*, 62(6):1963-1973, Jun. 1988.

Ménoret et al., "Co-segregation of tumor immunogenicity with expression of inducible but not constitutive hsp70 in rat colon carcinomas," *J Immunol.*, 155(2):740-747, Jul. 15, 1995.

Merrifield, "Solid Phase Peptide Synthesis. I. The Synthesis of a Tetrapeptide," *J Am Chem Soc.*, 85(14): 2149-2154, Jul. 1, 1963.

Mizoguchi et al., "Alterations in signal transduction molecules in T lymphocytes from tumor-bearing mice," *Science*, 258(5089):1795-1798, Dec. 11, 1992.

Morgenstern and Land, "Advanced mammalian gene transfer: high titre retroviral vectors with multiple drug selection markers and a complementary helper-free packaging cell line," *Nucleic Acids Res.*, 18(12):3587-3596, Jun. 25, 1990.

Morrison and Oi, "Transfer and expression of immunoglobulin genes," *Annu Rev Immunol.*, 2:239-256, 1984.

Mosmann and Sad, "The expanding universe of T-cell subsets: Th1, Th2 and more," *Immunol Today*, 17(3):138-146, Mar. 1996.

Mulligan and Berg, "Selection for animal cells that express the *Escherichia coli* gene coding for xanthine-guanine phosphoribosyltransferase," *Proc Natl Acad Sci U S A*, 78(4):2072-2076, Apr. 1981.

Munro and Pelham, "A C-terminal signal prevents secretion of luminal ER proteins," *Cell*, 48(5):899-907, Mar. 13, 1987.

Munro and Pelham, "An Hsp70-like protein in the ER: identity with the 78 kd glucose-regulated protein and immunoglobulin heavy chain binding protein," *Cell*, 46(2):291-300, Jul. 18, 1986.

Natali et al., "Immunohistochemical detection of antigen in human primary and metastatic melanomas by the monoclonal antibody 140.240 and its possible prognostic significance," *Cancer*, 59(1):55-63, Jan. 1, 1987.

Neelapu et al., "Vaccine-induced tumor-specific immunity despite severe B-cell depletion in mantle cell lymphoma," *Nat Med.*, 11(9):986-991. Epub Aug. 21, 2005.

Nielsen and Krogh, "Prediction of signal peptides and signal anchors by a hidden Markov model," *Proc Int Conf Intell Syst Mol Biol.*, 6:122-130, 1998.

Nielsen et al., "Identification of prokaryotic and eukaryotic signal peptides and prediction of their cleavage sites," *Protein Eng.*, 10(1):1-6, Jan. 1997.

O'Garra, "Cytokines induce the development of functionally heterogeneous T helper cell subsets," *Immunity*, 8(3):275-283, Mar. 1998.

O'Hare et al., "Transformation of mouse fibroblasts to methotrexate resistance by a recombinant plasmid expressing a prokaryotic dihydrofolate reductase," *Proc Natl Acad Sci U S A.*, 78(3):1527-1531, Mar. 1981.

Oizumi and Podack, "Important role of heat shock protein gp96-chaperoned peptides in efficient cross priming of CD8 T cells by rapid recruitment and activation of DC and NK cells," *Proc Amer Assoc Cancer Res.*, vol. 47, Abstract# 3136, 2006.

Oizumi et al., "Investigation of the antitumor effect of tumor cell-produced gp96 in the absence of B cells," The Japan Lung Cancer Society, 46(5):536, Abstract P-41, Oct. 2006.

Palladino et al., "Expression of a shared tumor-specific antigen by two chemically induced BALB/c sarcomas," *Cancer Res.*, 47(19):5074-5079, Oct. 1, 1987.

Panicali and Paoletti, "Construction of poxviruses as cloning vectors: insertion of the thymidine kinase gene from herpes simplex virus into the DNA of infectious vaccinia virus," 79(16):4927-4931, Aug. 1982.

(56) References Cited

OTHER PUBLICATIONS

Perrin et al., "Astrocytoma infiltrating lymphocytes include major T cell clonal expansions confined to the CD8 subset," *Int Immunol.*, 11(8):1337-1350, Aug. 1999.
Pinkert et al., "An albumin enhancer located 10 kb upstream functions along with its promoter to direct efficient, liver-specific expression in transgenic mice," *Genes Dev.*, 1(3):268-276, May 1987.
Prehn and Main, "Immunity to methylcholanthrene-induced sarcomas," *J Natl Cancer Inst.*, 18(6):769-778, Jun. 1957.
Quantin et al., "Adenovirus as an expression vector in muscle cells in vivo," *Proc Natl Acad Sci U S A*, 89(7):2581-2584, Apr. 1, 1992.
Raez et al., "Allogeneic vaccination with a B7.1 HLA-A gene-modified adenocarcinoma cell line in patients with advanced non-small-cell lung cancer," *J Clin Oncol.*, 22(14):2800-2807, Jul. 15, 2004.
Rice and Baltimore, "Regulated expression of an immunoglobulin kappa gene introduced into a mouse lymphoid cell line," *Proc Natl Acad Sci U S A*, 79(24):7862-7865, Dec. 1982.
Rothman, "Polypeptide chain binding proteins: catalysts of protein folding and related processes in cells," *Cell*, 59(4):591-601, Nov. 1989.
Rotzschke et al., "Isolation and analysis of naturally processed viral peptides as recognized by cytotoxic T cells" *Nature*, 348(6298):252-254, Nov. 15, 1990.
Roy et al., "IL-12 treatment of endogenously arising murine brain tumors," *J Immunol.*, 165(12):7293-7299, Dec. 15, 2000.
Rudensky et al., "Sequence analysis of peptides bound to MHC class II molecules," *Nature*, 353(6345):622-627, Oct. 17, 1991.
Salk et al., "A strategy for prophylactic vaccination against HIV," *Science*, 260(5112):1270-1272, May 28, 1993.
Schneider et al., "Abnormal oxidative metabolism of estradiol in women with breast cancer," *Proc Natl Acad Sci U S A.*, 79(9):3047-3051, May 1982.
Schumacher et al., "Peptide selection by MHC class I molecules," *Nature*, 350(6320):703-706, Apr. 25, 1991.
Shankarappa et al., "Introduction of multiple restriction enzyme sites by in vitro mutagenesis using the polymerase chain reaction," *PCR Methods Appl.*, 1(4):277-278, May 1992.
Shilo and Weinberg, "DNA sequences homologous to vertebrate oncogenes are conserved in *Drosophila melanogaster*," *Proc Natl Acad Sci U S A*, 78(11):6789-6792, Nov. 1981.
Shiue et al., "A second chain of human CD8 is expressed on peripheral blood lymphocytes," *J Exp. Med.*, 168(6):1993-2005, Dec. 1, 1988.
Sigma Life Science Research Immunochemicals 1998 catalog and price list © 1997, Table of Contents and pp. 144-146.
Sjöbring et al., "Streptococcal protein G. Gene structure and protein binding properties," *J Biol Chem.*, 266(1):399-405, Jan. 5, 1991.
Smith et al., "Molecular Engineering of the Autographa californica Nuclear Polyhedrosis Virus Genome: Deletion Mutations Within the Polyhedrin Gene," *J. Virol.*, 46(2):584-593, May 1983.
Smith et al., "Pulmonary deposition and clearance of aerosolized alpha-1-proteinase inhibitor administered to dogs and to sheep," *J Clin Invest.*, 84(4):1145-1154, Oct. 1989.
Srivastava and Das, "The serologically unique cell surface antigen of Zajdela ascitic hepatoma is also its tumor-associated transplantation antigen," *Int J Cancer.*, 33(3):417-422, Mar. 15, 1984.
Srivastava and Maki, "Stress-induced proteins in immune response to cancer," *Curr Top Microbiol Immunol.*, 167:109-123, 1991.
Srivastava and Old, "Individually distinct transplantation antigens of chemically induced mouse tumors," *Immunol Today.*, 9(3):78-83, Mar. 1988.
Srivastava et al., "5'-structural analysis of genes encoding polymorphic antigens of chemically induced tumors," *Proc Natl Acad Sci U S A*, 84(11):3807-3811, Jun. 1987.
Srivastava et al., "Evidence for peptide-chaperoning by the endoplasmic reticular heat shock protein GP96: Implications for vaccination against cancer and infectious diseases" *J. Cell. Biochem.* Supp. 17D: 94 Abstract NZ 014, 1993.
Srivastava, "Peptide-binding heat shock proteins in the endoplasmic reticulum: role in immune response to cancer an in antigen presentation," *Adv Cancer Res.*, 62:153-177, 1993.
Srivastava, "Protein tumor antigens," *Curr Opin Immunol.*, 3(5):654-658, Oct. 1991.
Staveley-O'Carroll et al., "Induction of antigen-specific T cell anergy: An early event in the course of tumor progression," *Proc Natl Acad Sci U S A.*, 95(3):1178-1183, Feb. 3, 1998.
Stratford-Perricaudet et al., "Widespread long-term gene transfer to mouse skeletal muscles and heart," *J Clin Invest.*, 90(2):626-630, Aug. 1992.
Strbo et al., "Heat shock fusion protein gp96-Ig mediates strong CD8 CTL expansion in vivo," *Am J Reprod Immunol.*, 48(4):220-225, Oct. 2002.
Subbarao and Murphy, "A general overview of viral vaccine development," *Adv Exp Med Biol.*, 327:51-56, 1992.
Suto and Srivastava, "A mechanism for the specific immunogenicity of heat shock protein-chaperoned peptides," *Science*, 269(5230):1585-1588, Sep. 15, 1995.
Szybalska and Szybalski, "Genetics of human cess line. IV. DNA-mediated heritable transformation of a biochemical trait," *Proc Natl Acad Sci U S A*, 48:2026-2034, Dec. 15, 1962.
Tailor et al., "Nucleotide sequence of human prostatic acid phosphatase determined from a full-length cDNA clone," *Nucleic Acids Res.*, 18(16):4928, Aug. 25, 1990.
Tamura et al., "Immunotherapy of tumors with autologous tumor-derived heat shock protein preparations," *Science*, 278(5335):117-120, Oct. 3, 1997.
Taylor and Kingston, "Factor substitution in a human HSP70 gene promoter: TATA-dependent and TATA-independent interactions," *Mol Cell Biol.*, 10(1):165-175, Jan. 1990.
Thompson et al., "The CLUSTAL_X windows interface: flexible strategies for multiple sequence alignment aided by quality analysis tools," *Nucleic Acids Res.*, 25(24):4876-4882, Dec. 15, 1997.
Toes, "Peptide vaccination can lead to enhanced tumor growth through specific T-cell tolerance induction," *Proc Natl Acad Sci U S A.*, 93(15):7855-7860, Jul. 23, 1996.
Udono and Srivastava, "Comparison of tumor-specific immunogenicities of stress-induced proteins gp96, hsp90, and hsp70," *J Immunol.*, 152(11):5398-5403, Jun. 1, 1994.
Udono and Srivastava, "Heat shock proteins HSP70, HSP90 and GP96 elicit tumor specific immunity to the tumors from which they are isolated" *J. Cell. Biochem.* Suppl. 17D: 1131 Abstract NZ2251, 1993.
Urlaub and Chasin, "Isolation of Chinese hamster cell mutants deficient in dihydrofolate reductase activity," *Proc Natl Acad Sci U S A.*, 77(7):4216-4220, Jul. 1980.
Vaage, "Nonvirus-associated antigens in virus-induced mouse mammary tumors," *Cancer Res.*, 28(12):2477-2483, Dec. 1968.
Van Doren and Gluzman, "Efficient transformation of human fibroblasts by adenovirus-simian virus 40 recombinants," *Mol Cell Biol.*, 4(8):1653-1656, Aug. 1984.
VanBogelen et al., "Induction of the heat shock regulon does not produce thermotolerance in *Escherichia coli*," *Genes Dev.*, 1(6):525-531, Aug. 1987.
Vijayasaradhi et al., "The melanoma antigen gp75 is the human homologue of the mouse b (brown) locus gene product," *J Exp Med.*, 171(4):1375-1380, Apr. 1, 1990.
Villa-Komaroff et al., "A bacterial clone synthesizing proinsulin," *Proc Natl Acad Sci U S A.*, 75(8):3727-3731, Aug. 1978.
von Heijne, "Signal sequences. The limits of variation," *J Mol Biol.*, 184(1):99-105, Jul. 5, 1985.
Wagner et al., "Nucleotide sequence of the thymidine kinase gene of herpes simplex virus type 1," *Proc Natl Acad Sci U S A.*, 78(3):1441-1445, Mar. 1981.
Welch and Feramisco, "Rapid purification of mammalian 70,000-dalton stress proteins: affinity of the proteins for nucleotides," *Mol Cell Biol.*, 5(6):1229-1237, Jun. 1985.
Welch and Suhan, "Morphological study of the mammalian stress response: characterization of changes in cytoplasmic organelles, cytoskeleton, and nucleoli, and appearance of intranuclear actin fila

(56) References Cited

OTHER PUBLICATIONS ments in rat fibroblasts after heat-shock treatment," *J Cell Biol.*, 101(4):1198-1211, Oct. 1985.

Welch, "How cells respond to stress," *Sci Am.*, 268(5):56-64, May 1993.

Wigler et al., "Transformation of mammalian cells with an amplifiable dominant-acting gene," *Proc. Natl Acad Sci U S A.* 77(6):3567-3570, Jun. 1980.

William et al., "Revisiting stage IIIB and IV non-small cell lung cancer: analysis of the surveillance, epidemiology, and end results data," *Chest,* 136(3):701-709, Epub Mar. 24, 2009.

Williams et al., "Correlation between the induction of heat shock protein 70 and enhanced viral reactivation in mammalian cells treated with ultraviolet light and heat shock," *Cancer Res.,* 49(10):2735-2742, May 15, 1989.

Wolff et al., "Expression of retrovirally transduced genes in primary cultures of adult rat hepatocytes," *Proc Natl Acad Sci U S A,* 84(10):3344-3348, May 1987.

Yamazaki et al., "Application of secreted gp96 fusion protein (gp96-Ig) to immunogene therapy and cancer prevention," The Japan Lung Cancer Society, 40(5):388, Abstract B-29, Sep. 2000, 3 pages.

Yamazaki et al., Basic study of immunogene therapy by secretor-type gp96 fusion proteins (gp96-Ig), The Japan Lung Cancer Society, 41(5):527, Abstract P-20, Sep. 2001, 3 pages.

Yamazaki et al., "Effective therapeutic anti-tumor immunity generated by tumors secreting gp96-1g in FN syngeneic immunocompetent mice", 93rd Annual Meeting of the American Association of Cancer Research. Mar. 2002. Abstract #4821, 3 pages.

Yamazaki et al., "gp96 engineered for secretion of tumor peptides and for vaccination against cancer" *J Allergy Clin Immunol,* vol. 99, No. 1 Pt. 2, p. S45, Abstract 187, Jan. 1997.

Yang et al., "Cellular and humoral immune responses to viral antigens create barriers to lung-directed gene therapy with recombinant adenoviruses," *J Virol.,* 69(4):2004-2015, Apr. 1995.

Yanling Zhang, Hui Zhang, ed., Vaccinology, Beijing, science press, Mar. 2004, Version 1, ISBN 7-03-011586-4, paragraph 3 on p. 339 to the last paragraph on p. 343, [English translation], 19 pages.

Yu et al., "Coexpression of different antigenic markers on moieties that bear CA 125 determinants," *Cancer Res.,* 51(2):468-475, Jan. 15, 1991.

European Search Report and Opinion for Application No. EP09723235, dated Jun. 25, 2012, 7 pages.

International Preliminary Report on Patentability for PCT/US2009/001727, issued Sep. 21, 2010, 6 pages.

\* cited by examiner

SEQUENCE LISTING

<160> NUMBER OF SEQ ID NOS: 10

<210> SEQ ID NO 1
<211> LENGTH: 19
<212> TYPE: PRT

-continued

```
<213> ORGANISM: Homo sapiens

<400> SEQUENCE: 1

Met Asp Cys Thr Trp Arg Ile Leu Phe Leu Val Ala Ala Ala Thr Gly
1               5                   10                  15

Thr His Ala

<210> SEQ ID NO 2
<211> LENGTH: 19
<212> TYPE: PRT
<213> ORGANISM: Macaca mulatta

<400> SEQUENCE: 2

Met Lys His Leu Trp Phe Phe Leu Leu Leu Val Ala Ala Pro Arg Trp
1               5                   10                  15

Val Leu Ser

<210> SEQ ID NO 3
<211> LENGTH: 19
<212> TYPE: PRT
<213> ORGANISM: Callithrix jacchus

<400> SEQUENCE: 3

Met Asp Trp Thr Trp Arg Leu Phe Leu Leu Val Ala Thr Ala Thr Gly
1               5                   10                  15

Ala His Ser

<210> SEQ ID NO 4
<211> LENGTH: 19
<212> TYPE: PRT
<213> ORGANISM: Mus musculus

<400> SEQUENCE: 4

Met Lys Cys Ser Trp Val Ile Phe Phe Leu Met Ala Val Val Thr Gly
1               5                   10                  15

Val Asn Ser

<210> SEQ ID NO 5
<211> LENGTH: 19
<212> TYPE: PRT
<213> ORGANISM: Sus scrofa

<400> SEQUENCE: 5

Met Glu Phe Arg Leu Asn Trp Val Val Leu Phe Ala Leu Leu Gln Gly
1               5                   10                  15

Val Gln Gly

<210> SEQ ID NO 6
<211> LENGTH: 19
<212> TYPE: PRT
<213> ORGANISM: Rattus norvegicus

<400> SEQUENCE: 6

Met Lys Cys Ser Trp Ile Ile Leu Phe Leu Met Ala Leu Thr Thr Gly
1               5                   10                  15

Val Asn Ser

<210> SEQ ID NO 7
<211> LENGTH: 28
<212> TYPE: DNA
<213> ORGANISM: Artificial Sequence
```

```
<220> FEATURE:
<223> OTHER INFORMATION: synthetic PCR primer

<400> SEQUENCE: 7
attactcgag ggccgcacgc catgaggg                                              28

<210> SEQ ID NO 8
<211> LENGTH: 31
<212> TYPE: DNA
<213> ORGANISM: Artificial Sequence
<220> FEATURE:
<223> OTHER INFORMATION: synthetic PCR primer

<400> SEQUENCE: 8
gcccggatcc ttcagctgta gattcctttg c                                          31

<210> SEQ ID NO 9
<211> LENGTH: 34
<212> TYPE: DNA
<213> ORGANISM: Artificial Sequence
<220> FEATURE:
<223> OTHER INFORMATION: synthetic PCR primer

<400> SEQUENCE: 9
gcgaggatcc gtgcccaggg attctggttc taag                                       34

<210> SEQ ID NO 10
<211> LENGTH: 37
<212> TYPE: DNA
<213> ORGANISM: Artificial Sequence
<220> FEATURE:
<223> OTHER INFORMATION: synthetic PCR primer

<400> SEQUENCE: 10
ctaagcggcc gcaaggacac tgggatcatt taccagg                                    37
```

HEAT SHOCK PROTEIN GP96 VACCINATION AND METHODS OF USING SAME

RELATED APPLICATIONS

This application is the U.S. national phase of International Application No. PCT/US2009/001727 filed 19 Mar. 2009 which designated the U.S. and claims priority to U.S. Application No. 61/038,313, filed 20 Mar. 2008; the entire contents of each of which are hereby incorporated by reference.

GOVERNMENT SUPPORT

This invention was made with United States government support under grant numbers CA109094, CA039201 awarded by the National Institutes of Health and from ACGT. The United States Government may have certain rights in the invention.

FIELD OF THE INVENTION

The invention relates to the fields of medicine, immunology, and oncology. More specifically, the invention relates to methods and compositions for inducing an immune response against a tumor in an animal subject.

BACKGROUND

Antitumor vaccination is quite effective when administered to naive, tumor-free mice resulting in protection from tumor growth upon subsequent challenge. Protection is generally long lasting and tumor specific, indicating the participation of the adaptive immune response. This picture changes radically when vaccines are used for the therapeutic treatment of already established tumor. The same dose of vaccine that is able to effectively establish protective immunity is generally unable to provide therapeutic benefit. The reason for this lack of effectiveness of therapeutic vaccination is thought to stem from the induction of tumor-induced suppressor cells, the generation of regulatory cells, the induction of T-cell anergy or tolerance, or a combination of these mechanisms. Whatever the precise mechanisms of tumor-induced immune suppression, the success of vaccine therapy for cancer treatment will depend on overcoming or neutralizing these tumor-induced suppressive effects.

The heat shock protein (hsp) gp96, localized in the endoplasmic reticulum (ER), is thought to serve as a chaperon for peptides on their way to MHC class I and II molecules. Gp96-chaperoned peptides comprise the entire spectrum of peptides and larger protein fragments generated in cells and transported into the ER. Gp96 obtained from tumor cells and used as a vaccine induces specific tumor immunity, presumably through the transport of tumor-specific peptides to APCs. See J Immunol. 1999 Nov. 15; 163(10):5178-82.

The invention described in this application provides an antitumor composition. Heat shock protein glycoprotein (gp) 96-associated peptides are cross-presented to CD8 cells by dendritic cells. A vaccination system was developed suitable for antitumor therapy. See J Immunother. 2008 May; 31(4):394-401, and references cited therein. Transfecting a gp96-immunoglobulin (Ig) G1-Fc fusion protein into tumor cells results in the secretion of gp96-Ig in complex with chaperoned tumor peptides. Parenteral administration of gp96-Ig secreting tumors triggers robust, antigen specific CD8 cytotoxic T lymphocyte expansion combined with activation of the innate immune system. Tumor-secreted gp96 causes the recruitment of dendritic cells (DCs) and natural killer (NK) cells to the site of gp96 secretion and mediates DC activation via binding to CD91 and Toll-like receptor-2 and Toll-like receptor-4. The endocytic uptake of gp96 and its chaperoned peptides triggers peptide cross presentation via major histocompatibility complex (MHC) class I and strong, cognate CD8 activation independent of CD4 cells. In this model system, CD8 CTL expansion can be precisely quantitated within 4 to 5 days of vaccination by the use of adoptively transferred, T-cell receptor (TCR) transgenic, green fluorescent protein (GFP)-marked CD8 T cells.

SUMMARY

The invention provides a tumor cell genetically modified to express a nucleic acid encoding a secreted form of a heat shock protein (hsp) gp96 polypeptide. The invention also provides a method of stimulating an immune response to a tumor, including a cancer tumor by administering a tumor cell genetically modified to express a nucleic acid encoding a secreted form of a gp96 polypeptide. Preferably, the immune response is a protective immune response. Preferably, the tumor cell is an allogeneic tumor cell. The invention additionally provides a method of inhibiting a tumor, including cancer, by administering a tumor cell, for example a cancer tumor cell, genetically modified to express a secreted form of a gp96 polypeptide. Preferably, the tumor cell is an allogeneic tumor cell. The invention additionally provides a method of manufacturing a vaccine against cancer comprising genetically modifying a population of cancer cells to express a nucleic acid encoding tumor cells transfected with an eukaryotic expression vector comprising a nucleic acid encoding a secreted form of a heat shock protein (hsp) gp9 polypeptide. The invention additionally provides a method of a method of producing a protective immune response in a human subject comprising administering to the subject an effective amount of tumor cells transfected with an eukaryotic expression vector comprising a nucleic acid encoding a secreted form of a heat shock protein (hsp) gp96 polypeptide.

According to some preferred embodiments, gp96 polypeptide is a fusion protein comprising a gp96 polypeptide and an Immunoglobulin Signal Peptide (IgSP). Optionally, the IgSP is selected from the group consisting of mouse IgSP, rat IgSP, porcine IgSP, monkey IgSP, human IgSP.

According to some preferred embodiments, the gp96 immunization is administered frequently (e.g., daily or twice daily) for a period of from about 1 day to about 6 months. According to other preferred embodiments, the therapeutic composition is administered parenterally in a dosage of from 20 to 2000 mg per dose.

According to some preferred embodiments, the gp96 immunizations are administered in combination with a compound or compounds that destroys normal and/or malignant B lymphocytes, or compound or compounds used to treat diseases which are characterized by having too many B cells, overactive B cells, or dysfunctional B cells. Such diseases include a neoplastic disease such as leukemia or lymphoma. Preferably the B-cell destroying compound is an antibody. In certain embodiments the antibody is selected from a subhuman primate antibody, a murine monoclonal antibody, a chimeric antibody, a humanized antibody, and a human antibody. In other embodiments, the B-cell antigen that the antibody binds to is selected from CD19, CD20, CD22, HLA-DR and CD74.

DETAILED DESCRIPTION

Figure 1:
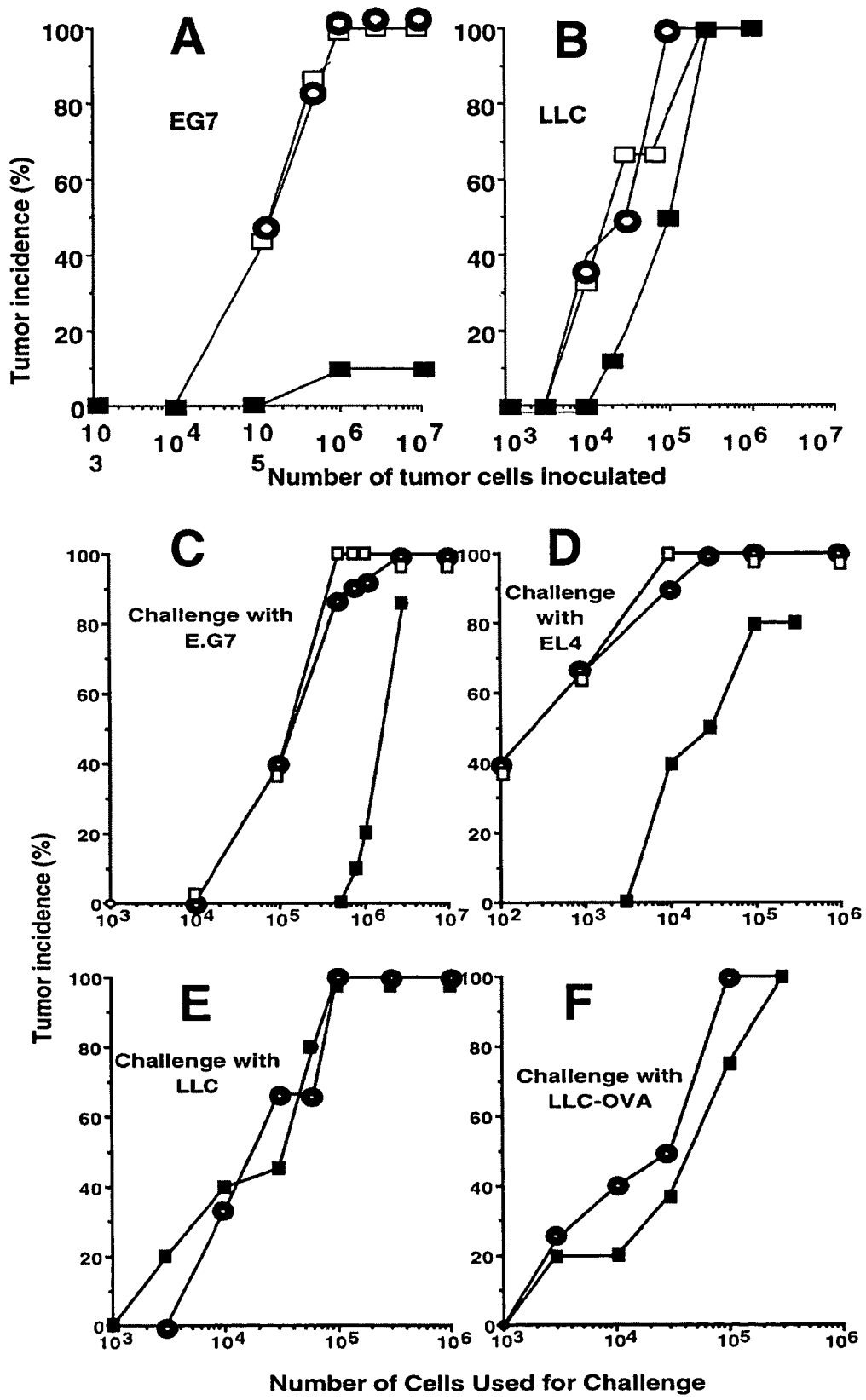
FIGS. 1A-F. Decreased tumorigenicity of gp96-Ig-transfected E.G7 (A) and LLC (B). ■, Gp96-Ig transfected; ○, mock transfected; and □, untransfected cells. Groups of six mice were used per dose of inoculated cells. C-F, Secretory gp96-Ig vaccination generates tumor-specific memory. C57BL/6 mice were immunized twice in biweekly intervals with $10^6$ gp96-Ig-transfected E.G7 (■ in all panels), with $10^6$ irradiated E.G7 (□), or not immunized (•). Two weeks later, mice were challenged (six mice per group) with the number of tumor cells indicated in the panels. Mice not developing tumors were observed for 3 months and then judged tumor free.

According to some preferred embodiments, the invention provides a method of producing a protective immune response in a human subject comprising administering to the subject an effective amount of tumor cells transfected with an eukaryotic expression vector comprising a nucleic acid encoding a secreted form of a heat shock protein (hsp) gp96 polypeptide.

According to some preferred embodiments, a method of manufacturing a vaccine against cancer comprising genetically modifying a population of cancer cells to express a nucleic acid encoding tumor cells transfected with an eukaryotic expression vector comprising a nucleic acid encoding a secreted form of a heat shock protein (hsp) gp96 polypeptide.

According to some preferred embodiments, the invention provides a method for stimulating an immune response to a tumor comprising administering to the subject an effective amount of tumor cells transfected with an eukaryotic expression vector comprising a nucleic acid encoding a secreted form of a heat shock protein (hsp) gp96 polypeptide.

According to preferred embodiments, the invention provides a method or inhibiting tumor growth comprising administering to the subject an effective amount of tumor cells transfected with an eukaryotic expression vector comprising a nucleic acid encoding a secreted form of a heat shock protein (hsp) gp96 polypeptide.

gp96 Polypeptides

Preferably the gp96 polypeptide is one of the wild type proteins, and preferably wild type human gp96 polypeptide. The gp96 polypeptides useful in this invention also include those gp96 polypeptides that have an amino acid sequence with substantial similarity or identity to the gp96 polypeptides set forth above. Preferably, the gp96 polypeptide used has at least 70%, more preferably 85%, still more preferably 90%, or still further preferably 95% identity or similarity to the gp96 polypeptides described herein or known in the art. Most preferably the gp96 polypeptide used has at least 99% similarity or identity to the wildtype human gp96 polypeptides.

The degree to which a candidate polypeptide shares homology with a gp96 polypeptide of the invention is determined as the degree of similarity or identity between two amino acid sequences.

A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity is determined by computer analysis, such as, without limitations, the ClustalX computer alignment program (Thompson J D, Gibson T J, Plewniak F, Jeanmougin F, & Higgins D G: "The ClustalX windows interface: flexible strategies for multiple sequence alignment aided by quality analysis tools"; Nucleic Acids Res. 1997, 25 (24): 4876-82), and the default parameters suggested therein. Using this program, the mature part of a polypeptide encoded by an analogous DNA sequence of the invention exhibits a degree of identity of at least 70%, more preferably 85%, still more preferably 90%, or still further preferably 95%, most preferably at least 99% with the amino acid sequences of the gp96 polypeptide sequences.

The gp96 polypeptides of the invention include variant polypeptides. In the context of this invention, the term "variant polypeptide" includes a polypeptide (or protein) having an amino acid sequence that differs from the wild type gp96 polypeptide at one or more amino acid positions. Such variant polypeptides include the modified polypeptides described above, as well as conservative substitutions, splice variants, isoforms, homologues from other species, and polymorphisms.

As defined herein, the term "conservative substitutions" denotes the replacement of an amino acid residue by another, biologically similar, residue. Typically, biological similarity, as referred to above, reflects substitutions on the wild type sequence with conserved amino acids.

For example, one would expect conservative amino acid substitutions to have little or no effect on the biological activity, particularly if they represent less than 10% of the total number of residues in the polypeptide or protein. Preferably, conservative amino acid substitutions represent changes in less than 5% of the polypeptide or protein, most preferably less than 2% of the polypeptide or protein.

The gp96 polypeptide in one embodiment comprises up to 15 amino acid substitutions. In another embodiment, the gp96 polypeptide comprises up to 12 amino acid substitutions. In another embodiment, the gp96 polypeptide comprises up to 10 amino acid substitutions. In another embodiment, the gp96 polypeptide comprises up to 8 amino acid substitutions. In another embodiment, the gp96 polypeptide comprises up to 5 amino acid substitutions. In a particularly preferred embodiment, there is a single amino acid substitution in the mature sequence, wherein both the substituted and replacement amino acid are non-cyclic. Other examples of particularly conservative substitutions include the substitution of one hydrophobic residue for another, such as isoleucine, valine, leucine or methionine, or the substitution of one polar residue for another, such as the substitution of arginine for lysine, glutamic for aspartic acid, or glutamine for asparagine, and the like.

The term conservative substitution also includes the use of a substituted amino acid residue in place of an un-substituted parent amino acid residue provided that antibodies raised to the substituted polypeptide also immunoreact with the un-substituted polypeptide.

Modifications of this primary amino acid sequence may result in proteins, which have substantially equivalent activity as compared to the unmodified counterpart polypeptide, and thus may be considered functional analogs of the parent proteins. Such modifications may be deliberate, e.g. as by site-directed mutagenesis, or they may occur spontaneously, and include splice variants, isoforms, homologues from other species, and polymorphisms. Such functional analogs are also contemplated according to the invention.

Signal Peptides

Signal peptides are enclosed in the coding part of the chromosomal DNA and are synthesized as part of the protein by the ribosomal apparatus. Signal peptides generally make up the N-terminal and cause the newly synthesized polypeptides to be directed into the rough endoplasmic reticulum. Here, the signal peptide is cleaved from the polypeptide and the mature protein is secreted into the surroundings. Thus, the signal peptide remains inside the cell.

Signal peptide-eukaryotic signal peptide. A eukaryotic signal peptide is a peptide present on proteins that are destined either to be secreted or to be membrane components. It is usually N-terminal to the protein. In the present context, all signal peptides identified in SignalP (version 2.0 or preferably version 3.0) are considered a signal peptide.

A mammalian signal peptide is a signal peptide derived from a mammalian protein secreted through the ER.

According to preferred embodiments of the present invention, a gp96 molecule is fused with a signal peptide (SP) to generate a gp96-SP fusion protein. The expression vector according to the invention comprises a nucleic acid comprising a promoter sequence capable of directing expression of a nucleotide sequence encoding a signal peptide operatively linked to a gp96 polypeptide.

The signal peptide may be any functional signal peptide, such as a heterologous signal peptide, such as an Immunoglobulin Signal Peptide. The signal peptide may be from any suitable species, such as human, mouse, rat, monkey, pig.

In some embodiments, the Immunoglobulin signal peptide (IgSP) is a small 19 amino acid peptide known from a large group of mammals. Preferably the IgSP is of mouse or human origin because the mouse IgSP is known to be functional in mouse, rat and human beings. For use in human beings, the IgSP preferably is of human origin in order to reduce the risk of any cross species side effect.

Preferably, the IgSp is one of more of the following: human IgSP (Met Asp Cys Thr Trp Arg Ile Leu Phe Leu Val Ala Ala Ala Thr Gly Thr His Ala; SEQ ID NO: 1); *Macaca mulatta* (monkey) IgSP (Met Lys His Leu Trp Phe Phe Leu Leu Leu Val Ala Ala Pro Arg Trp Val Leu Ser; SEQ ID NO: 2); *Callithrix jacchus* (monkey) IgSP (Met Asp Trp Thr Trp Arg Ile Phe Leu Leu Val Ala Thr Ala Thr Gly Ala His Ser; SEQ ID NO: 3); *Mus musculus* (mouse) IgSP (Met Lys Cys Ser Trp Val Ile Phe Phe Leu Met Ala Val Val Thr Gly Val Asn Ser; SEQ ID NO: 4); *Sus scrofa* (porcine) IgSP (Met Glu Phe Arg Leu Asn Trp Val Val Leu Phe Ala Leu Leu Gin Gly Val Gin Gly; SEQ ID NO: 5); and *Rattus norvegicus* (rat) IgSP (Met Lys Cys Ser Trp Ile Ile Leu Phe Leu Met Ala Leu Thr Thr Gly Val Asn Ser; SEQ ID NO: 6).

Cleavage of Signal Peptide: Before deciding on a specific gp96 form to incorporate into an expression construct, the likelihood of cleavage of the signal peptide, such as IgSP can be checked using state of the art prediction tools. One such preferred prediction tool is the SignalP software, which is available at the SignalP WWW server, or preferred, the newer version 3.0 available from the same server. In addition, there are several references describing the tools and techniques for selecting a signal peptide. These references include: Henrik Nielsen, Jacob Engelbrecht, Sren Brunak and Gunnar von Heijne: Identification of prokaryotic and eukaryotic signal peptides and prediction of their cleavage sites. Protein Engineering, 10, 1-6 (1997). For the SignalP-HMM output model: Henrik Nielsen and Anders Krogh: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998). Improved prediction of signal peptides—SignalP 3.0. Jannick Dyriv Bendtsen, Henrik Nielsen, Gunnar von Heijne and Sren Brunak. J M B (2004). Prediction of signal peptides and signal anchors by a hidden Markov model. Henrik Nielsen and Anders Krogh. Proceedings of the Sixth International Conference on Intelligent Systems for Molecular Biology (ISMB 6), AAAI Press, Menlo Park, Calif., pp. 122-130, 1998. Each of the above references are incorporated herein by reference in their entireties.

Administration

According to some preferred embodiments, the gp96 immunization is administered frequently (e.g., daily, twice daily, thrice daily, etc.) for a period of from about 1 day to about 6 months. According to some embodiments, the period of administration is from about 1 day to 90 days; from about 1 day to 60 days; from about 1 day to 30 days; from about 1 day to 20 days; from about 1 day to 10 days; from about 1 day to 7 days. According to some embodiments, the period of administration is from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

Combination Therapy

According to some preferred embodiments, the gp96 immunizations are administered in combination with a compound or compounds that destroys normal and/or malignant B lymphocytes, or compound or compounds used to treat diseases which are characterized by having too many B cells, overactive B cells, or dysfunctional B cells (e.g., Rituximab®). Such diseases include a neoplastic disease such as leukemia or lymphoma.

Preferably, the compound or compounds used to treat diseases which are characterized by having too many B cells, overactive B cells, or dysfunctional B cells are antibodies that target B cells. See e.g., U.S. Patent Publication No. 2003/0133930, incorporated herein by reference in its entirety. Preferably, antibodies that target B cells are antibodies to a B-cell antigen such as CD19, CD20, CD22, HLA-DR and CD74. Preferably, the therapeutic composition is administered parenterally in a dosage of from 20 to 2000 mg per dose. According to some embodiments, the subject receives the antibody in parenteral dosages. According to some embodiments, the subject receives the antibody in repeated parenteral dosages. According to some embodiments, the antibody is one of a subhuman primate antibody, murine monoclonal antibody, chimeric antibody, humanized antibody, and human antibody. According to some embodiments, the antibody is one of a murine, chimeric, or humanized antibody.

According to some preferred embodiments, the gp96 immunizations are administered in combination with one or more anticancer agents. Numerous types of anticancer agents are exemplary of those having applications in a method of the present invention. Such classes of anticancer agents, and their preferred mechanisms of action, are described below:

1. Alkylating agent: a compound that donates an alkyl group to nucleotides. Alkylated DNA is unable to replicate itself and cell proliferation is stopped. Examples of such compounds include, but are not limited to, busulfan, coordination metal complexes (e.g. platinum coordination compounds such as carboplatin, oxaliplatin, and cisplatin), cyclophosphamide (cytoxan), dacarbazine, ifosfamide, mechlorethamine (mustargen), and melphalan;

2. Bifunctional alkylating agent: a compound having two labile methanesulfonate groups that are attached to opposite ends of a four carbon alkyl chain. The methanesulfonate groups interact with, and cause damage to DNA in cancer cells, preventing their replication. Examples of such compounds include, without limitation, chlorambucil and melphalan.

3. Non-steroidal aromatase inhibitor: a compound that inhibits the enzyme aromatase, which is involved in estrogen production. Thus, blockage of aromatase results in the prevention of the production of estrogen. Examples of such compounds include anastrozole and exemstane.

4. Immunotherapeutic agent: an antibody or antibody fragment that targets cancer cells that produce proteins associated with malignancy. Exemplary immunotherapeutic agents include Herceptin which targets HER2 or HER2/neu, which occurs in high numbers in about 25 percent to 30 percent of breast cancers; Erbitux which targets the Epidermal Growth Factor Receptor (EGFR) in colon cancers; Avastin which targets the Vascular Endothelial Growth Factor (VEGF) expressed by colon cancers; and Rituxan an anti-CD20 antibody which triggers apoptosis in B cell lymphomas. Additional immunotherapeutic agents include immunotoxins, wherein toxin molecules such as ricin, diphtheria toxin and pseudomonas toxins are conjugated to antibodies, which recognize tumor specific antigens. Conjugation can be achieved biochemically or via recombinant DNA methods.

5. Nitrosurea compound: inhibits enzymes that are needed for DNA repair. These agents are able to travel to the brain so they are used to treat brain tumors, as well as non-Hodgkin's lymphomas, multiple myeloma, and malignant melanoma. Examples of nitrosureas include carmustine and lomustine.

6. Antimetabolite: a class of drugs that interfere with DNA and ribonucleic acid (RNA) synthesis. These agents are phase specific (S phase) and are used to treat chronic leukemias as well as tumors of breast, ovary and the gastrointestinal tract. Examples of antimetabolites include 5-fluorouracil, methotrexate, gemcitabine (GEMZAR®), cytarabine (Ara-C), and fludarabine.

7. Antitumor antibiotic: a compound having antimicrobial and cytotoxic activity. Such compounds also may interfere with DNA by chemically inhibiting enzymes and mitosis or altering cellular membranes. Examples include, but certainly are not limited to bleomycin, dactinomycin, daunorubicin, doxorubicin (Adriamycin), idarubicin, and the manumycins (e.g. Manumycins A, C, D, E, and G and their derivatives; see for example U.S. Pat. No. 5,444,087).

8. Mitotic inhibitor: a compound that can inhibit mitosis (e.g., tubulin binding compounds) or inhibit enzymes that prevent protein synthesis needed for reproduction of the cell. Examples of mitotic inhibitors include taxanes such as paclitaxel and docetaxel, epothilones, etoposide, vinblastine, vincristine, and vinorelbine.

9. Radiation therapy: includes but is not limited to X-rays or gamma rays which are delivered from either an externally supplied source such as a beam or by implantation of small radioactive sources.

10. Topoisomerase I inhibitors: agents, which interfere with topoisomerase activity thereby inhibiting DNA replication. Such agents include, without limitation, CPT-11 and topotecan.

11. Hormonal therapy: includes, but is not limited to anti-estrogens, such as Tamoxifen, GNRH agonists, such as Lupron, and Progestin agents, such as Megace.

Naturally, other types of anticancer agents that function via a large variety of mechanisms have application in the gp96 immunizations and methods of the present invention. Additional such agents include for example, leucovorin, kinase inhibitors, such as Iressa and Flavopiridol, analogues of conventional chemotherapeutic agents such as taxane analogs and epothilone analogues, antiangiogenics such as matrix metalloproteinase inhibitors, and other VEGF inhibitors, such as ZD6474 and SU6668. Retinoids such as Targretin can also be employed in the gp96 immunizations and methods of the invention. Signal transduction inhibitors that interfere with farnesyl transferase activity and chemotherapy resistance modulators, e.g., Valspodar can also be employed. Monoclonal antibodies such as C225 and anti-VEGFr antibodies can also be employed.

Types of Cancer

The term "tumor" is used to denote neoplastic growth which may be benign (e.g., a tumor which does not form metastases and destroy adjacent normal tissue) or malignant/cancer (e.g., a tumor that invades surrounding tissues, and is usually capable of producing metastases, may recur after attempted removal, and is likely to cause death of the host unless adequately treated) (see Steadman's Medical Dictionary, 26th Ed, Williams & Wilkins, Baltimore, Md. (1995)). As used herein, the terms "tumor", "tumor growth" or "tumor tissue" can be used interchangeably, and refer to an abnormal growth of tissue resulting from uncontrolled progressive multiplication of cells and serving no physiological function.

A solid tumor can be malignant, e.g. tending to metastasize and being life threatening, or benign. Examples of solid tumors that can be treated or prevented according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastric cancer, pancreatic cancer, breast cancer, ovarian cancer, fallopian tube cancer, primary carcinoma of the peritoneum, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) can be treated or prevented with gp96 immunizations or method of the present invention in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68 to 79). Hyperplasia is a form of controlled cell proliferation involving an increase in cell number in a tissue or organ, without significant alteration in structure or function. For example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated or prevented in accordance with a method of the present invention include arteriovenous (AV) malformations, particularly in intracranial sites and myelomas.

According to some embodiments, methods are provided for controlling solid tumor growth (e.g., breast, prostate, melanoma, renal, colon, cervical tumor growth) and/or metastasis comprising administering an effective amount of a compound of the invention to a subject in need thereof. In some embodiments, the subject is a mammal. In some embodiments, the mammal is human.

As used herein, the term "effective amount" of refers to an amount sufficient to provide the desired anti-cancer effect or anti-tumor effect in an animal, preferably a human, suffering from cancer. Desired anti-tumor effects include, without limitation, the modulation of tumor growth (e.g. tumor growth delay), tumor size, or metastasis, the reduction of toxicity and side effects associated with a particular anti-cancer agent, the amelioration or minimization of the clinical impairment or symptoms of cancer, extending the survival of the subject beyond that which would otherwise be expected in the absence of such treatment, and the prevention of tumor growth in an animal lacking any tumor formation prior to administration, i.e., prophylactic administration.

As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

"Synergistic effect", as used herein refers to a greater-than-additive anti-cancer effect which is produced by a combination of two drugs, and which exceeds that which would otherwise result from individual administration of either drug alone. One measure of synergy between two drugs is the combination index (CI) method of Chou and Talalay (see Chang et al., Cancer Res. 45: 2434-2439, (1985)), which is based on the median-effect principle. This method calculates the degree of synergy, additivity, or antagonism between two drugs at various levels of cytotoxicity. Where the CI value is less than 1, there is synergy between the two drugs. Where the CI value is 1, there is an additive effect, but no synergistic effect. CI values greater than 1 indicate antagonism. The smaller the CI value, the greater the synergistic effect. Another measurement of synergy is the fractional inhibitory concentration (FIC). This fractional value is determined by expressing the $IC_{50}$ of a drug acting in combination, as a function of the $IC_{50}$ of the drug acting alone. For two interacting drugs, the sum of the FIC value for each drug represents the measure of synergistic interaction. Where the FIC is less than 1, there is synergy between the two drugs. An FIC value of 1 indicates an additive effect. The smaller the FIC value, the greater the synergistic interaction.

The term "anticancer agent" as used herein denotes a chemical compound or electromagnetic radiation (especially, X-rays), which is capable of modulating tumor growth or metastasis. When referring to use of such an agent with a secreted form of a gp96 polypeptide, the term refers to an agent other than the secreted form of a gp96 polypeptide. Unless otherwise indicated, this term can include one, or more than one, such agents. Where more than one anticancer agent is employed, the relative time for administration of the secreted form of a gp96 polypeptide can, as desired, be selected to provide a time-dependent effective tumor concentration of one, or more than one, of the anticancer agents.

As used in this specification, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of either/or." In the specification and the appended claims, the singular forms include plural referents unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. As used in this specification, whether in a transitional phrase or in the body of the claim, the terms "comprise (s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Other Definitions

The compositions and methods of the invention are useful for stimulating an immune response against a tumor. Such immune response is useful in treating or alleviating a sign or symptom associated with the tumor. Such an immune response can ameliorate a sign or symptom associated with a lung cancer. As used herein, by "treating" is meant reducing, preventing, and/or reversing the symptoms in the individual to which a compound of the invention has been administered, as compared to the symptoms of an individual not being treated according to the invention. A practitioner will appreciate that the compositions and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc.

The methods of the invention can thus be used to treat a tumor, including, for example, a cancer. The methods of the invention can be used, for example, to inhibit the growth of a tumor by preventing further tumor growth, by slowing tumor growth, or by causing tumor regression. Thus, the methods of the invention can be used, for example, to treat a cancer such as a lung cancer. It will be understood that the subject to which a compound of the invention is administered need not suffer from a specific traumatic state. Indeed, the compounds of the invention may be administered prophylactically, prior to any development of symptoms (e.g., a patient in remission from cancer). The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a therapeutically effective amount of a composition of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the composition of the invention may be lowered or increased by fine tuning and/or by administering more than one composition of the invention (e.g., by the concomitant administration of two different genetically modified tumor cells), or by administering a composition of the invention with another compound to enhance the therapeutic effect (e.g., synergistically). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect. The methods of the invention can thus be used, alone or in combination with other well known tumor therapies, to treat a patient having a tumor. One skilled in the art will readily understand advantageous uses of the invention, for example, in prolonging the life expectancy of a lung cancer patient and/or improving the quality of life of a lung cancer patient.

A vaccination approach such as that disclosed herein can be an effective means of inducing immune response in patients with nonimmunogenic tumors.

Technical and scientific terms used herein have the meaning commonly understood by one of skill in the art to which the present invention pertains, unless otherwise defined.

The methods of the present invention are intended for use with any subject that may experience the benefits of the methods of the invention. Thus, in accordance with the invention, "subjects", "patients" as well as "individuals" (used interchangeably) include humans as well as non-human subjects, particularly domesticated animals.

As used herein, an "allogeneic cell" refers to a cell that is not derived from the individual to which the cell is to be administered, that is, has a different genetic constitution than the individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the individual to which the allogeneic cell is to be administered.

Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the individual to which the allogeneic cell is to be administered. Generally, the allogeneic cancer cell expresses one or more tumor antigens that can stimulate an immune response against a cancer in an individual to which the cell is to be administered, for example, a lung cancer.

As used herein, a "genetically modified cell" refers to a cell that has been genetically modified to express an exogenous nucleic acid, for example, by transfection or transduction.

As disclosed herein, an allogeneic whole cell vaccine may be chosen because whole cell vaccines have given good clinical results so far. Allogeneic cell-based vaccines offer a good alternative to autologous vaccines under the assumption that tumor antigens are shared in tumors of different patients, and the antigens can be cross-presented by the patients' antigen-presenting cells. See e.g., Fong, et al., Annu. Rev. Immunol. 18: 245-273 (2000); Boon, et al., Annu. Rev. Immunol. 12:337-365 (1994).

A composition of the invention containing a tumor cell genetically modified to express a secreted form of a gp96 polypeptide can be combined with a physiologically acceptable carrier useful in a vaccine by including any of the well known components useful for immunization. The components of the physiological carrier are intended to facilitate or enhance an immune response to an antigen administered in a vaccine. The formulations can contain buffers to maintain a preferred pH range, salts or other components that present the antigen to an individual in a composition that stimulates an immune response to the antigen. The physiologically acceptable carrier can also contain one or more adjuvants that enhance the immune response to the antigen. Formulations can be administered subcutaneously, intramuscularly, intradermally, or in any manner acceptable for immunization.

An adjuvant refers to a substance which, when added to an immunogenic agent of the invention such as tumor cell genetically modified to express a secreted form of a gp96 polypeptide, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, *mycobacterium* cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. Nature 344: 873-875 (1990). For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 8: 83(1988); Allison and Byars, in Vaccines: New Approaches to Immunological Problems, Ellis, ed., Butterworth-Heinemann, Boston (1992)). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., J. Clin. Oncol., 11: 390 (1993); Woodlock et al., J. Immunotherapy 22: 251-259 (1999)).

The compositions and methods of the invention disclosed herein are useful for treating a patient having a tumor. Although particular embodiments are exemplified with lung cancers, it is understood that a similar approach can also be used to treat other types of tumors, including cancers, using suitable allogeneic cells.

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLE 1

Tumor Secreted Heat Shock-Fusion Protein Elicits CD8 Cells for Rejection

The endoplasmic reticulum resident heat shock protein gp96 chaperons peptides, including those derived from tumor antigens, on their way to presentation by MHC class I. Replacement of the endoplasmic reticulum retention signal of gp96 with the Fc portion of murine IgG1 generated a secretory form of gp96, gp96-Ig. Tumor cells secreting gp96-Ig exhibited decreased tumorigenicity and increased immunogenicity in vivo and were rejected after initial growth. Rejection required CD8 T cells during the priming and effector phase. CD4 T cells were not required for rejection in either phase. Carrageenan, a compound known to inactivate macrophages in vivo, did not diminish CD8-mediated tumor rejection. Therefore, immunization with tumors secreting gp96-Ig generates efficient tumor-rejecting CD8 CTL without requirement for CD4 or macrophage help. In contrast, immunization with purified, tumor-derived gp96 or with irradiated tumor cells requires both.

A secretory form of gp96, gp96-Ig, was developed and tested it in tumor models. Transfection of tumor cells with the cDNA for gp96-Ig resulted in gp96-Ig secretion. As shown in this publication, gp96-Ig-secreting tumor cells caused powerful immunization and tumor rejection in vivo dependent exclusively on CD8 cells.

Cell Lines:

All cell lines were obtained from the American Type Culture Collection (Manassas, Va.) and cultured in medium with 10% FCS. Human small cell lung carcinoma (SCLC) cell lines (SCLC-2 and SCLC-7) were established as described in Savaraj et al., *Am. J. Clin. Oncol.* 20:398. Chicken OVA cloned into the expression vector, apc-NEO-OVA, was kindly provided by Dr. M. Bevan (Seattle, Wash.) and used to transfect Lewis lung carcinoma (LLC).

Construction of gp96-Ig: To generate the gp96-Ig fusion protein, the KDEL sequence was deleted and replaced with the hinge, CH2 and CH3 domains of murine; double-stranded cDNA was prepared from Jurkat DNA with the GeneAmp RNA PCR Kit (Perkin-Elmer Cetus, Norwalk, Conn.) and amplified by PCR. The PCR primers were 5'-ATTACTC-GAGGGCCGCACGCCATGAGGG-3' (SEQ ID NO: 7) and 5'-GCCCGGAT CCTTCAGCTGTAGATTCCTTTGC-3' (SEQ ID NO: 8). The PCR primers included an XhoI site (forward primer) and a BamHI site (reverse primer). The hinge, CH2 and CH3 domains of murine IgG1, was amplified by using murine IgG1 cDNA as a template and mutating the three cysteines of the hinge portion to serines. The PCR primers were 5'-GCGAGGATCCGTGCCCAGGGAT-TCTGGTTCTAAG-3' (SEQ ID NO: 9) and 5'-CTAAGCG-GCCGCAAGGACACTGGGATCATTTACCAGG-3' (SEQ ID NO: 10). The PCR primers included a BamHI site (forward primer) and NotI site (reverse primer). Gp96 was inserted into XhoI and BamHI sites of the eukaryotic expression vector, pBCMGSNeo and pBCMGHis, and transfected into SCLC-2, SCLC-7, B16F10, MC57, LLC NIH3T3, EL4, E.G7, and P815. Transfected cells were selected with 1 mg/ml of G4 18 or 2.5-10 mM of L-Histidinol (Sigma, St. Louis, Mo.). See J. Immunol. 1999 Nov. 15; 163(10):5178-82, and references cited therein.

ELISA:

This was conducted using antibodies to the Ig tag. Gp96-Ig-producing cells were plated at $10^6$/ml in AIMV or IMDM with 10% FCS, and culture supernatants were harvested at different time points. For analysis of intracellular expression of gp96-Ig, cells were lysed by three freeze-thaw cycles and centrifuged 60 min at 13,000×g.

Purification of Gp96-Ig Fusion Protein:

Gp96-Ig was purified by affinity chromatography on a protein A column using standard procedures (Bio-Rad, Hercules, Calif.). The concentration of gp96-Ig was determined by the Micro BCA protein assay reagent kit (Pierce, Rockford, Ill.). SDS-PAGE and Western blotting were done using a standard procedure.

FACS Analysis:

For membrane staining of gp96-Ig-transfected SCLC, cells were stained with goat anti-mouse IgG-FITC or goat anti-rabbit IgG-FITC as a control for 15 min at 4° C. and analyzed by a Becton Dickinson FACScan flow cytometer (San Diego, Calif.). For intracellular staining, cells were fixed with 4% paraformaldehyde and permeabilized with 1% saponin followed by staining with goat anti-mouse IgG-FITC, goat anti-mouse IgG-PE, goat anti-rabbit IgG-FITC, or goat anti-syrian hamster IgG-FITC for 15 min at 4° C. and analyzed by a flow cytometer.

Tumor inoculation and vaccination: Tumorigenicity in vivo was determined by s.c. injection of live tumor cells in 200 µl PBS into the flanks of mice. The size of tumors was measured in two dimensions twice weekly for at least 2 months. When mean tumor growth exceeded 10 mm diameter, the mice were sacrificed.

Mice were immunized by s.c. injection of $10^6$ live E.G7-gp96-Ig or irradiated E.G7 as a control (in 200 µl PBS), given in the right flank. Two immunizations at 2-wk intervals were given. Two weeks later, mice were challenged by s.c. injections of the indicated number of live tumor cells (EL4, E.G7, LLC, or LLC-OVA in 200 µl PBS) into the left flank.

Depletion of T Cells or Macrophages In Vivo:

A total of 100 µg of GK1.5 (anti CD4) or 2.43 (anti CD8) in 200 µl PBS was administered by i.p. injection. Depletion of CD4 and CD8 cells was verified by FACS analysis. CD4 or CD8 levels remained low (>95% depletion) for >2 wk following Ab injection (data not shown). For functional inhibition of macrophages, 1 mg of Carrageenan (type II; Sigma) in 200 µl PBS was administered by i.p. injection.

Results:

The ER-resident hsp gp96 purified from tumor cells can provide tumor-specific immunity. The C-terminal sequence KDEL of gp96 serves as ER retention signal. Deletion of this sequence resulted in the secretion of gp96 together with bound peptides from transfected tumor cells and may render tumors more immunogenic to allow tumor rejection by the immune system.

Replacing the KDEL sequence of gp96 with the hinge, CH2 and CH3 domain of murine IgG1, an Ig isotype inefficient in Fc receptor binding, and transfection of the cDNA into tumor cells resulted in the secretion of gp96-Ig into the culture supernatant, where it was quantitated by ELISA. Protein A purified gp96-Ig upon SDS-PAGE migrated with a major band of the predicted molecular mass of 120 kDa for the fusion protein and two minor, higher molecular bands previously reported also for unmodified gp96. Western blotting with a mAb specific for gp96 confirmed the identity of the fusion protein. Only the major band is stained, suggesting that the minor bands are glycosylation variants of gp96 not recognized by the Ab.

Secretion of gp96-Ig resulted in its time-dependent, linear accumulation in the supernatant. Intracellular gp96-Ig was detected at a low and constant steady-state level in lysates of transfected cells, indicating that it does not accumulate in the cell. FACS analysis of membrane-intact, transfected tumor cells revealed no staining with anti-mouse IgG above background, indicating that the Ig moiety of the fusion protein is not displayed on the outer leaflet of the plasma membrane. In contrast, upon permeabilization of the membrane, gp96-Ig is detected intracellularly with a goat anti-mouse IgG Ab, but not by control goat anti-rabbit IgG Abs. The transmembrane domain of gp96 does not interfere with the secretion of gp96-Ig and does not lead to intracellular accumulation. These data are consistent with previous reports suggesting that the transmembrane domain is not used for anchoring of gp96 in the membrane and that gp96 is not an integral membrane protein. Altmeyer et al., 1996 *Int. J. Cancer* 69:340.

All murine and human cell lines transfected with gp96-Ig secreted the fusion protein. Mock-transfected cells did not secrete gp96-Ig. E.G7 is an OVA transfectant of the EL4 lymphoma forming lethal tumors in syngeneic C57BL/6 mice. Gp96-Ig transfection of E.G7 allows the determination whether E.G7-gp96-Ig immunizes$^{against}$ the EL4 parent tumor in addition to E.G7, the OVA surrogate$^{antigen}$-transfected tumor. As second tumor, LLC transfected with gp96-Ig or with OVA was used because, in contrast to E.G7, it is a nonhemopoietic, low-immunogenic tumor. Both cell lines secrete comparable amounts of gp96-Ig.

Secreted Gp96-Ig is Responsible for Decreased Tumorigenicity:

Secretion of gp96-Ig decreases the tumorigenicity of E.G7 in C57BL/6 mice by >100-fold when compared with mock-transfected or untransfected E.G7. Subcutaneous inoculation of 10 million hsp-secreting tumor cells caused tumors in only 10% of the inoculated mice (FIG. 1A). A similar reduction of tumorigenicity by gp96-Ig secretion was observed with transfected EL4 (data not shown). Gp96-Ig secretion by LLC resulted in a more moderate, ~5-fold, decrease of tumorigenicity (FIG. 1B).

To determine immunogenicity and immune memory responses, C57BL/6 mice were immunized twice at 2-wk intervals with a dose of nonirradiated E.G7-gp96-Ig ($10^6$) that was rejected. Subsequently, they were challenged with untransfected or mock-transfected E.G7, parental EL4, untransfected LLC, and OVA-transfected LLC (FIG. 1, C-F). Mice immunized with irradiated E.G7 or unvaccinated mice served as controls. E.G7-gp96-Ig-immunized mice resisted a 10-fold higher tumor challenge by E.G7 than mice vaccinated with irradiated cells or unimmunized mice (FIG. 1C). Tumor growth in vaccinated mice was frequently delayed. The effect of immunization was even more pronounced when challenged with EL4, allowing a fifty-fold dose increase of EL4 challenge compared with the controls (FIG. 1D). As expected, E.G7-gp96-Ig immunization offered no protection against challenge with untransfected or vector-transfected LLC (FIG. 1E), while a moderate, ~3-fold, increase in protection was observed when OVA-transfected LLC were used as challenge (FIG. 1F). The strong protection of mice immunized with E.G7-gp96-Ig against EL4 challenge may be due to multiple tumor antigens shared by E.G7 and EL4. The weak protection$^{against}$ challenge with LLC-OVA depends on T cells recognizing a single or limited number of epitopes derived from the OVA surrogate$^{antigen}$ for T cell recognition.

CD8 Cells are Required in the Priming and Effector Phase:

The involvement of immune mechanisms in the rejection of E.G7-gp96-Ig was further examined by in vivo depletion/inactivation of immunocompetent cells. It has been reported that Meth A tumor-derived gp96 requires CD4 cells, CD8 cells, and macrophages for effective immunization, while immunization with irradiated Meth A tumor cells required CD4 and CD8 cells but no macrophages.

For priming one million unirradiated, live E.G7-secreting gp96-Ig were inoculated s.c. This dose is sufficient to establish tumors that grow to a mean diameter of about 8 mm, subsequently shrink, and are rejected. Tumor rejection is blocked in mice treated with the anti-CD8 Ab 2.43, either 2 days before (FIG. 2A) or up to 3 days after tumor inoculation (not shown). The anti-CD4 Ab GK1.5 had no effect on tumor rejection (FIG. 2A) regardless of time of injection, even though it completely depleted CD4 cells for >14 days (data not shown). CD4-deficient mice were able to reject E.G7-gp96-Ig (FIG. 2B), supporting the importance of CD8 cells. E.G7 not secreting gp96-Ig forms tumors in untreated and immune-depleted mice. Carrageenan, known to inactivate macrophages in vivo, had no effect on tumor rejection.

Figure 2:
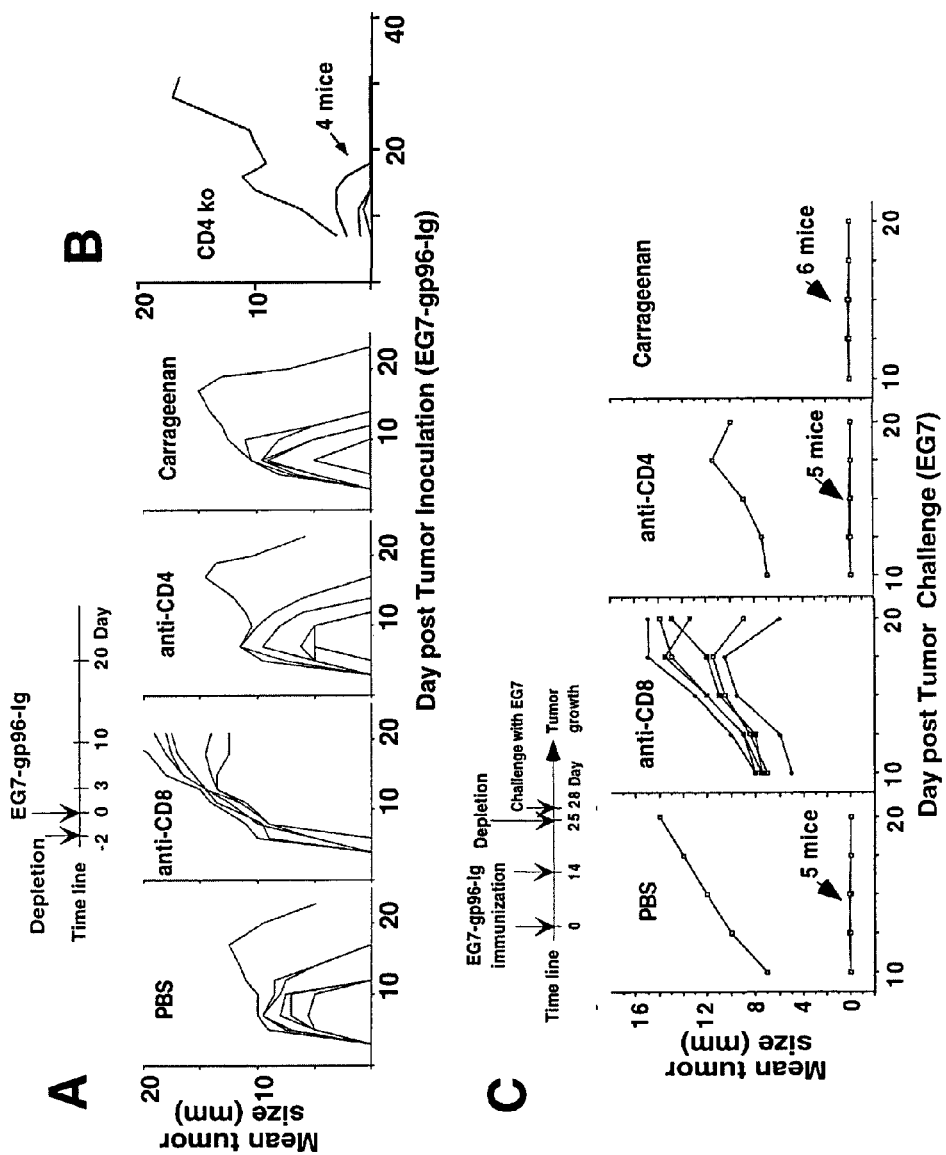
FIGS. 2A-C. A, Effect of depletion of immunocompetent cells on the rejection of $10^6$ E.G7-gp96-Ig during the priming phase; controls received PBS. Tumor growth curves of individual mice are shown. The depletion schedule is shown schematically on top. Depletion of immunocompetent cells was done with anti-CD8, anti-CD4, or Carrageenan 2 days prior to inoculation of $10^6$ E.G7-gp96-Ig. B, CD4-deficient mice can reject E.G7-gp-Ig. Five CD4-deficient mice were challenged with unirradiated $10^6$ E.G7-gp96-Ig s.c. Tumor growth was recorded, and the mean tumor diameter is reported. C, Effect of depletion of immunocompetent cells on the effector phase of E.G7 rejection. The schedule of immunization and immunodepletion is shown schematically on the top. For immunization, $10^6$ unirradiated E.G7-gp96-Ig were inoculated twice s.c. into groups of six mice. Three days prior to challenge with $10^6$ E.G7, immune cells were depleted as above; controls received PBS. Tumor growth was recorded and is reported as mean tumor diameter.

To study the effector phase of tumor rejection, mice were immunized twice at 14-day intervals with live E.G7-gp96-Ig. Eleven days later (day 25), immune cells were depleted, and after 3 days the mice were challenged with untransfected E.G7. Only CD8 cells are required in the effector phase; depletion of CD4 cells or Carrageenan inactivation of macrophages had no influence on E.G7 rejection in the effector phase (FIG. 2C).

Deletion of the endoplasmic retention signal of gp96 and replacement with the Fc portion if IgG1 readily results in the secretion of gp96-Ig, which appears to be dimerized through the IgG1 hours chain. E.G7-secreted gp96 is able to provide long-lasting specific immunity, suggesting that it chaperons tumor peptides. In contrast, irradiated or mock-transfected E.G7 are not able to provide protective immunity. *Corynebacterium parvum* also failed to serve as adjuvant for E.G7 immunization. Secreted gp96-Ig provides immunologic specificity for both the surrogate antigen OVA and other EL4 antigens, but does not cross-immunize to LLC-derived tumor antigens.

The data are consistent with the explanation that peptides associated with secreted gp96-Ig are transferred to and presented by class I MHC and stimulate a tumor-specific CD8$^+$ CTL response causing tumor rejection. The CD8 response appears to be independent of CD4 help and does not require macrophages. Whether the cellular requirements are due to gp96-Ig dimerization is not known.

It is instructive to compare the mechanisms of immunization by purified tumor-derived gp96 and by tumor-secreted gp96-Ig. Udono et al., (*Proc. Natl. Acad. Sci. USA* 91:3077, 1994), using gp96 purified from Meth A tumor cells for immunization, reported a requirement for CD8 cells and macrophages in the priming phase and a requirement for CD4 and CD8 cells as well as macrophages in the effector phase of tumor rejection of Meth A tumors. Immunization with irradiated Meth A tumors required CD4 cells in the priming phase, and both CD4 and CD8 cells in the effector phase. Irradiated EG7 do not produce immunity$^{against}$ subsequent challenge. The dramatic effect of tumor-secreted gp96-Ig is entirely dependent on CD8 cells without CD4 help. CD8 cells are required in the priming and effector phase of the CTL response to the tumor. Macrophages appear not to be needed. The role of dendritic cells or other APCs in the presentation of gp96-chaperoned peptides to CD8 cells is not known, but remains a possibility. It is also possible that gp96-Ig-secreting EG7 stimulate CD8 cells directly.

EXAMPLE 2

Molecular and Cellular Requirements for Enhanced Antigen Cross-Presentation to CD8 Cytotoxic T Lymphocytes This example demonstrates that tumor-secreted heat shock protein gp96-chaperoned peptides enhance the efficiency of antigen cross-priming of CD8 CTL by several million-fold over the cross-priming activity of unchaperoned protein alone. Gp96 also acts as adjuvant for cross-priming by unchaperoned proteins, but in this capacity gp96 is 1000-fold less active than as a peptide chaperone. Mechanistically, the in situ secretion of gp96-Ig by transfected tumor cells recruits and activates dendritic cells and NK cells to the site of gp96 release and promotes CD8 CTL expansion locally. Gp96-mediated cross-priming of CD8 T cells requires B7.1/2 costimulation but proceeds unimpeded in lymph node-deficient mice, in the absence of NKT and CD4 cells and without CD40L. Gp96-driven MHC I cross-priming of CD8 CTL in the absence of lymph nodes provides a novel mechanism for local, tissue-based CTL generation at the site of gp96 release. This pathway may constitute a critically important, early detection, and rapid response mechanism that is operative in parenchymal tissues for effective defense against tissue damaging antigenic$^{agents.}$ Heat shock proteins are chaperone peptides that can be taken up by APCs and cross-presented to CD8 cells. Exogenous heat shock protein (HSP) are actively captured by CD91 and LOX-1 on dendritic cells (DC) and elicit peptide-specific immune responses by delivering the chaperoned peptide to the MHC class I pathway to be cross-presented to CD8$^+$ CTL. Cross-priming by HSP-gp96 is associated with TLR2 and TLR4 stimulation and DC maturation resulting in a CD8 CTL-biased response.

Immunization with gp96-secreting tumor cells generated tumor-specific and surrogate antigen-specific immunity that was independent of CD4 cells. Oizumi et al. J Immunol. 2007 Aug. 15; 179(4):2310-7. Using this immunization method to quantitate CD8 responses this example shows that minute, femtomolar amounts of gp96-chaperoned antigen are sufficient for cognate CD8 cross-priming locally at the site of gp96 release independent of lymph nodes and CD4 cells.

Mice:

Wild-type (wt) and B7.1, B7.2, B7.1/2, CD40L, lymphotoxin α(LTα), and CD4-deficient mice in the C57BL/6 (B6) background were obtained from The Jackson Laboratory. B6.Jα281$^{-/-}$ mice (NKT deficient, renamed Jα18 knockout (ko)) were provided by Dr. M. Lotze (University of Pittsburgh Medical Center, Pittsburgh, Pa.) with permission from Dr. Taniguchi (Chiba University, Chiba, Japan). GFP-transgenic mice were obtained by permission of the producers. C57BL/6 OT-I mice were obtained from Dr. M. Bevan (University of Washington School of Medicine, Seattle, Wash.). All mice were used at 6-12 wk of antigene.

Cell Lines:

EG7, the OVA-transfected EL4 lymphoma line, generously provided by Dr. M. Bevan, was further transfected with the vector pCMG-His containing gp96-Ig as described previously. NIH 3T3 cells were transfected with OVA in pAC-neo-OVA (generously provided by Dr. M. Bevan) and with pCMG-His containing gp96-Ig.

Antibodies:

Fluorescent antibodies were purchased from BD Pharmingen and eBioscience.

Purification and Adoptive Transfer of OT-I Cells:

GFP-marked OT-I cells were purified by positive selection with anti-CD8 using magnetic separation (>95% pure; Miltenyi Biotec). One million GFP-OT-I cells were adoptively transferred through tail veins of C57BL/6 mice in a volume of 0.3 ml of PBS.

Immunization:

Two days after adoptive transfer of GFP-OT-I, 2-4×10$^6$ nonirradiated EG7-gp96-Ig cells or control EG7 cells were injected i.p. in a volume of 0.5 ml of PBS. For some experiments, mice were immunized i.p. with 3T3-OVA-gp96-Ig, 3T3-OVA, or intact OVA (Sigma-Aldrich) dissolved in PBS.

Ex Vivo Ag Cross-Presentation and Cross Priming of OT-1:

Groups of B6 wt mice were i.p. immunized with 2×10$^6$ 3T3-OVA-gp96-Ig or 3T3-gp96-Ig. After 3 days peritoneal exudate cells (PEC) were collected and 10$^5$ PEC were cocultured with purified, naive CFSE-labeled OT-I at different ratios (5:1, 10:1, 100:1, and 1000:1) for 48 and 72 hours in round-bottom 96-well microtiter plates in 200 µl of tissue culture medium. CFSE-labeled OT-I were also cocultured directly with 3T3, 3T3-OVA-gp96-Ig and 3T3-gp96-Ig. After the indicated period of time, cells were collected and stained with anti-CD8-PE. OT-I expansion was measured by CFSE dilution as analyzed in an LSR II flow cytometer (BD Biosciences). Cell division was analyzed by CFSE dilution in gated lymphocytes or in total CFSE$^+$ cells and expressed as the percentage of total CFSE$^+$ cells.

BrdU Labeling and Analysis:

Mice were administered BrdU (Sigma-Aldrich) in their drinking water (0.8 mg/ml) at the time of immunization. Cell samples were analyzed by staining for BrdU (eBioscience) after fixation and permeabilization.

CD4 Cells Inhibit Ag Cross Presentation to CD8 CTL by HSP Gp96-Peptide:

Tumor cells transfected with a secretable form of gp96, gp96-Ig, become immunogenic and induce tumor-specific immunity in mice. Yamazaki et al., J. Immunol. 163: 5178-5182 (1999). Tumor immunity required CD8 cells but was independent of CD4 cells in either the afferent or efferent arm of the immune response.

Because CD4 cells express both helper cell and regulatory cell activity, we were interested to determine whether any of these opposing functions regulated cross-priming of CD8 cells by gp96. We used adoptively transferred K$^{b-OVA}$-specific TCR-transgenic CD8 cells, OT-I, to quantitate CTL expansion in response to EG7-gp96-Ig or EG7 immunization i.p. EG7 is the OVA-transfected EL4 lymphoma. OT-I expansion in this system has previously been shown to be dependent on gp96-chaperoned OVA peptides and not to be influenced by the Ig-Fc-tag because gp96-myc was equally active. The tumor-secreted gp96-Ig immunization system also generates immunity to genuine tumor antigens. However, measuring OT-I expansion provides a more precise and rapid readout than measuring tumor rejection.

Figure 3:
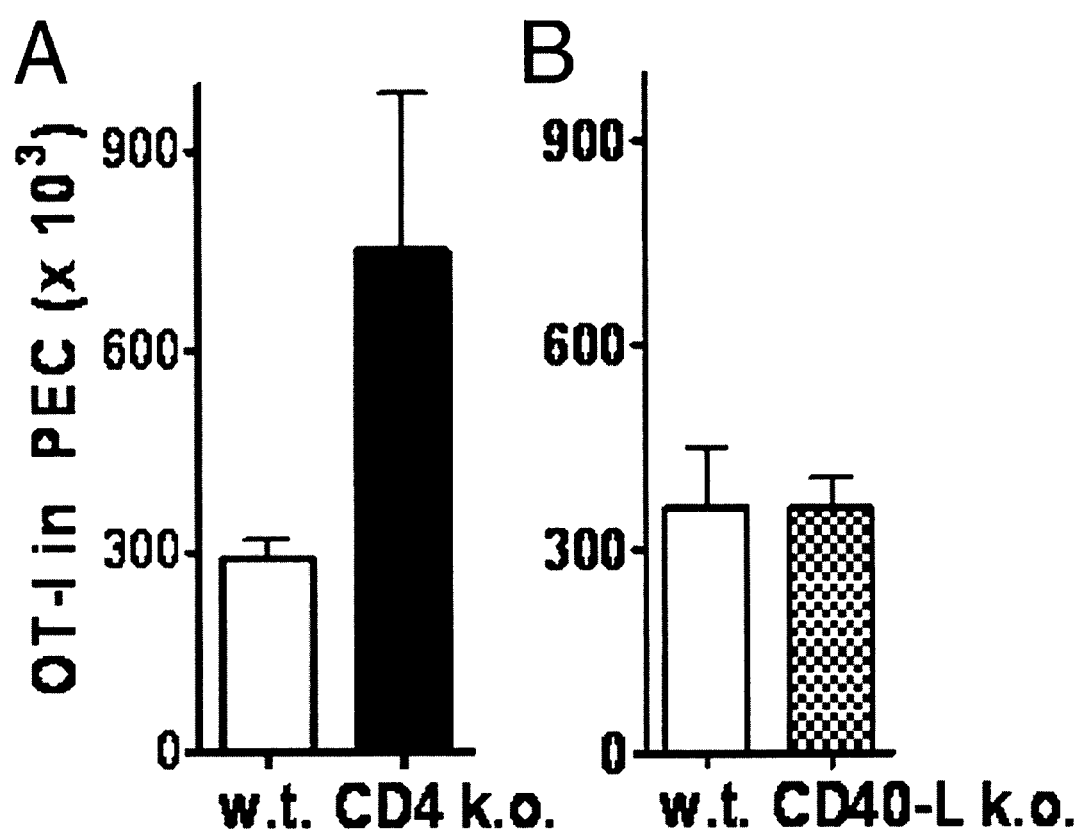
FIGS. 3A-B. Gp96-mediated cross-priming of CD8 T cells is enhanced in the absence of CD4 cells but not affected by the absence of CD40L. Mice received 1 million GFP-OT-I i.v. and were immunized 2 days later i.p. with 4 million EG7-gp96-Ig. Cells were harvested from the peritoneal cavity (PC) after 5 additional days and analyzed for GFP-OT-I frequency in the CD8 gate by FACS. Values are expressed as absolute numbers of GFP-OT-I in the PC. A, CD4-deficient mice compared with wt mice. B, CD40L-deficient mice.

In CD4 ko, all CD4 functions (helper and regulatory) are deleted, whereas in CD40L ko primarily the helper cell function of CD4 cells is missing. We therefore compared OT-I expansion in response to gp96-OVA secreted by EG7-gp96 in CD4 ko and in CD40L ko vs wt mice (FIG. 3). To facilitate analysis, OT-I TCR-transgenic cells were also GFP-marked (GFP-OT-I) by breeding OT-I mice with GFP-transgenic mice. In comparison to wt mice, OT-I expansion in CD4 ko mice was increased by 100% in response to EG7-gp96-Ig, suggesting that the presence of CD4 cells interferes with CD8 clonal expansion (FIG. 3A). In contrast, in CD40L ko mice OT-I expansion was similar to the expansion in wt mice (FIG. 3B). The data indicate that CD4 helper function mediated via CD40L is not required for gp96-mediated antigen cross-presentation to CD8 CTL. CD4$^+$ T regulatory cells in contrast, absent in CD4 ko, normally down-regulate OT-I cross-priming by gp96-OVA.

CD8 Cross Priming by Gp96 is Dependent on B7.

1 and B7.2 and independent of NKT cells: Efficient T cell priming requires DC maturation and up-regulation of MHC and costimulatory molecules, frequently mediated through CD40 signals. However, CD4 help via the CD40L/CD40 axis clearly is not needed for gp96-mediated OT-I priming (FIG.

Figure 4:
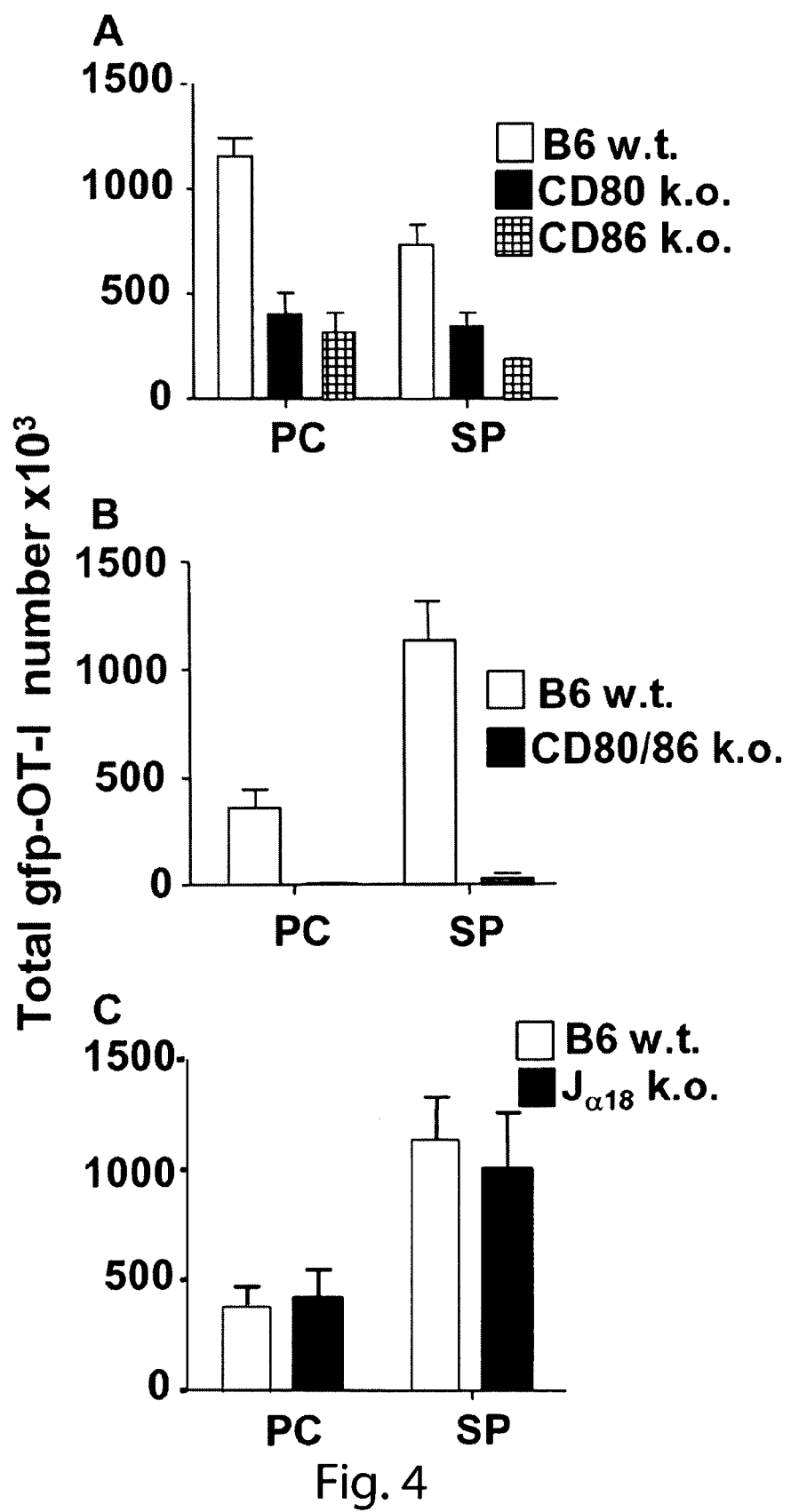
FIGS. 4A-C. Gp96-mediated cross-priming of CD8 T cells requires CD80 and CD86 and is independent of NKT cells. Mice received 1 million GFP-OT-I i.v. and were immunized 2 days later i.p. with 4 million EG7-gp96-Ig (A and C) or 2 million 3T3-OVA-gp96-Ig (B). Cells were harvested from the spleen (SP) or the PC after 5 additional days and analyzed for GFP-OT-I frequency in the CD8 gate by FACS. A, CD80 or CD86 single deficiency; B, CD80/CD86 double deficiency; and C, NKT deficiency ($J_{\alpha 18}$ ko).

3). Gp96 binds to CD91 and to TLR2 and TLR4 and thereby may be able to activate DC independent of CD40. We determined whether this mechanism of cross-priming of CD8 cells in vivo relied on B7.1 (CD80) and B7.2 (CD86) costimulation. Mice deficient either for B7.1 or B7.2 alone (FIG. 4A) were able to costimulate gp96-mediated cross-priming of OT-I at ~50% efficiency of wt mice. However, in the complete absence of both, B7.1 and B7.2, in double-deficient mice (FIG. 4B), gp96-mediated cross-priming of OT-I was completely abolished.

NKT cells are frequently involved in antitumor immunity. $J_{\alpha 18}$ ko mice lack NKT cells due to their inability to generate the invariant TCR $v_{\alpha 14}$ chain characteristic for CD1d-restricted invariant NKT cells. The ability of $J_{\alpha 18}$ ko mice to support undiminished OT-I expansion (FIG. 4C) suggests that NKT cells are not essential for gp96-mediated OT-I cross-priming.

Figure 5A:
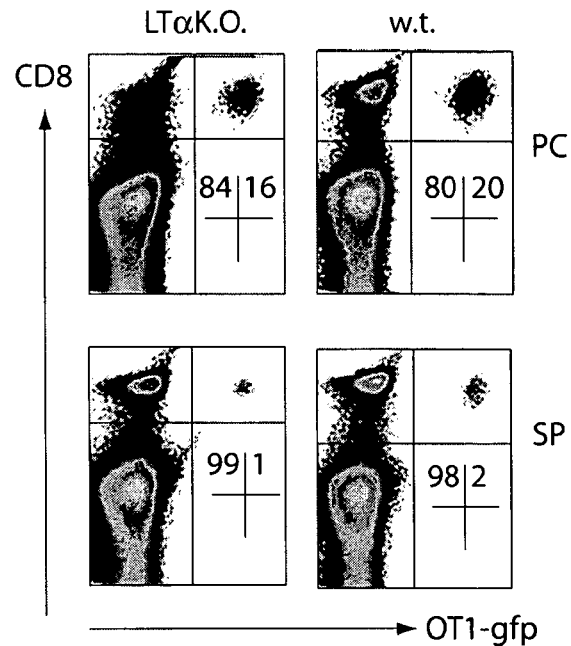
FIGS. 5A-C. Efficient cross-priming by gp96 in the absence of lymph nodes. A, LTα deficiency, representative FACS data. Mice received 1 million GFP-OT-I i.v. and were immunized 2 days later i.p. with 2 million 3T3-OVA-gp96-Ig. Cells were harvested from the indicated sites after 5 additional days and were analyzed for GFP-OT-I frequency in the CD8 gate by FACS. B, Same data presented as histograms. Data are representative of two independent experiments, each bar represents the mean±SE of two mice. C, Ex vivo cross-priming of OT-I by 3T3-OVA-gp96-Ig. PEC harvested from mice injected i.p. 3 days earlier with 3T3-OVA-gp96-Ig, 3T3-gp96-Ig, or 3T3 were incubated with CFSE-labeled OT-I for 72 hours at ratios of 1:10, 1:100, and 1;1000 OT-I:PEC (a-f). As additional controls, 3T3 transfectants were also incubated directly with OT-I in vitro. Cells were stained with anti-CD8-PE and analyzed for CFSE dilution, which is plotted in b-h.
Figure 5B:
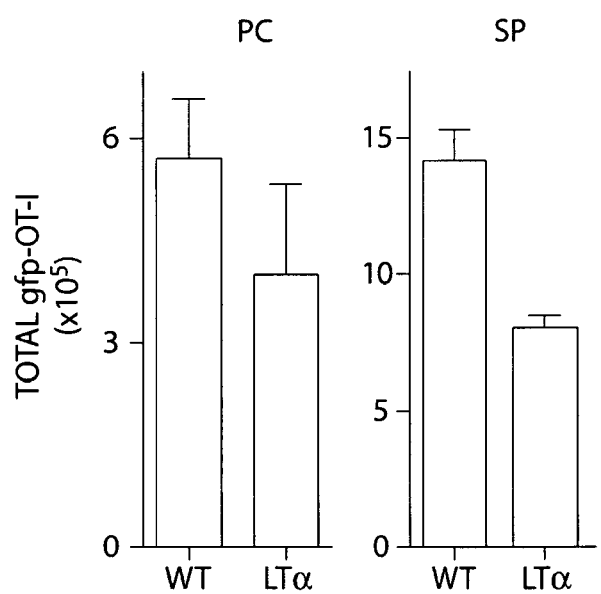

Ag Cross Presentation by Gp96 does not Require Lymph Nodes:

Draining lymph nodes bring together APCs, CD4 helper cells, CD8 CTL precursors and NK cells, promote cellular interactions, and enhance CTL priming and expansion. Because gp96-mediated$^{antigen}$ cross-priming is independent of CD4 help, we raised the question of the requirement for draining lymph nodes for OT-I expansion. LTα-deficient mice lack peripheral and mesenteric lymph nodes, including Peyer's patches, and are impaired in antiviral responses. However, when analyzed for gp96-OVA-mediated OT-I expansion, LTα-deficient mice showed almost normal OT-I expansion in the peritoneal cavity (PC) when compared with wt mice (FIGS. 5, A and B). In the spleen, the accumulation of GFP OT-I was diminished by ~50%, reflecting the absence of lymph node-based OT-I clonal expansion. This finding suggested that lymph nodes are not essential for gp96-mediated peptide cross-priming and that local cross-priming takes place at the site of gp96 release.

Figure 5C:
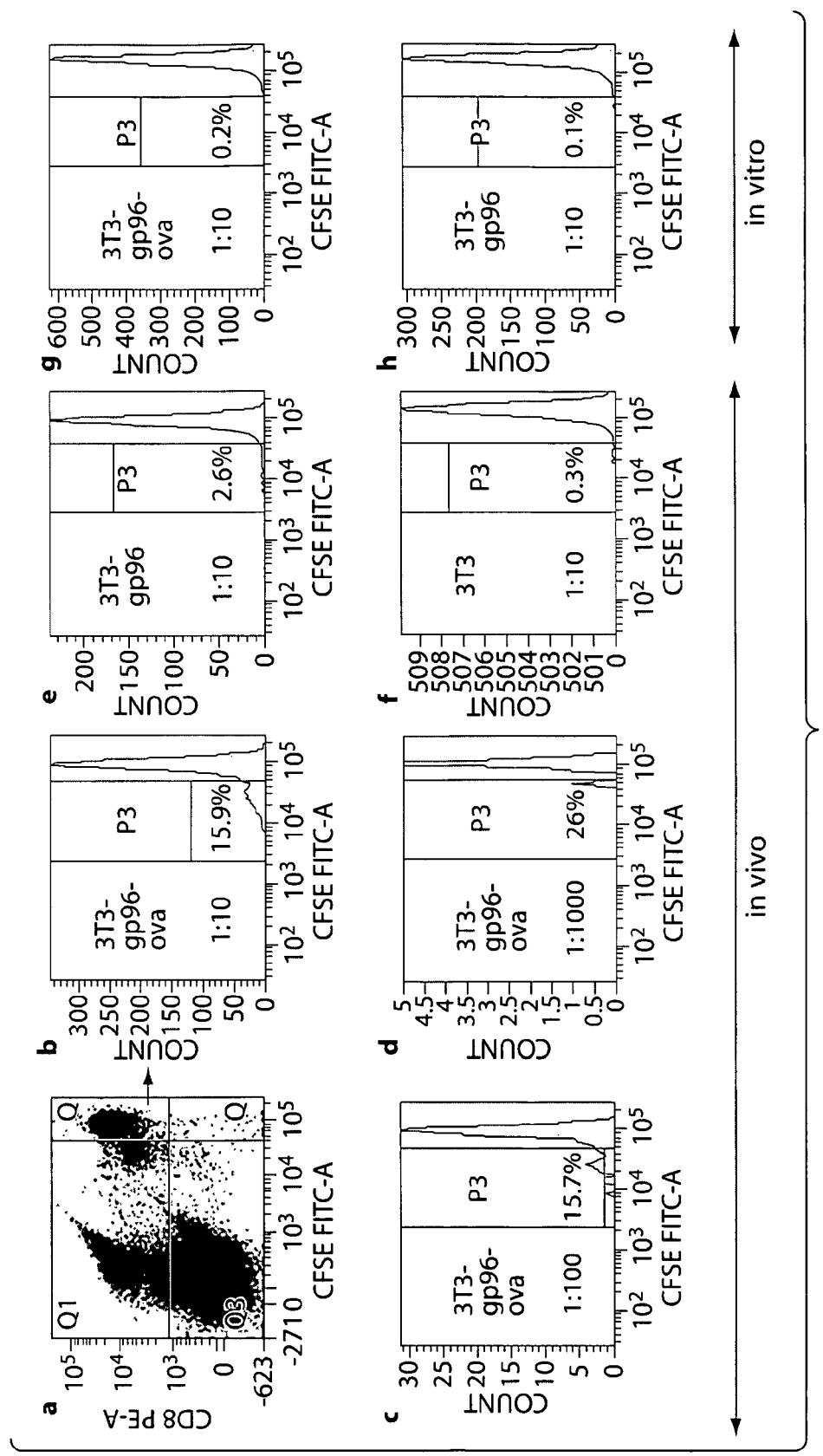

To test lymph node-independent cross-priming of OT-I directly, we isolated PEC from B6 mice on day 3 after i.p. immunization with allogeneic 3T3 cells, 3T3-OVA cells, or 3T3-OVA-gp96-Ig cells. The PEC were mixed at various ratios with CFSE-labeled OT-I and CFSE dilution determined 48 and 72 hours later. PEC isolated from mice injected with 3T3-OVA-gp96-Ig were able to cross-prime OT-I in vitro (FIG. 5, C, a-d) as indicated by CFSE dilution. In contrast, PEC isolated from mice injected with 3T3-gp96 or untransfected 3T3 were unable to stimulate OT-I proliferation (FIG. 5c, e, f). Likewise, direct in vitro incubation of CSFE-labeled OT-I with 3T3-OVA-gp96-Ig or with 3T3-gp96-Ig was unable to cause CSFE dilution. The data support the model of gp96-OVA-induced antigen cross-presentation to cognate CD8 cells in the absence of lymph nodes in the PC.

Gp96 Recruits DC and NK Cells to the Site of its Release and Causes their Activation:

Cross-priming at minimum requires the bringing together of APCs and CD8 cells, while CD4 cells are not essential in our model system. We determined whether the local release of gp96 in the PC caused local recruitment and activation of APCs and OT-I, thereby bypassing the need for lymph nodes.

OT-I expansion upon gp96-Ig immunization is maximal by days 4 and 5 and is most pronounced in the PC. Starting from essentially 0, ~0.5 million OT-I accumulate on days 4 and 5 in the PC, representing up to 60% of the recruited CD8 cells. Strong OT-I expansion is highly dependent on gp96-Ig secretion (FIG. 6) and is minimal in response to EG7, as also observed by others. The ability of gp96 to cross-prime CD8 cells within 4 days in wt mice suggests early activation of APCs and other innate cells. It is known that gp96 is able to activate and mature DC in vitro and that gp96-chaperoned peptides are cross-presented by MHC I on DC and macrophages in vitro and in vivo. Oizumi et al. J Immunol. 2007 Aug. 15; 179(4):2310-7. It has also been reported that gp96 is able to activate NK cells. Oizumi et al. J Immunol. 2007 Aug. 15; 179(4):2310-7. The fact that unimpaired OT-I activation takes place in LTAα ko mice suggested that cell recruitment and activation must take place locally at the site of gp96 release.

Figure 7:
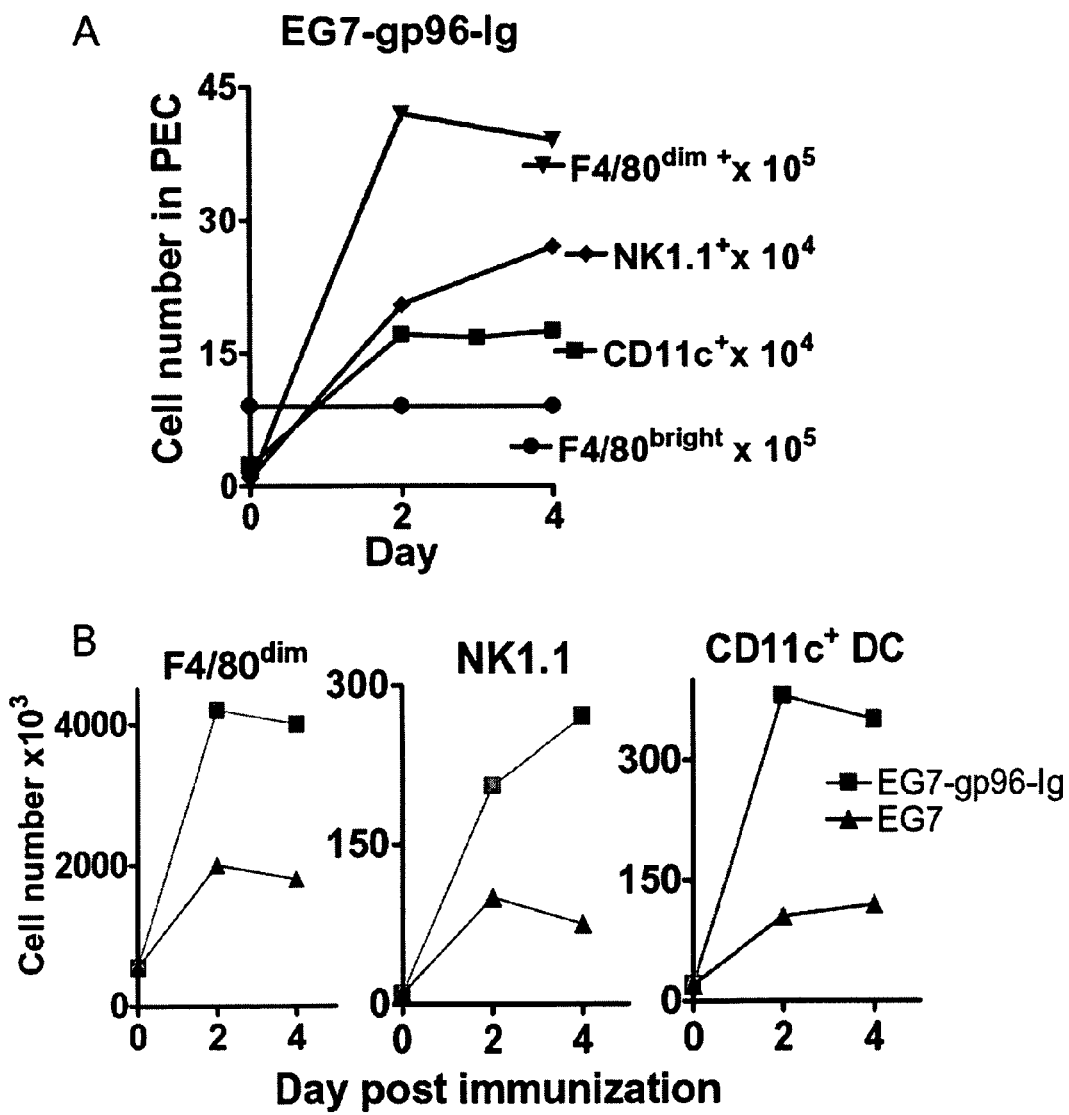
FIGS. 7A-B. Increased recruitment of innate immune cells into the PC by gp96. One million OT-1 were transferred i.v. on day −2 and 2 days later 4 million EG7 or EG7gp96-Ig cells were injected i.p. Cells were harvested from the PC on the days indicated and phenotyped by flow cytometry. A, Recruitment of CD11c$^+$, NK1.1$^+$, and F4/80$^{dim}$ cells by injection of EG7-gp96-Ig. F4/80$^{bright}$ cells are present in the PC before immunization and do not change in number after immunization. B, Comparison of cell recruitment into the PC by EG7 and EG7-gp96-Ig.
Figure 8:
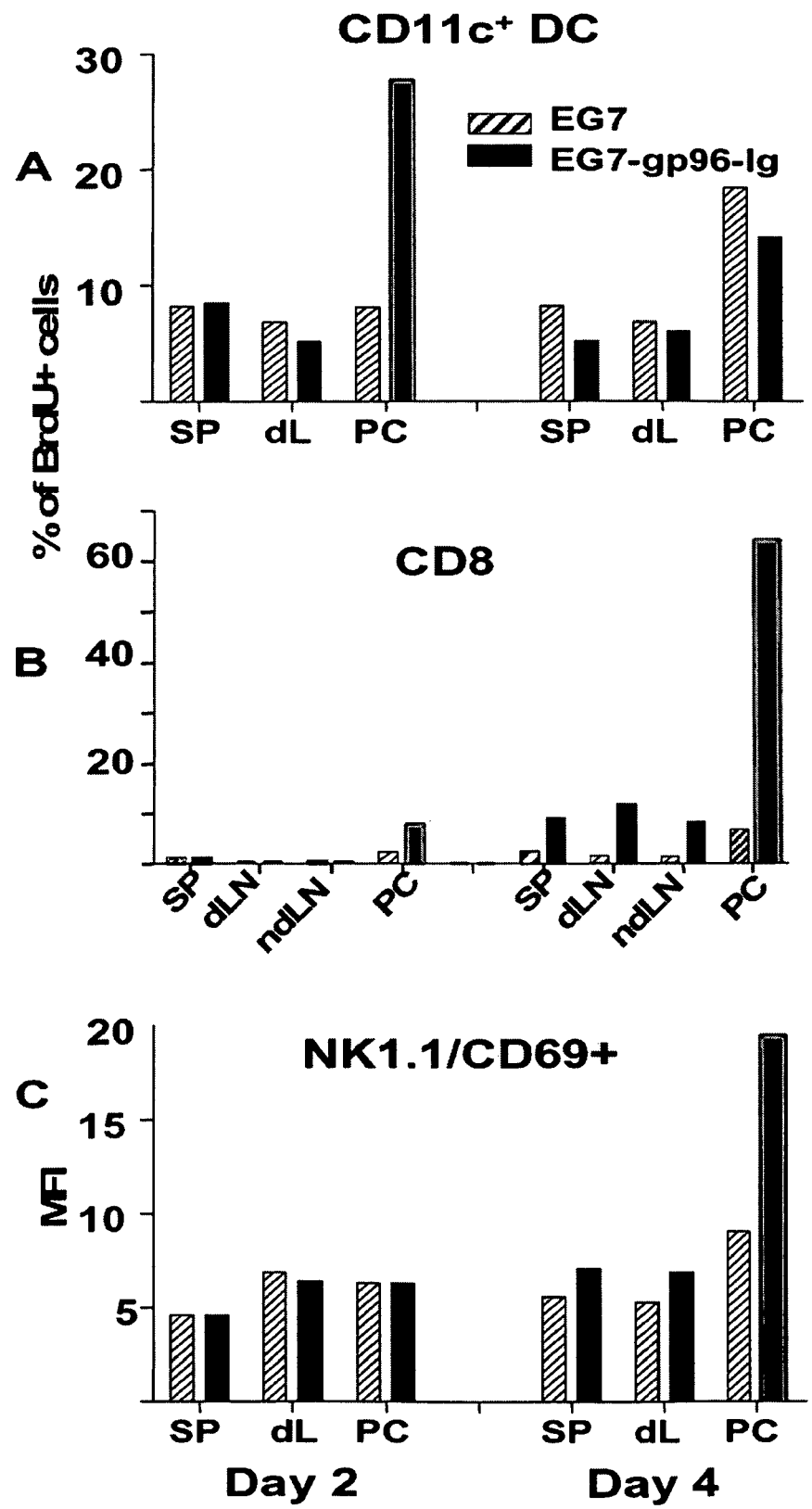
FIGS. 8A-C. Gp96 secretion mediates proliferation of DC and CD8 cells and activates NK cells in the PC. Mice received 1 million GFP-OT-I i.v. and were immunized 2 days later i.p. with 4 million EG7-gp96-Ig or EG7. A, Proliferation of CD11c$^+$ cells measured by BrdU staining in the PC, mesenteric, and para-aortic lymph nodes (dL) and spleen (SP) 2 and 4 days after immunization with 4×10$^6$ EG7 or EG7-gp96-Ig. CD11c$^+$ cells were gated and analyzed for BrdU by intracellular staining. Note CD11c$^+$ proliferation (red lined) on day 2 only in the PC and only after EG7-gp96-Ig administration. Mice received BrdU in the drinking water from the day of immunization. B, CD8 proliferation measured by BrdU uptake is detectable only in the PC on day 2 (red lined) and only after gp96 priming. Strong CD8 proliferation on day 4 in the PC after EG7-gp96-Ig immunization; dLN, draining lymph node (para-aortic, mesenteric); ndLN, nondraining lymph node (inguinal). C, Activation of NK1.1 cells in the PC by EG7-gp96-Ig immunization as measured by CD69 up-regulation. A-C are representative of three independent experiments.

Following i.p. injection of EG7-gp96-Ig, or EG7 as control, PEC were harvested on days 1-4 and analyzed for activation by phenotype and by the uptake of BrdU. The largest fraction of EG7-gp96-Ig-recruited cells, ~80-90%, were $F4/80^{dim}$ monocyte/macrophages. Resident peritoneal macrophages present before immunization were $F4/80^{bright}$ and did not change in number following EG7-gp96-Ig injection. CD11c$^+$ DC and NK1.1$^+$ NK cells each constituted ~5-10% of the cells recruited within the first 2 days into the PC. B cells and CD4 T cells were found in increasing numbers in the PC beginning on day 3 and further increased on days 4 and 5 (data not shown). In comparison to EG7, i.p. injection of EG7-gp96-Ig doubled the number of total cells recruited into the PC within the first 2 days (FIG. 7A). This effect required the secretion of at least 60 ng of gp96-Ig by the injected cells within 24 h, as measured by ELISA. Oizumi et al. J Immunol. 2007 Aug. 15; 179(4):2310-7. If lower amounts of gp96-Ig were secreted by the number of injected cells, the effect on cell recruitment and CD8 cross-priming quickly tapered off, suggesting that there is a threshold level of sensitivity for stimulation of cross-priming (data not shown). Gp96 secretion by EG7 doubled the total number of recruited $F4/80^{dim}$ cells and tripled the number of DC and NK cells over EG7 not secreting gp96-Ig (FIG. 7B). DC recruited into the PC by gp96 within the first 2 days incorporated significant amounts of BrdU, indicating their activation. DC isolated from draining para-aortic lymph nodes, mesenteric lymph nodes, and spleen in contrast were BrdU negative (FIG. 8A). This finding strongly suggests that DC are activated and proliferate locally of at the site of gp96 secretion. Only later are BrdU-positive DC also found in lymph nodes and spleen. EG7, not secreting gp96, did not cause BrdU uptake by DC in the PC within the first 2 days. Interestingly however, EG7 recruited DC were weakly BrdU positive on day 4 (FIG. 8A), indicating delayed and weak activation by EG7 in contrast to early and strong activation by EG7-gp96. The delayed DC activation by the wt tumor EG7 is associated with only minimal CD8 expansion.

CD8 cells present in the PC by day 2 in the EG7-gp96-Ig group showed significant BrdU uptake, while at the same time CD8 cells in draining lymph nodes and spleen remained BrdU negative (FIG. 8B). This finding is consistent with local, peritoneal initiation of CD8 proliferation rather than in lymph nodes. By day 4, gp96-dependent BrdU uptake by CD8 cells in the PC was very pronounced and still significantly higher than in lymph nodes or spleen (FIG. 8B).

NK cells in the gp96 group but not in the EG7 group were activated by day 4 as indicated by CD69 (FIG. 8C) and 2B4 (data not shown) up-regulation. NK activation, as measured by CD69 up-regulation, only occurred in PEC (FIG. 8C) and not in lymph nodes or spleen (data not shown), antigenain suggesting local activation.

These data demonstrate that local gp96 release in the PC is able to transmit signals that result in the local recruitment and activation of innate and adaptive immune cells, providing a cellular mechanism for CD8 cross-priming independent of lymph nodes and CD4 cells. This cross-priming mechanism is not dependent on the specific anatomy of the PC, because s.c. administration of EG7-gp96-Ig or 3T3-OVA-gp96-Ig is equally effective in OT-I cross-priming (data not shown).

Figure 6:
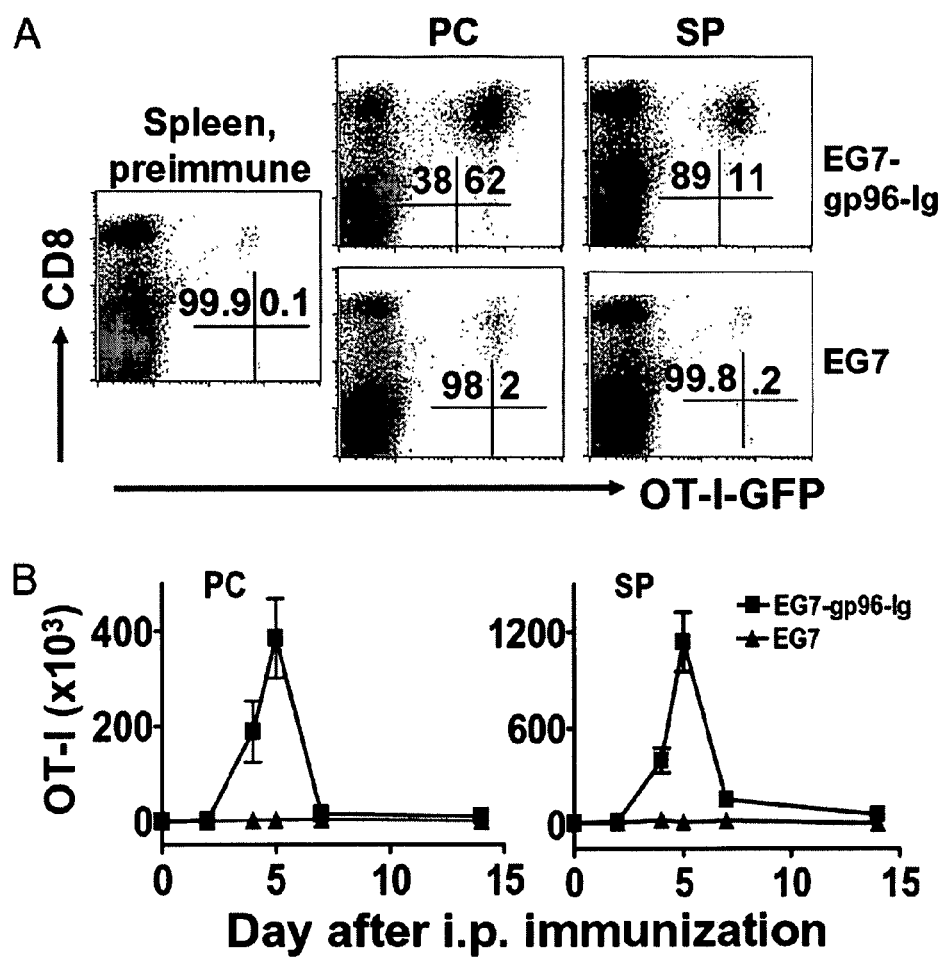
FIGS. 6A-B. Cross-priming of CD8 T cells by gp96-OVA is more efficient than direct priming by antigen presentation through EG7-$K^{b-OVA}$. Mice received 1 million GFP-OT-I i.v. and were immunized 2 days later i.p. with 2 million EG7-gp96-Ig or EG7. A, Cells were harvested from the PC before immunization (preimmune) and 5 days after immunization and analyzed for GFP-OT-I frequency in the CD8 gate by FACS. B, Kinetics of GFP-OT-I expansion in the PC and spleen after EG7-gp96-Ig and EG7 immunization; total number of GFP-OT-I at the given site is plotted.

Highly Efficient CD8 CTL Cross Priming by Gp96-Chaperoned Peptides:

Secretion of gp96-Ig by EG7-gp96-Ig results in a dramatic increase in OT-I expansion when compared with EG7 even though both cell lines secrete comparable quantities of OVA (~80 ng/24 hours×10$^6$ cells) (FIG. 6). Similar differences in OT-I expansion are seen when OT-I expansion is compared in response to allogeneic 3T3-OVA and 3T3-OVA-gp96-Ig. Oizumi et al. J Immunol. 2007 Aug. 15; 179(4):2310-7. Gp96-Ig secreted from OVA-transfected cells contains a small fraction (~0.1% or less) of gp96 molecules that chaperone OVA peptides (gp96-OVA) and these are thought to be responsible for OT-I cross-priming. However, secreted gp96 may also act as nonspecific adjuvant for the recruitment and activation of DC and thereby enhance uptake and cross-priming of OVA protein. Finally, it is possible that gp96-Ig and OVA protein are secreted as separate molecules and form gp96-Ig-OVA complexes extracellularly. Several experiments were conducted to distinguish between these possibilities.

Figure 9:
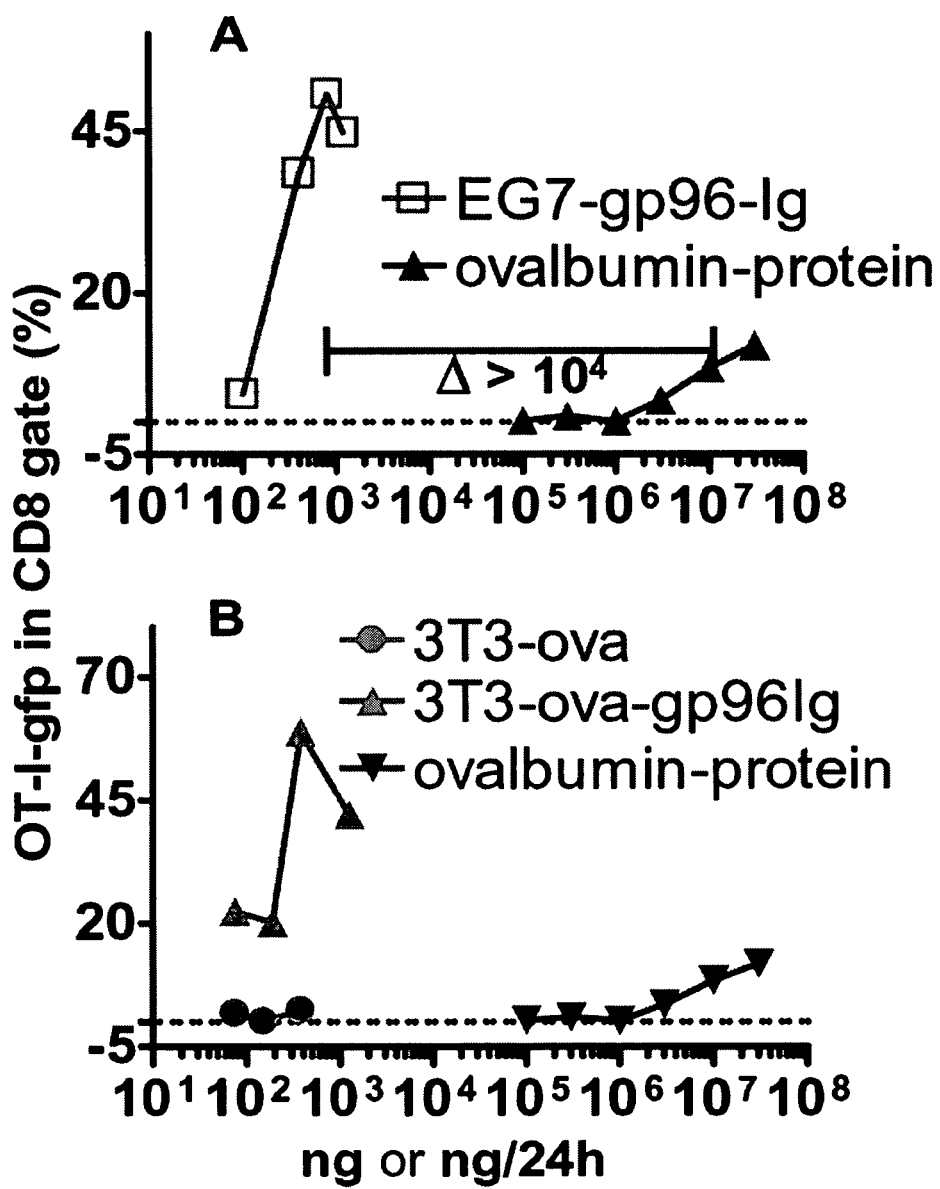
FIGS. 9A-B. Enhanced CD8 T cells cross-priming by gp96-chaperoned OVA compared with free OVA protein. C57BL/6 mice received 1 million GFP-OT-I i.v.; 2 days later they were immunized i.p. with different numbers of syngeneic EG7-gp96-Ig or allogeneic 3T3-OVA or 3T3-OVA-gp96-Ig or with OVA protein in PBS. The number of cells for i.p. injection was adjusted to yield the quantity of secreted gp96-Ig or OVA in 24 hours as indicated on the x-axis. OVA and gp96-Ig secretion, respectively, was determined in vitro by ELISA. GFP-OT-I expansion was determined on day 5 after immunization in the PC by flow cytometry. A, GFP-OT-I expansion in response to EG7-gp96-Ig and to OVA protein. B, GFP-OT-I expansion in response to 3T3-OVA, to 3T3-OVA-gp96-Ig and to OVA protein.

First, we compared dose-response profiles of the efficiency of OT-I expansion in the PC and spleen after i.p. injection of 3T3-OVA, 3T3-OVA-gp96-Ig, or EG7, EG7gp96-Ig and pure OVA protein (FIG. 9). The rate of secretion of OVA and of gp96-Ig, respectively, was determined in vitro by ELISA as nanograms secreted per 24 h. By injecting different cell numbers, a dose range of secreted OVA and gp96-Ig was achieved as shown in FIG. 9. OT-I expansion was measured 4 days after stimulation. 3T3-OVA cells, secreting only OVA at a rate of 80-800 ng per 24 h, were unable to expand OT-I. Clearly, this quantity of OVA is unable to cross-prime OT-I even in the presence of allogeneic activation of the immune system. Similarly, syngeneic EG7 cells secreting OVA alone expand OT-I only minimally (FIG. 6) even though EG7 cells express $K^{b-OVA}$, suggesting that direct priming of OT-I is very inefficient. In contrast, when gp96 is secreted from OVA-containing tumor cells, 80-800 ng per 24 hours of gp96 efficiently cross-prime OT-I and result in their expansion locally and in the spleen. Efficient OT-I cross-priming by OVA-protein in contrast required 3-10 mg protein. The difference in sensitivity of OT-I expansion in response to OVA protein vs gp96 secreted from OVA-containing cells is ~10,000-fold (FIG. 9) in terms of weight. Taking into account molecular weights and the fact that maximally 0.1% of secreted gp96 molecules are associated with OVA peptides, the difference in OT-I cross-priming activity by gp96-OVA vs OVA protein is about 20 million-fold in molar terms.

Figure 10:
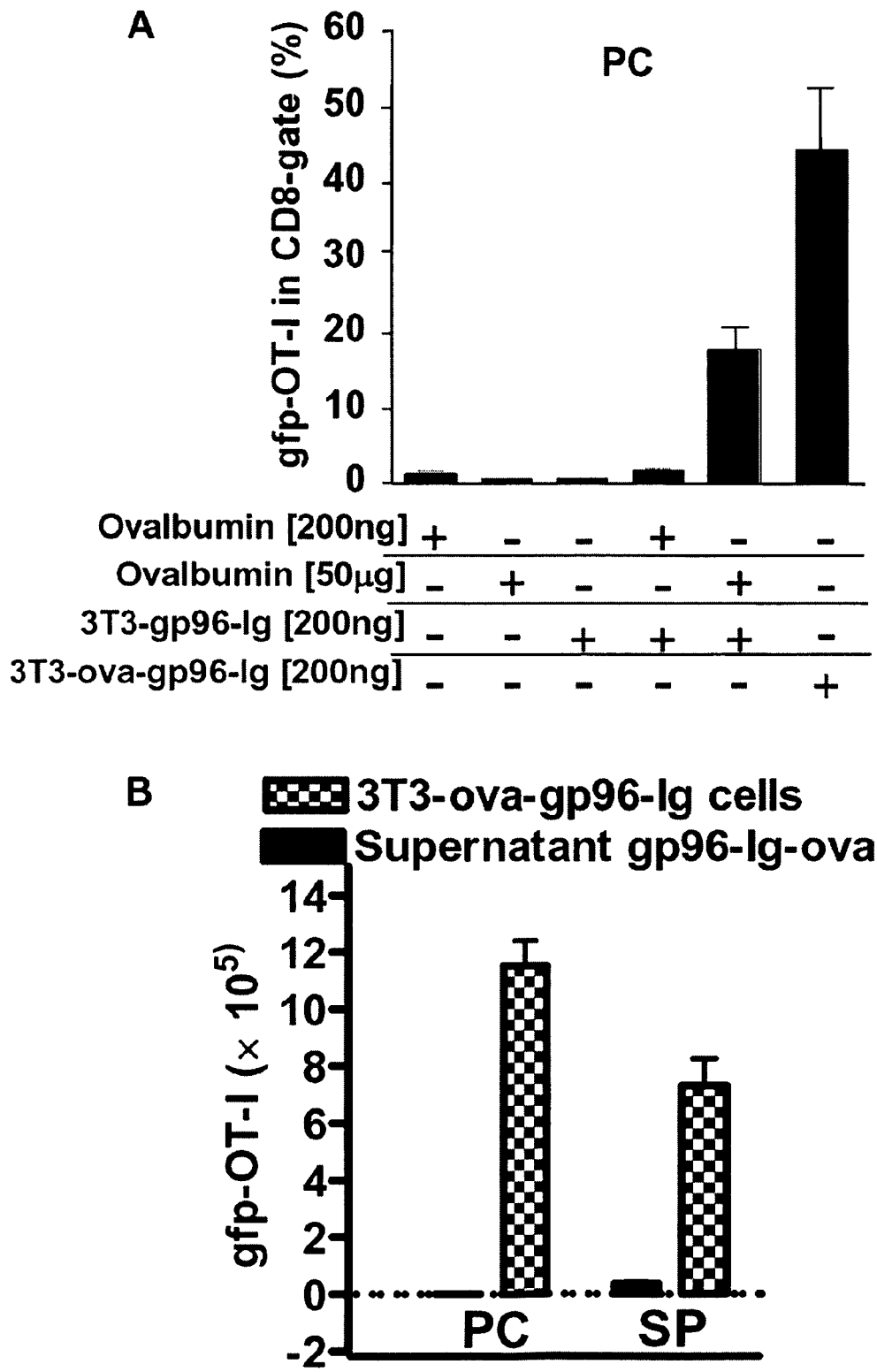
FIGS. 10A-B. Gp96 is an adjuvant for protein cross-priming and acts most efficiently when continuously released. A, Mice received 1 million GFP-OT-I i.v. and 2 days later were i.p. immunized as indicated. In vivo GFP-OT-I expansion was measured by FACS on day 4 after immunization. Secreted products from injected cells were quantitated by ELISA in vitro. The amount of secreted product indicated refers to the amount secreted in culture within 24 hours by the number of cells injected. Note that 50 µg OVA along with 200 ng gp96 secreted from 3T3-gp96-Ig cells cause less GFP-OT-I expansion than 200 ng gp96-Ig secreted from 3T3-OVA-gp96-Ig containing ~0.1% gp96-OVA. B, Mice received 1 million GFP-OT-I i.v. Two days later, they were i.p. immunized with 200 ng soluble gp96-Ig harvested from supernatant 3T3-OVA gp96-Ig cultures or with the number of 3T3-gp96-Ig cells secreting 200 ng gp96-Ig within the succeeding 24 h. GFP-OT-I expansion in the PC was determined on day 4 after immunization by flow cytometry.

Adjuvant Activity of Gp96 for CD8-CTL Cross Priming by Nonchaperoned Protein:

The data presented in FIG. 9 leaves open the possibility that gp96-Ig and OVA secreted as separate molecules rather than as a gp96-OVA complex are responsible for the efficient cross-priming of OT-I. To examine this possibility, OT-I expansion was studied under conditions where gp96 and OVA were deliberately administered as separate molecules. 3T3-gp96 cells secreting only gp96, but not OVA, were i.p. injected alone or coinjected with OVA protein and OT-I expansion was quantitated as usual. As shown in FIG. 10A, allogeneic 3T3-gp96-Ig cells secreting 200 ng per 24 hours gp96-Ig did not cause unspecific OT-I expansion. Likewise, 200 ng and 50 µg OVA injected alone was unable to mediate OT-I expansion. In contrast, when 50 µg OVA was coinjected with 3T3-gp96-Ig cells secreting 200 ng per 24 hours gp96-Ig, almost optimal OT-I expansion was observed, indicating that gp96 acts as adjuvant for OVA cross-priming of OT-I. The action of gp96 acting in trans with OVA increases OT-I cross-priming by a factor of a 100-1000 over OVA alone, while gp96 chaperoning OVA (in cis-) increases cross-priming by a factor of more than 1 million (relative to OVA alone). As negative control, 3T3-gp96-Ig in the absence of OVA had no effect on OT-I expansion despite their allogenicity. Moreover, 3T3-gp96-Ig secreting 200 ng gp96-Ig in combination with coinjected 200 ng OVA protein was unable to cross-prime OT-I, ruling out the possibility of extracellular complex formation gp96-Ig and OVA.

The data suggest that the adjuvant effect of gp96 is mediated by activation of DC and stimulation of pinocytosis, resulting in increased uptake of OVA protein and cross-presentation by MHC I to OT-I. Although gp96 shows considerable adjuvanticity for cross-priming of nonchaperoned OVA, internalization of gp96-OVA complexes via the CD91 receptor is even more efficient in procuring the gp96-chaperoned peptides for class I MHC presentation and thereby further enhancing cross-priming efficiency.

Continuous secretion of gp96-Ig provides maximal CD8 cross priming activity for adoptively transferred transgenic and for endogenous CD8 cells: The model system of secretion of gp96 from tumor cells raises the question how continuous secretion of gp96 compares to bolus injection of gp96 in its effect on OT-I cross-priming. Because OVA and OT-I are artificial test systems, it was also important to ensure that data obtained with OT-I are applicable to endogenous, nontransgenic CD8 cells. Importantly, EG7-gp96-Ig immunization of B6 mice provided 50- to 100-fold increased, CD8-dependent protection against subsequent challenge with parental EL4 cells, but not against Lewis lung carcinoma, compared with preimmune mice, suggesting gp96-dependent cross-priming against endogenous tumor antigens. Yamazaki et al., 1999, *J. Immunol.* 163: 5178-5182. Endogenous, nontransgenic OVA-specific CD8 cells occurring at low frequency of ~1 in 20,000 CD8 cells (0.005%) expand to EG7-gp96-Ig immunization to a frequency of 1-3% in the CD8 gate, indicating similar expansion as OT-I, starting from a lower frequency (data not shown). Together, these data indicate that gp96-mediated cross-priming is not restricted to the TCR-transgenic OT-I cells but also functions with endogenous tumor-specific and OVA-specific CD8 cells.

Comparing the effect of i.p. injection of 200 ng serum-free gp96-Ig-OVA harvested from 3T3-OVA-gp96-Ig cultures with the effect of injecting 3T3-OVA-gp96-Ig cells secreting 200 ng within 24 hours in vivo, a dramatic increase of OT-I expansion was observed when gp96-OVA was secreted continuously over a bolus of gp96-OVA (FIG. 10B). This observation indicates that continuous release of gp96 that may occur, e.g., as a consequence of ongoing cell death by infection, is an optimal stimulus for cognate CD8 cross-priming without CD4 help and without need for lymph nodes.

This study reveals an astonishing enhancement of cross-priming activity by gp96-chaperoned peptides by >1 million-fold in comparison to pure protein alone. This finding is significant because it provides a highly sensitive mechanism for the generation of CD8 CTL to antigenic peptides released by dying cells.

In our analysis of the efficiency of antigen cross-presentation, OT-I expansion served as a sensitive and quantitative readout for antigen cross-presentation mediated by gp96-OVA, by gp96 plus OVA, or by OVA alone. The observed differences in OT-I expansion can only be explained by the efficiency of cross-presenting activity of the different forms of OVA. Gp96-chaperoned-OVA clearly is most active in cross-presentation, followed by OVA plus gp96 as adjuvant and then OVA alone, which is more than 1 million-fold less active in cross-priming than chaperoned OVA.

This mechanism of gp96-mediated cross-priming may be physiologically important when cells die due to infection or necrosis, a process that may be accompanied by the release of gp96-chaperoning antigenic peptides derived from the infectious$^{agent}$ that caused cell death. The attraction and activation of DC and NK cells to the site of infection, cell death, and gp96 release provides an efficient pathway for cross-presentation of antigenic, gp96-chaperoned peptides to CD8 cells and for the generation of CTL in situ independent of lymph nodes. These CTL then serve to eliminate neighboring infected cells, thereby limiting the spread of the infectious agent.

A defense system based on stimulation of the innate immune system by heat shock proteins clearly has been in existence already in early vertebrate phylogeny in amphibians. With the evolution of adaptive immunity, it appears that the role of gp96 expanded from its adjuvant function to that of a carrier of specific antigens for efficient MHC class I cross-presentation and cross-priming of CD8 CTL.

In support of this model and hypothesis, we provide evidence that gp96 secretion in situ results in local recruitment and activation of large numbers of DC and NK cells that are able to activate cognate CD8 cells locally. DC in response to gp96 secretion proliferate in the PC but not at other sites; similarly, NK cells become activated only in the PC. Cognate CD8 cells show earliest and most active proliferation in the PC; later however, CD8 proliferation also spreads to other sites including the spleen. The interpretation of local cross-priming of CD8 cells by gp96, as suggested in our model in the PC, predicted and required that the cross-priming process should be able to function in the absence of lymph nodes. This was confirmed in LTα ko mice. Importantly, efficient CD8 cross-priming by gp96-Ig is not restricted to the PC. Equally efficient CD8 cross-priming and generation of systemic immunity was also observed upon s.c. immunization with gp96-Ig-secreting tumors The peritoneal site was chosen for analysis due to its easy access and absence of confounding cell populations found at other sites.

Lymph node-independent cross-priming of CD8 cells by gp96-chaperoned peptides is in accord with its independence of CD40L and CD4 help. DC activation instead appears to be mediated by gp96 binding to CD91 and TLR2/4 as shown previously by others. In preliminary experiments, we were able to demonstrate that anti-CD91 antibodies completely blocked gp96-mediated CD8 cross-priming. Costimulation of CD8 cells by CD80 and CD86, however, is absolutely required for CD8 cross-priming by gp96.

These studies also show that gp96 can act as adjuvant for CTL generation by enhancing cross-priming of antigenic proteins residing in the extracellular milieu. Release of heat shock proteins from dying cells may act as a "danger signal" activating the innate immune response by activating DC, stimulation of pinocytosis of extracellular proteins by DC and their MHC I cross-presentation. The adjuvant activity of gp96 also activates NK cells, thereby triggering Th1 responses and enhancing the clearance of extracellular infectious agents.

An important factor for the extraordinary cross-priming activity of gp96 is its continuous, sustained release by secretion. In our model system, allogeneic or syngeneic tumor cells secrete gp96, allowing the analysis of a single variable, gp96 secretion vs nonsecretion, in an in vivo system. This methodology does not require cell fractionation and purification of antigen or gp96, thereby avoiding potential problems associated with biochemical purification procedures. Data show that sustained (24 h) release (secretion) of small quantities of gp96-peptide complexes (~200 ng/24 h) is much more efficient in CD8 cross-priming than the same amount of gp96-peptide complex injected as a bolus. Apparently, continuous stimulation of the immune system over a period of time, similar to what would be observed in an ongoing infection, is a much stronger immune stimulus than a bolus that is quickly diluted or taken up by phagocytic cells. Preliminary data suggest that the live, i.p. injected allogeneic 3T3 fibroblasts secreting gp96 survive for 5-7 days before they are eliminated. Irradiation of gp96-secreting tumor cells, or treatment with mitomycin C, does not diminish their gp96 secretion nor their in vivo cross-priming activity (data not shown), indicating that cell replication is not required for enhanced CD8 cross-priming.

In addition to revealing a potentially important lymph node- and CD4-independent immune defense mechanism, these studies provide the basis for the design of efficient cellular vaccine strategies.

EXAMPLE 3

Surmounting Tumor-Induced Immune Suppression by Frequent Vaccination or Immunization in the Absence of B Cells This example demonstrates that tumor-induced immune suppression is antigen nonspecific and can be overcome by frequent immunization or by the absence of B cells. Established tumors suppress CD8 T cell clonal expansion in vivo, which is normally observed in tumor free mice upon antigen-specific glycoprotein (gp) 96-chaperone vaccination. Suppression of CD8 T-cell expansion by established tumors is independent of tumor-associated expression of the antigen that is recognized by the CD8-T-cell receptor. Vaccination of tumor-bearing mice is associated with increased cellular recruitment to the vaccine site compared with tumor-free mice. However, rejection of established, suppressive tumors required frequent (daily) gp96 vaccination. B cells are known to attenuate T helper cell-1 responses. We found that in B-cell deficient mice, tumor rejection of established tumors can be achieved by a single vaccination. Accordingly, in tumor-free B-cell deficient mice, cognate CD8 cytotoxic T lymphocyte clonal expansion is enhanced in response to gp96-chaperone vaccination. Frequent vaccination with cellular vaccines and concurrent B-cell depletion may greatly enhance the activity of anticancer vaccine therapy in patients.

Mice:

C57BL/6J (B6) mice were purchased from The Jackson Laboratory (Bar Harbor, Me.) or Charles River Laboratories (Frederick, Md.). Ig-m-chain-deficient mice having a C57BL/6J background [B-cell deficient mice (BCDM)] were purchased from The Jackson Laboratory.

GFP mice were obtained by kind permission from the producers. C57BL/6J oxytocin-1 (OT-1) mice (obtained from Dr M. Bevan, University of Washington, Seattle, Wash.) express a transgenic TCR (Va2Vb5.1.2) specific for the H-2Kb-restricted chicken ovalbuminderived peptide 257 to 264 (SIINFEKL). GFP mice were crossed with OT-1 mice to generate GFP-OT-1 mice in the animal facility at the University of Miami, according to institutional guidelines. The progeny mice were screened by polymerase chain reaction for the expression of the ova-TCR gene and by fluorescence for GFP. All mice were used at 6 to 12 weeks of antigene.

Cell Lines: The EG7 cell line (obtained from M. Bevan) was transfected with the vector pCMG-His containing gp96-Ig as described. Control cells were transfected with vector alone. Lewis lung carcinoma (LLC) cells were obtained from the American Tissue Culture Collection and were transfected with ovalbumin in pAC-neo-ova or with both the ovalbumin vector and pCMG-His containing gp96-Ig. All cells were cultured in Iscove modified Dulbecco media (GIBCO, Carlsbad, Calif.) with 10% fetal calf serum and gentamycin (GIBCO). To maintain transfected cells, antibiotics for selection (G418 or L-Histidinol, Sigma, St Louis, Mo.) were added to the culture.

Antibodies:

The following antibodies were used for staining; anti-CD 16/32 (2.4G2), CyChrome-anti-CD3e (145-2C11), CyChrome-anti-CD5 (UCHT2), CyChrome-anti-CD8a (53-6.7), PE-CD19 (4G7), PE or FITC-anti-NK1.1 (PK136), and PE or FITC-anti-CD11c (HL3) were purchased from BD PharMingen (San Diego, Calif.).

Purification and Adoptive Transfer of GFP-OT-1 Cells and CD19+ B Cells:

Pooled single cell suspensions of splenocytes and lymph node cells were obtained from GFP-OT-1 mice and were depleted of red blood cells by ammonium chloride lysis. GFP-OT-1 cells were sorted by positive column selection using anti-CD8a magnetic microbeads and a MACS column (Miltenyi Biotec, Auburn, Calif.), according to the manufacturer's instructions. The purity of isolated OT-1 cells was more than 95% as determined by flow cytometric analysis. Va2 and Vb5.1.2 expression on purified cells was quantified by flow cytometry. For purification of B cells, CD19+ cells were purified with anti-CD19 microbeads (Miltenyi Biotec, Auburn, Calif.). To reconstitute B cells in BCDM mice, $10^7$ purified cells were adoptively transferred through tail veins 2 days before transplantation of tumor cells.

Analysis of In Vivo CD8 CTL Expansion:

To measure CD8+ CTL expansion, mice were adoptively transferred with $10^6$ GFP-OT-1 and immunized 2 days later by IP injection of $1 \times 10^6$ to $4 \times 10^6$ nonirradiated EG7-gp96-Ig cells. After timed intervals following immunization, cells were harvested from the peritoneal cavity, mesenteric, para-aortic lymph nodes [draining lymph nodes (dLN)], and peripheral blood at the indicated time. Red blood cells were removed from samples by ammonium chloride lysis. One million cells were incubated for 10 minutes at 4° C. with anti-CD16/32 monoclonal antibodies in phosphate-buffered saline (PBS) containing 0.5% bovine serum albumin (phenyl boric acid) to block FcR binding. Thereafter, cells were incubated with the indicated antibodies for 30 minutes. Samples were analyzed on a FACScan (Becton Dickinson) with CELL Quest software (BD Bioscience). The total number of the indicated immune cells per tissue was calculated from the percentage of targeted cells and total number of cells in each tissue.

Tumor Inoculation and Treatment Protocol:

Nonirradiated EG7, LLC, or LLC-ova cells were injected SC in 200-mL PBS into the flanks of mice. Five days after the inoculation of LLC-ova cells (day 5), $10^6$ purified GFP-OT-1 in a volume of 0.3-mL PBS were injected through tail veins. Two days later, mice were immunized by IP injection of $10^6$ nonirradiated LLCova-gp96-Ig or EG7-gp96-Ig cells in a volume of 0.5-mL PBS according to the schedule indicated in the graphs. Control mice were treated with PBS or with EG7 or LLC-ova. The size of tumors in the flank was measured in 2 dimensions twice per week for at least 20 days.

Statistical Analysis:

Significance was evaluated by repeated measures analysis of variance and by Wilcoxon signed rank test. Values of $P<0.05$ were considered to indicate statistical significance.

Established Tumors Suppress Gp96-Mediated CD8 CTL Expansion Independent of TCR Specificity:

Transfection of heat shock fusion protein gp96-Ig into tumor cells results in the secretion of gp96-Ig along with gp96-chaperoned peptides. Gp96-Ig is a fusion protein generated by the replacement of the endoplasmic reticulum retention signal (KDEL) of gp96 with the Fc portion of IgG1. Injection of mice with gp96-Ig-secreting tumor cells results in the induction of tumor-specific immunity and memory and protection from subsequent challenge with the same, but untransfected tumor. Tumor immunity generated by secreted gp96-Ig is specific for gp96-chaperoned peptides, including peptides derived from tumor endogenous antigens, such as EL4-specific antigens, and for surrogate antigens, such as ovalbumin transfected into EL4 (EG7) or LLC (LLC-ova). The ovalbumin surrogate antigen offers a method to accurately determine CD8 CTL expansion in vivo via adoptive transfer of ovalbumin-specific, OT-1 TCR transgenic CD8 cells.

Established tumors are known to be suppressive for CTL expansion. To measure CTL responses in the presence or absence of established tumors, we used the TCR transgenic OT-1 system in which transgenic CD8 CTL respond to ovalbumin-transfected syngeneic or allogeneic tumors secreting gp96-Ig-ova. As transplantable tumor models, we used EG7, derived from the EL4 by ovalbumin transfection, which is classified as immunogenic and highly tumorigenic. In addition, we also used the LLC and LLC-ova, which is considered less immunogenic and highly tumorigenic. The division rate of both cell lines is very rapid with a doubling time of 8 to 12 hours in culture.

Figure 11:
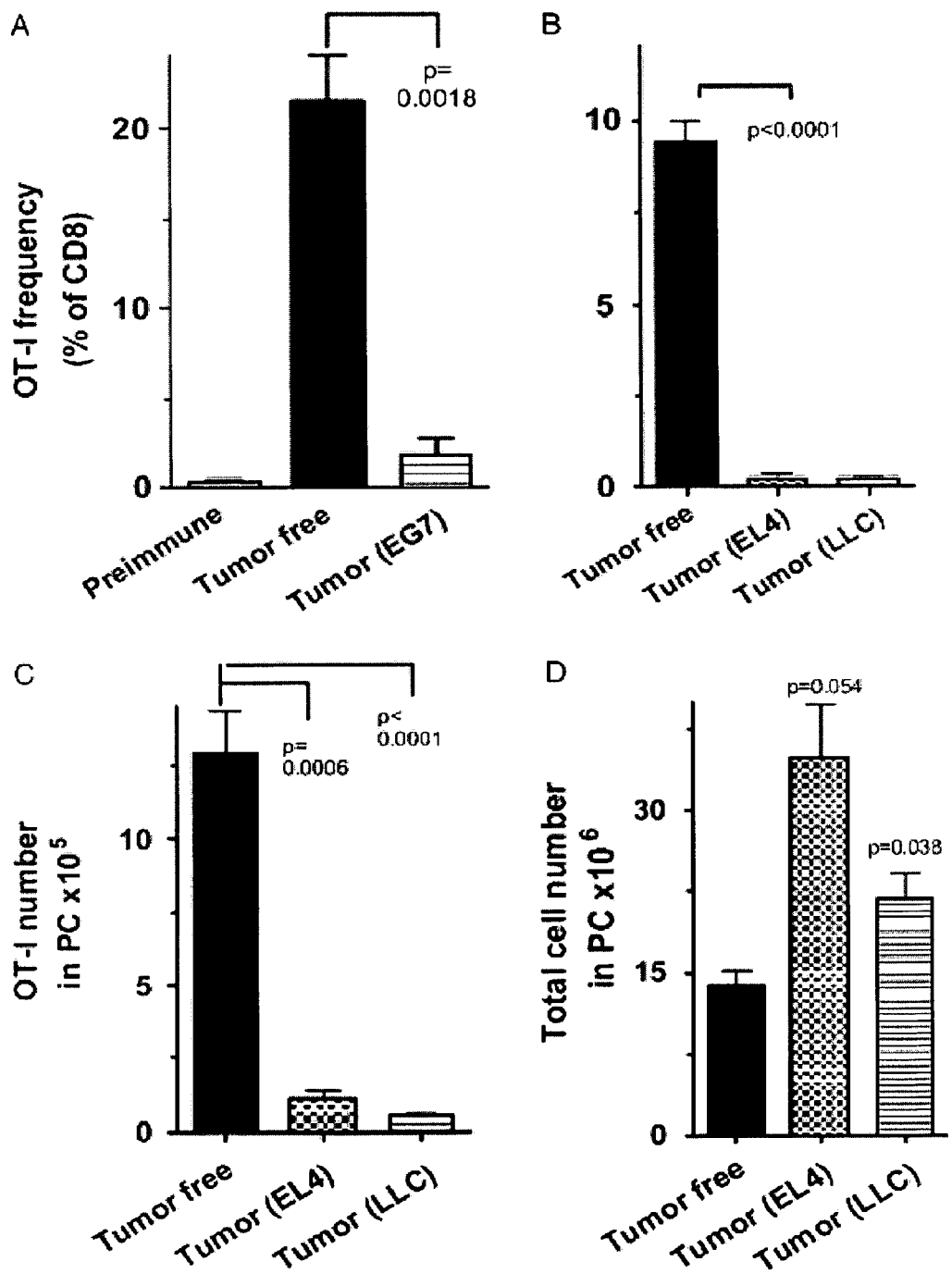
FIGS. 11A-D. Antigen nonspecific suppression of OT-1 CTL expansion by distant, established tumors. A, Comparison of OT-1 CD8 CTL frequency in the peritoneal cavity in unimmunized mice; in immunized, tumor-free mice; and in immunized, EG7-tumor-bearing mice. One million EG7 tumor cells were transplanted subcutaneously in the flank and allowed to be established for 5 days before immunization with EG7-gp96-Ig. One million OT-1 CD8 T cells were adoptively transferred IV 2 days before immunization. Mice were immunized with 2 million EG7-gp96-Ig IP. Peritoneal cells were analyzed 5 days later by flow cytometry. B, Suppression of OT-1 expansion by established tumors is antigen nonspecific. EL4 and LLC, not expressing ovalbumin, were established for 5 days in place of EG7. OT-1 adoptive transfer and vaccination was carried out as in A. C, Absolute numbers of OT-1 accumulating in the peritoneal cavity, the vaccination site, in the absence or presence of established tumors (same experiment as B). D, The total cell number recruited to the peritoneal cavity by EG7-gp96-Ig immunization is increased in the presence of established tumors. A representative experiment of 3 or more individual experiments is shown. N=3 to 5 mice in each group. Significance values indicated in the figure were calculated by t test. Negative controls are unimmunized mice (preimmune) and positive controls are mice without peripheral tumor in the flank. CTL indicates cytotoxic T lymphocytes; gp, glycoprotein; Ig, immunoglobulin; LLC, Lewis lung carcinoma.

After a single IP immunization with one million EG7-gp96-Ig cells, secreting 60 to 80-ng gp96-Ig/$10^6$ cells in 24 hours, OT-1 CD8 T cells expand from low, preimmune levels in the CD8 gate (B0.2%) to high frequencies (15% to 40%) in tumor-free mice (FIG. 11A). Administration of irradiated EG7 not secreting gp96-Ig is not able to cause significant OT-1 expansion. However, the presence of subcutaneously established EG7 tumors at a distant site in the flank significantly inhibits gp96-vaccine-induced expansion of OT-1 in the peritoneal cavity (FIGS. 11A-C) and systemically in spleen and lymph nodes (not shown). EG7 tumors secrete ovalbumin and express Kb-ova. It is possible, therefore, that adoptively transferred OT-1, upon recirculation through the tumor bed or tumor dLN, become anergic due to receiving signals through their Kb-ova-specific TCR while not receiving costimulatory signal. To test this hypothesis, the syngeneic tumors EL4 and LLC, neither expressing ovalbumin, were established subcutaneously at distant sites. Subsequently, OT-1 were adoptively transferred IV and mice were immunized IP with EG7-gp96-Ig as before. Established EL4 and LLC were as effective in suppressing OT-1 expansion by secreted gp96-ova as established EG7 indicating that suppression is not dependent on the appropriate TCR antigen, Kb-ova, in the tumor (FIGS. 11B, C). Although OT-1 expansion in the peritoneal cavity and systemically was suppressed by the presence of LLC and EL4 at distant sites, surprisingly, total cell recruitment after immunization into the peritoneal cavity upon EG7-gp96-Ig immunization IP was actually increased when compared with tumor-free mice (FIG. 11D).

The data indicate that established tumors can cause the induction of antigen nonspecific suppression of CTL expansion. This induction of suppression correlates with increased cellular recruitment to the vaccine site in the peritoneal cavity. Whether this increased cellular recruitment is responsible for the suppression of CD8 T cells is under investigation.

To overcome antigen nonspecific immune suppression, these experiments test whether frequently repeated antigen specific stimulation of CD8 CTL by vaccination could counteract the suppressive activity found in tumor bearing mice.

Rejection of Established Tumors Requires Frequent Gp96-Ig Immunizations:

Although many vaccination strategies, including secreted gp96-Ig, are able to establish protective immunity in mice against tumors and tumor antigens, it is more difficult to reject already established tumors by therapeutic vaccination. Given the observation of antigen nonspecific suppression of CD8 expansion, we analyzed how different vaccination schedules affected tumor rejection and/or tumor growth.

Figure 12:
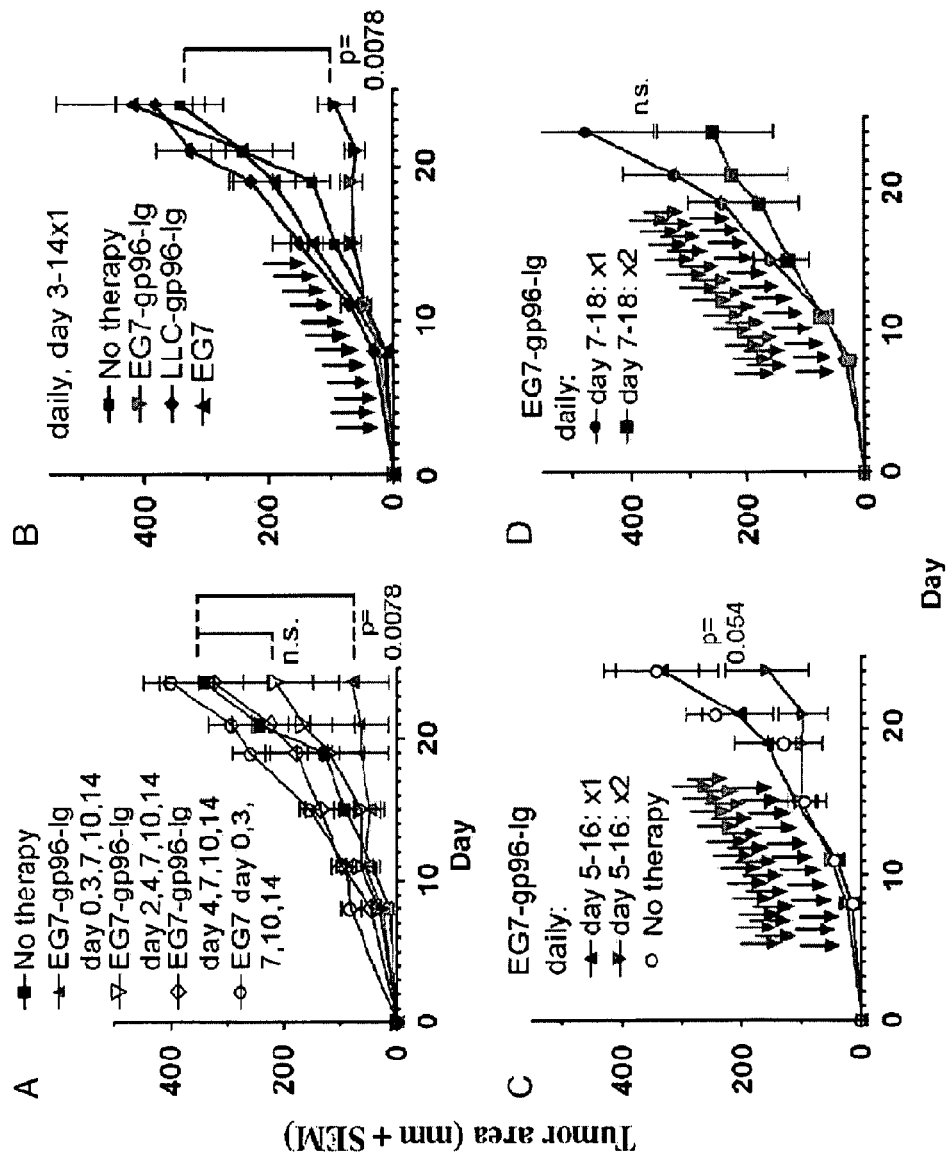
FIGS. 12A-D. Frequent gp96 immunizations can overcome tumor-induced immune suppression. A, One million EG7 tumor cells were transplanted subcutaneously in the flank. Immunization by IP administration of one million EG7-gp96-Ig or irradiated EG7 was started on the same day or 2 or 4 days after tumor transplantation. Negative controls—no therapy, n=17; irradiated EG7 immunization, n=15. Immunization with EG7-gp96-Ig at different schedules, n=15. B, Same as in A except that IP immunization was started on day 3 and was repeated daily until day 14 (black arrows). One million EG7-gp96-Ig (n=17) or one million LLC-gp96-Ig (n=5) or irradiated EG7 (negative control, n=5) or no therapy (negative control, n=19). C, Tumors were established for 5 days and then immunization IP with one million EG7-gp96-Ig was given once (black arrows) or twice daily (red arrows) from day 5 to 16; n=5 in each group. D, Tumors were established for 7 days and then immunization IP with one million EG7-gp96-Ig was given once (black arrows) or twice daily (red arrows) once or twice daily from day 7 to 18; n=5 per group. The significance values of differences in tumor growth are indicated in the individual graphs. gp indicates glycoprotein; Ig, immunoglobulin; LLC, Lewis lung carcinoma; ns, not significant.

We initially analyzed the effect of therapeutic vaccination by beginning vaccination on the same day as tumor transplantation. One million EG7 tumor cells were transplanted subcutaneously in the flank of syngeneic mice. On the same day (day 0), one million gp96-Ig-secreting EG7 vaccine cells (EG7-gp96-Ig), secreting gp96-Ig at a rate of 60 to 80 ng/$10^6$ cells×24 hours were administered IP as vaccine, and vaccination was repeated on day 3, 7, 10, and 14. Compared with mice not receiving therapy, tumor growth is significantly (P=0.0078) diminished by 4 EG7-gp96-Ig vaccinations starting on the same day as tumor transplantation (FIG. 12A). The therapeutic effect is gp96 and antigen dependent. Irradiated EG7, not secreting gp96-Ig (FIG. 12A), or LLC-gp96-Ig (FIG. 12B), not expressing EG7 antigens but secreting gp96-Ig at the same rate as EG7-gp96-Ig, are unable to retard tumor growth when administered IP as vaccine at the identical dose and schedule as EG7-gp96-Ig. When vaccination with EG7-gp96-Ig is started 2 days or later after EG7 inoculation, the therapeutic effect using the same vaccination schedule is substantially diminished (FIG. 12A). These data demonstrate that even after 2 days, established tumors are more difficult to control by vaccination than tumors that are freshly transplanted.

Whether tumors established for 3 or more days could be controlled by more frequent vaccination schedules was also tested. One million EG7 tumor cells were transplanted subcutaneously in the flank and allowed to be established for 3 to 7 days, allowing at least 7 or more tumor cell doublings. During this period, vascularization of the tumor nodule occurs, which is detectable visually. Mice were then vaccinated daily IP with one million EG7-gp96-Ig cells or, in specificity controls, with the same schedule and dose of LLC-gp96-Ig cells, or irradiated EG7 cells, or left unvaccinated. Daily vaccination with EG7-gp96-Ig significantly (P=0.0078) and effectively controlled growth of EG7 that had been established for 3 days (FIG. 12B), whereas daily vaccination with irradiated EG7 or with LLC-gp96-Ig had no effect on growth of established EG7 (FIG. 12B). In further studies, we allowed the transplanted EG7 tumors to become established for 5 and 7 days before starting vaccination with EG7-gp96-Ig. As shown in FIGS. 12C and D, 2 vaccinations every day were required to retard tumor growth at this later stage of tumor establishment. The data show that frequent immunization can check tumor growth for a period of 24 days in mice. Further studies will be needed to determine whether continued long-term vaccination schedules can completely eradicate tumors.

Figure 13:
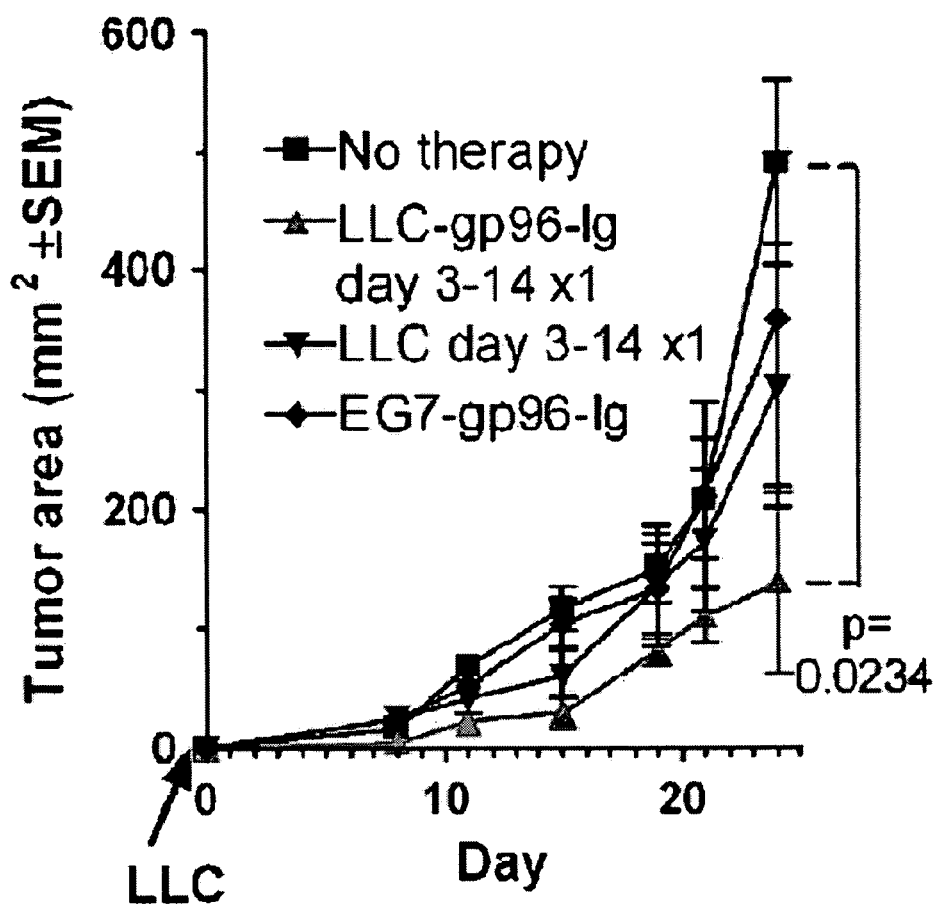
FIG. 13. Frequent immunizations cause tumor growth retardation of established LLC. LLC (105) were transplanted subcutaneously in the flank and allowed to be established for 3 days. Immunization with one million LLC-gp96-Ig (n=15), EG7-gp96-Ig (n=5) or irradiated LLC (n=5), or no therapy (n=19) was started on day 3 and repeated on day 7, 10, and 14. The significance of the difference between 19 untreated and 15 treated tumor-bearing mice (P=0.0234) is shown. gp indicates glycoprotein; Ig, immunoglobulin; LLC, Lewis lung carcinoma.

To validate the data obtained with the immunogenic EG7 lymphoma, experiments were repeated with less immunogenic, established LLC (FIG. 13). Repeated IP immunizations (day 3, 7, 10, and 14) with LLC-gp96-Ig beginning on the third day after tumor transplantation resulted in significant (P=0.0234) retardation of tumor progression of LLC. Daily immunizations for LLC were not more effective in tumor retardation. The effect of immunization was tumor specific as EG7-gp96-Ig vaccination was unable to control LLC tumor growth. Tumor growth control also could not be achieved by irradiated LLC, but was dependent on gp96-Ig secretion.

These data suggest that frequent DC and NK cell activation, combined with antigen cross presentation by secreted gp96-Ig and its chaperoned peptides, can overcome established tumor-induced, antigen nonspecific immune suppression.

Figure 14A:
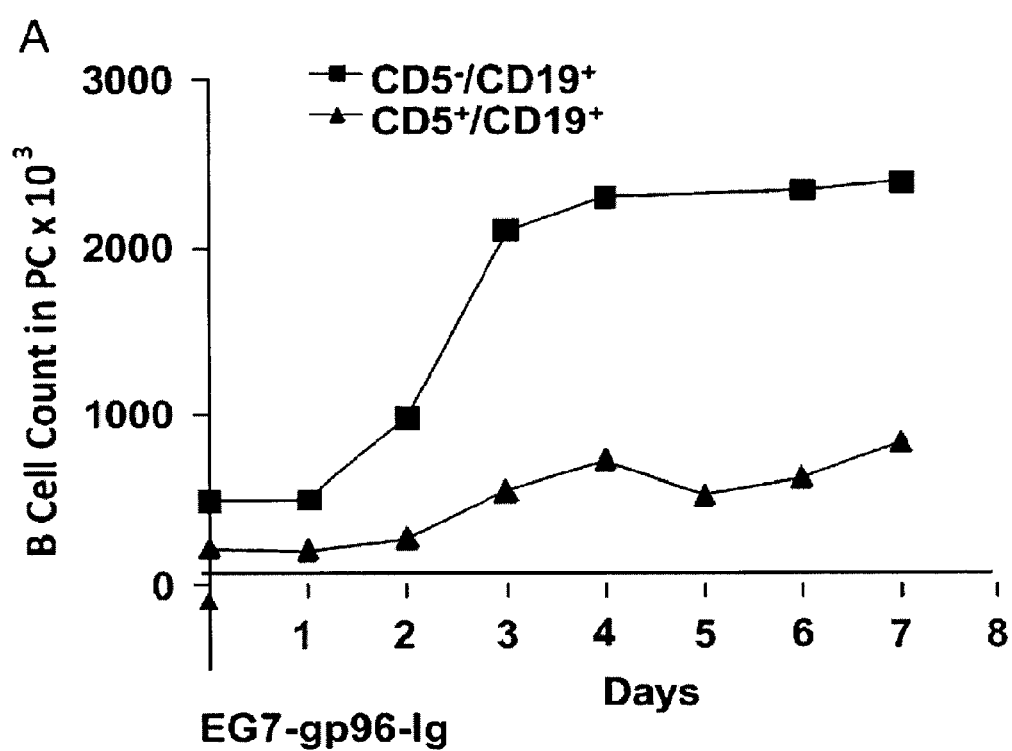
FIGS. 14A-B. B cells inhibit gp96-mediated recruitment of NK cells into and retention of DCs in the peritoneal cavity. A, Recruitment of B cells, but only modest CD5+ B cells, into the peritoneal cavity by EG7-gp96-Ig immunization. Tumor-free mice received one million EG7-gp96-Ig IP Accumulation of CD5+ and CD5_ B cells was determined daily thereafter by flow cytometrty. Representative of more than 3 experiments. B, Increased recruitment of NK cells and retention of NK cells and DCs and in B-cell deficient mice (BCDM) and its reversal by adoptive transfer of B cells. WT and BCDM were immunized IP with 2 million EG7-gp96-Ig and cells harvested from the peritoneal cavity 2 and 4 days later and analyzed by flow cytometry. B-cell reconstitution was carried out by IV adoptive transfer of 107 WT B cells 2 days before immunization with EG7-gp96-Ig. Representative of 3 experiments. BCDM indicates B-cell deficient mice, DC, dendritic cell, gp, glycoprotein; Ig, immunoglobulin; NK, natural killer, WT, wild type.
Figure 14B:
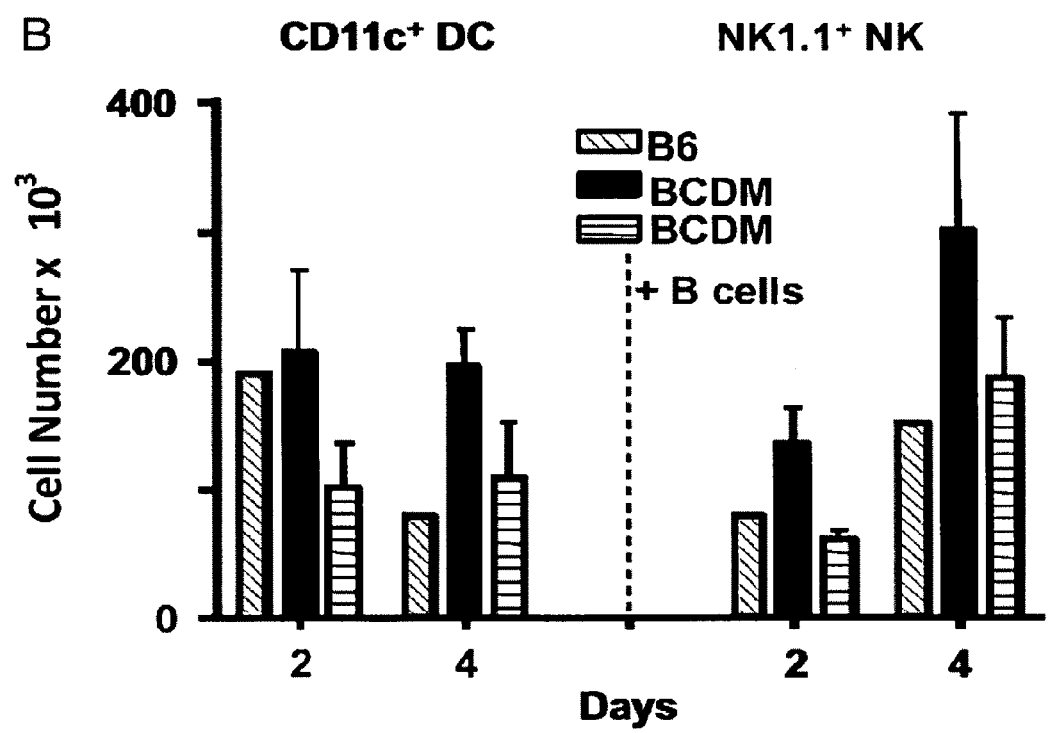

Gp96-Mediated DC and NK Cell Recruitment and CD8 CTL Expansion is Enhanced in BCDM:

It has been reported by several groups that T helper cell-1 antitumor responses are enhanced in BCDM when compared with wild type (WT) mice. We, therefore, studied the role of B cells in gp96-mediated CTL expansion and antitumor immunity. The peritoneal cavity is populated by CD5+ CD19+ B cells and by CD5+CD19+ B1-B cells, the latter producing IgM antibody and not undergoing isotype switching upon activation (FIG. 14A). Upon IP immunization with EG7-gp96-Ig, the CD5+CD19+ population increases about 5-fold by day 4 postimmunization, whereas CD5+ B1-B cells increase only moderately (FIG. 14A). Gp96-mediated OT-1 expansion is maximal on day 4 and 5 postimmunization. It is preceded by recruitment into and activation of DCs and NK cells in the peritoneal cavity, the site of vaccination. NK cells are important facilitators of gp96-Ig mediated CD8 CTL expansion as shown previously. In BCDM, the recruitment of DCs into the peritoneal cavity (the vaccine site) was similar to recruitment in WT mice on day 2 after vaccination. However, although the DC numbers decreased by day 4 postvaccination by 50% in WT mice, DC numbers in B cell deficient mice remained at the same high frequency (FIG. 14B). NK cell recruitment in BCDM was increased on day 2 and day 4 (FIG. 14B). The difference did not reach significance but was reproducible in 3 separate experiments. Adoptive transfer of WT B cells to BCDM abolished increased retention of DCs and recruitment of NK cells. The finding suggests that B cells influence gp96-induced recruitment of innate immune cells and suggest that B cells may also be involved in regulating or suppressing CD8 CTL expansion.

Figure 15:
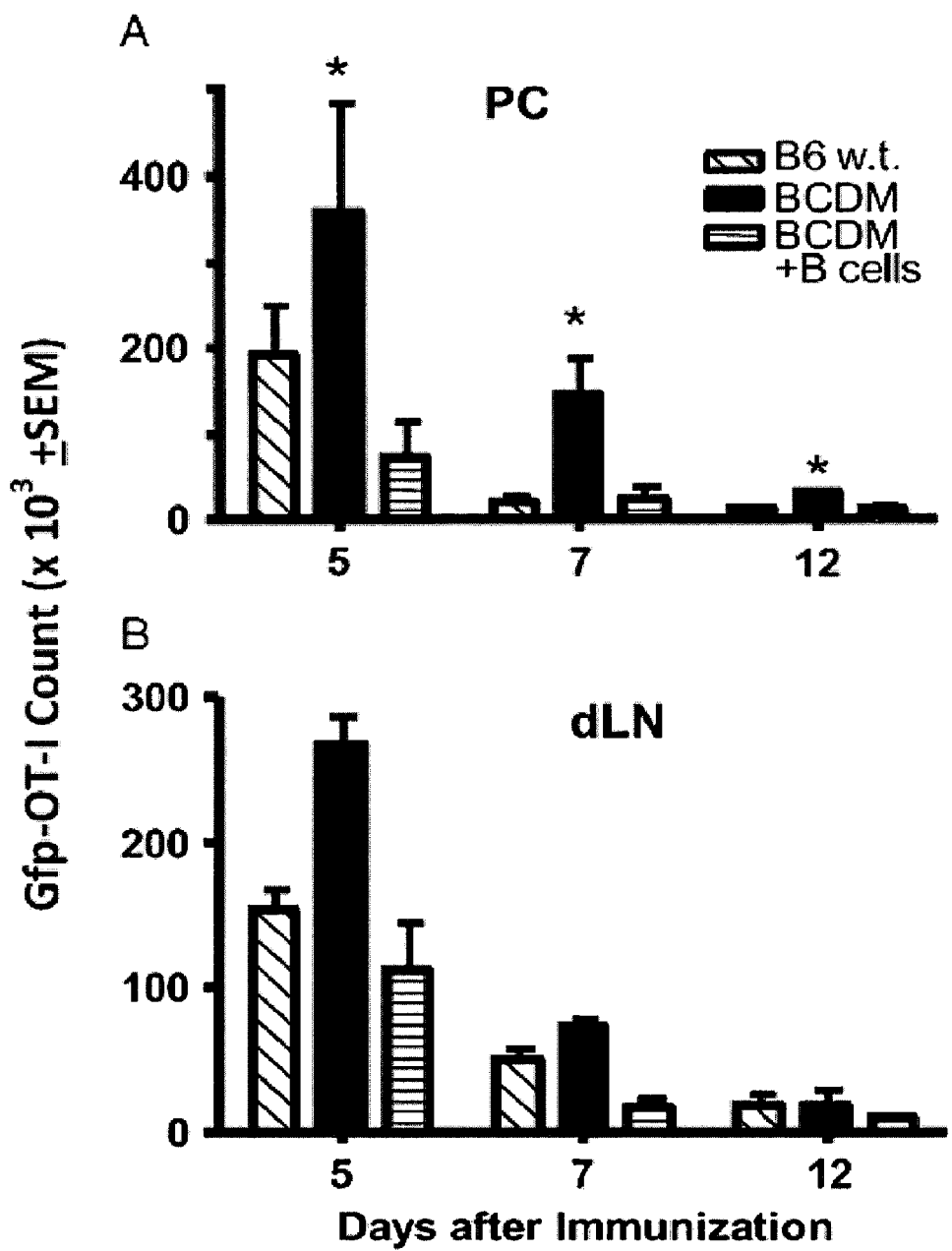
FIGS. 15A-B. Gp96-mediated OT-1 CD8 CTL expansion is increased and sustained in the absence of B cells. WT mice and B-cell deficient mice received one million GFP-OT-1, B-cell reconstituted mice in addition received 10 million WT B cells by IV adoptive transfer. The mice were immunized 2 days later with 4 million EG7-gp96-Ig and were analyzed on the days indicated by harvesting cells from the peritoneal cavity (A) and mesenteric and para-aortic lymph nodes (dLN) (B). *P=0.04 by repeated measures ANOVA. Four mice in each group, representative of 3 experiments. ANOVA indicates analysis of variance; CTL, cytotoxic T lymphocytes; dLN, draining lymph nodes; GFP green fluorescent protein; gp, glycoprotein; Ig, immunoglobulin; WT, wild type.

Therefore, whether expansion of GFP marked OT-1 CD8 CTL was increased in BCDM in response to gp96 immunization was also tested. As shown in FIG. 15, OT-1 expansion after gp96 immunization in BCDM was significantly enhanced on day 5 compared with WT mice. Importantly, OT-1 persisted at significantly higher frequencies on day 7 and 12 postimmunization in the peritoneal cavity (P=0.04) (FIG. 15A) In dLN (FIG. 15B), OT-1 expansion and retention was also increased without, however, reaching significance. Adoptive transfer of WT B cells to BCDM before immunization reduced OT-1 expansion to levels at or below those seen in WT mice (FIGS. 15A, B). The suppression of OT-1 expansion by the presence of B cells is not mediated by interleukin (IL)-10 productions because IL-10-deficient mice exhibit OT-1 expansion similar to WT mice rather than the enhanced expansion as seen in BCDM.

Gp96-Mediated Rejection of Established Nonimmunogenic Tumors is Enhanced in the Absence of B Cells:

As shown above, growth control of established EG7 tumors in WT mice minimally requires daily gp96 immunization. Similarly, LLC progression can be retarded by frequent immunizations. EG7 and EL4 cells are rejected in BCDM and do not establish tumors; however, LLC and LLC-ova can be established in BCDM although they grow at a slower rate than in WT mice. LLC-ova was established subcutaneously in the flank for 5 days in BCDM and in WT mice. OT-1 were adoptively transferred IV and, 2 days later, one million LLC-ova-gp96-Ig were administered as a single dose IP and tumor growth in the flank monitored. In WT mice, a single immunization with LLC-ova-gp96-Ig caused significant retardation of tumor progression in the flank, but failed to reject tumors (FIG. 16A). In contrast, in BCDM, a single immunization resulted in complete rejection of established, 7-day LLC-ova tumors in 3 mice and significant tumor shrinking in 2 (FIG. 16B). In the absence of treatment, LLC-ova grow progressively in BCDM (FIG. 16B) albeit at a slower rate than in WT mice (FIG. 16A). B-cell reconstitution of BCDM (FIG. 17C) rendered the effect of vaccination similar to that seen in WT mice (FIG. 16A), namely retardation of progression. It will be of interest to determine whether complete or partial B-cell depletion by antibody will have similar effects as B-cell deficiency. Ongoing preliminary studies seem to support this approach.

Figure 17:
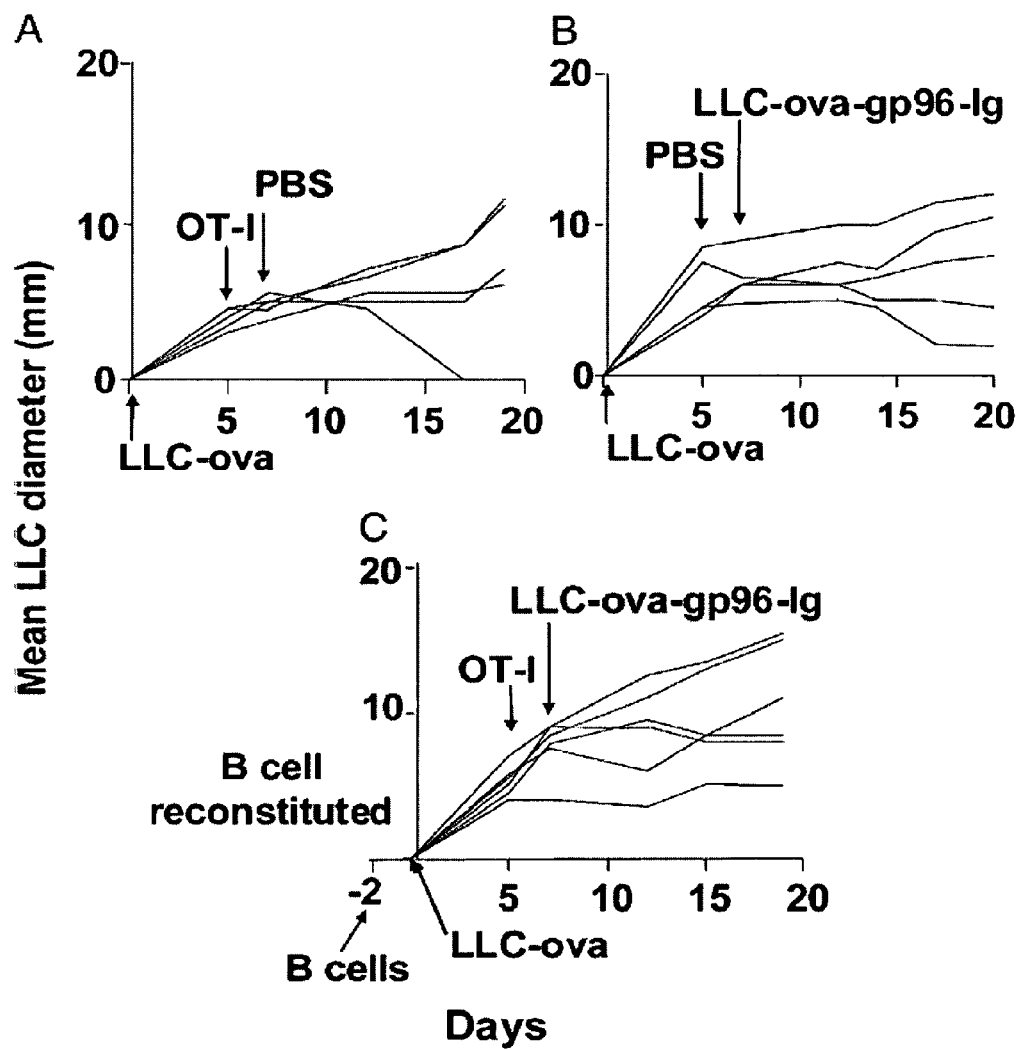
FIGS. 17A-C. High CTL precursor frequency and immunization enhance tumor rejection by gp96 vaccines in BCDM. A, BCDM were treated as in FIG. 6 except that vaccination with LLC-ova-gp96-Ig was omitted. B, As in FIG. 6. Omitting OT-1 transfer. C. As in FIG. 16, except that BCDM mice were reconstituted with 10 million B cells before tumor (LLC-ova) transplantation. n=5 to 6 mice in each group, representative of 2 experiments. BCDM indicates B-cell deficient mice; CTL, cytotoxic T lymphocytes; gp, glycoprotein; Ig, immunoglobulin; LLC; Lewis lung carcinoma.
Figure 18:
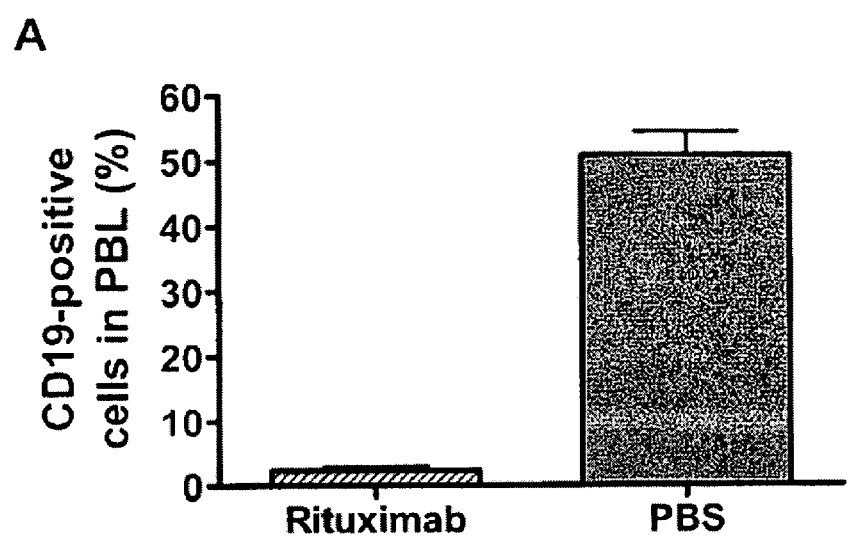
FIG. 18: Small B cell population might inhibit immune response against LLC-ova tumor challenge. Four days after LLC-ova transplantation (one day before OT-I injection), each human CD20 transgenic mice received 1 mg of Rituximab® or PBS. Seven days after the treatment, frequencies of CD19+ cells in PBL were examined by flow cytometry. There is approximately 3% of CD19+ cell population left in PBL after Rituximab® injection. Each bar data is mean±S.E. of three mice.

Optimal tumor control of established LLC in BCDM by a single immunization is dependent on sufficiently high numbers of tumor-specific CTL precursors (OT-1) and on antigen-specific immunization (LLCova-gp96-Ig). In BCDM, the presence of one million adoptively transferred OT-1 without gp96 immunization does not result in tumor rejection in the majority of mice (FIG. 17A). Likewise, gp96 immunization alone without OT-1 transfer is less effective than the combination (FIG. 17B).

It is well appreciated that established tumors suppress antitumor immunity. Tumor-specific T cells become anergic in the presence of established tumors. Anergy to the B-cell lymphoma used in that study was antigen specific, MHC restricted, and dependent on the presence of MHC matched bone marrow-derived antigen presenting cells. In other studies, antigen nonspecific myeloid-suppressor cells and T-regulatory cells have been implicated in suppression of antitumor immunity. Our studies show that the suppression of CTL responses in vivo can be achieved by established tumors through antigen independent pathways. OT-1 CD8 CTL expansion in response to gp96-ova vaccination is inhibited by established tumors independent of the expression of ovalbumin by the tumors. This type of suppression may be achieved by T-regulatory cells or by other suppressor cells such as myeloid-suppressor cells or M2 macrophages. In accord with this hypothesis, the suppressive activity, in preliminary experiments, is transferable to tumor-free mice by the transfer of peritoneal cells elicited in tumor-bearing mice by gp96 vaccination.

Although the OT-1 response to gp96-ova immunization is strongly inhibited in the presence of established tumors, it is not totally blocked, suggesting that there is a balance between immune suppression by the established tumor and vaccine-induced CD8 CTL activation through antigen cross presentation by activated DCs stimulated by secreted gp96-ova. We have shown previously that in tumor, naive mice gp96-ova results in the recruitment and activation of NK cells and DCs followed by OT-1 expansion. Established tumors, although actually enhancing recruitment of cells into the peritoneal cavity by LLC-gp96-Ig vaccination, inhibit OT-1 expansion, suggesting that in the presence of established tumors, many of the recruited cells are likely to be suppressor cells. This hypothesis predicts that frequent immunizations with gp96-ova may overcome the suppressive activity by shifting the balance from suppression to increased immune activation through repeated gp96-mediated DC and NK cell stimulation, increased antigen cross presentation, and CTL priming. Indeed, frequent immunizations have significant effects on retardation of tumor progression. In the case of established EG7, once or twice daily vaccinations were much more effective in stopping tumor progression than vaccination every second or third day. For LLC, immunization every other or every third day was sufficient and daily immunization was not more effective. These tumor-specific differences may be related to the rate by which suppressor cells are generated by the presence of the peripheral tumor. Alternatively, it may depend on the mechanism by which tumors mediate the induction of suppressor cells or the nature of the suppressor cells that have been induced.

By studying the OT-1 response to IP immunization with tumor-secreted gp96-ova, we noticed that large numbers of B cells are recruited into the peritoneal cavity, which is the vaccine site. B cells have been reported to be inhibitory for antitumor immunity, prompting the question as to their role in gp96-mediated OT-1 expansion. Using BCDM, it became immediately clear that both NK cell and DC recruitment and retention in the peritoneal cavity were increased and OT-1 expansion was enhanced after gp96-ova immunization. B-cell reconstituted BCDM responded like WT mice to gp96-ova-mediated OT-1 expansion, ruling out the possibility that B-cell deficiency had modified the responsiveness of BCDM to gp96-ova immunization in a manner unrelated to the absence of B cells. B-cell deficiency not only caused enhanced OT-1 expansion but also strongly enhanced tumor rejection of 7-day established LLC-ova tumors after a single gp96-Ig immunization. The data suggest that tumor-mediated induction of suppressor cells is greatly diminished in the absence of B cells or that B cells them act as "suppressor cells." Whether B cells participate in the induction of suppressor cells or whether B cells themselves are immunosuppressive for CTL responses needs further study; IL-10, however, does not seem to be involved in B-cell mediated suppression of tumor immunity. In ongoing studies, we have found that OX40-L-deficient B cells show-reduced ability to suppress antitumor immune responses.

These studies provide a model by which antigen independent immune suppression can be studied and further defined. The role of B cells in particular in this process will be of great interest. In addition, these studies point to ways in which antitumor vaccines can be made more effective. Depletion of B cells with antibodies and subsequent frequent vaccination, for instance with tumor secreted gp96 vaccines, may result in more efficient control of tumor growth than that seen with conventional vaccination methods.

EXAMPLE 4

Figure 16:
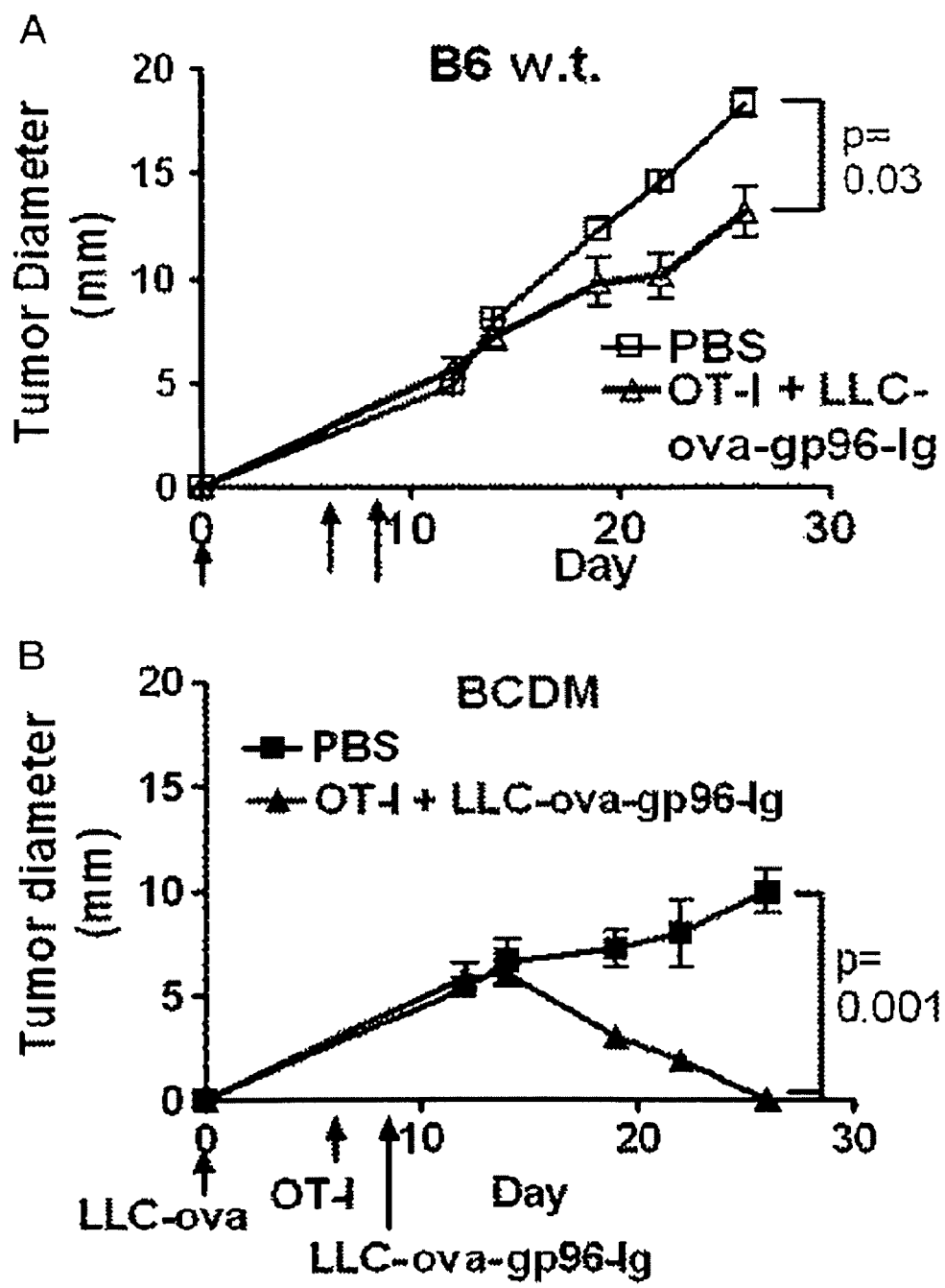
FIGS. 16A-B. Gp96-mediated tumor rejection is enhanced in BCDM and abrogated by B-cell reconstitution. A, Wild type mice. B, BCDM. One million LLC-ova cells in 0.2-mL PBS were transplanted into the flank. Five days later, one million OT-1 were given IV. Seven days after tumor transplantation, mice were immunized IP with one million LLC-ova-gp96-Ig. Tumor size was measured with a caliper in 2 dimensions. N=5 in each group, representative of 3 experiments. BCDM indicates B-cell deficient mice; gp, glycoprotein; Ig, immunoglobulin; LLC; Lewis lung carcinoma; PBS, phosphate-buffered saline.

Anti-Tumor Effect by Heat Shock Protein gp96 Vaccination is Enhances in the Absence of B Cells Increased Anti Tumor Activity of Gp96 in the Absence of B Cells:

Immunological tumor rejection usually is dependent on the generation of cytotoxic CD8 cells during a Th1 biased anti tumor immune response. Tumor evasion strategies frequently include immune deviation towards Th2 biased humoral responses including production of Th2 cytokines. Since Th2 responses are associated with B cell activation and with feed back inhibition of TH1 polarization, we tested whether anti tumor immune responses to gp96 are affected by the absence of B cells. As tumor system we used LLC-ova, a spontaneous transplantable lung carcinoma transfected with ovalbumin as surrogate antigen. LLC-ova is non-immunogenic, fast growing (16 h division time) and lethal within about four weeks. LLC-ova was further transfected with gp96-Ig to produce LLC-ova-gp96-Ig, a tumor secreting gp96-Ig at a rate of Song by 1 million cells in 24 hours. LLC-gp96-Ig mediates strong cognate CD8-CTL activation and generates anti tumor immunity. This immunization model was used to evaluate the effect of the absence of B cells on anti tumor responses. LLC-ova was transplanted subcutaneously in the flank in w.t. and B cell deficient (pMT) mice and allowed to establish for 7 days after which period (day 0) 1 million live LLC-ova-gp96-Ig cells were injected i.p. TCR transgenic OT-I cells detecting the ovalbumin derived peptide SIINFEKL presented by ICb were given i.v. ($10^6$ cells) two days before immunization with LLC-gp96-Ig. LLC-ova in w.t. mice growth progressively in the absence of immunization even when OT-I are present (FIG. 16). One intraperitoneal injection of one million LLC-ova-gp96-Ig cells retards tumor growth but is not able to mediate complete tumor rejection. In B cell deficient mice LLC-ova also forms progressive tumors in all mice but tumor progression is slower than in wild type mice. Immunization of B cell deficient mice bearing 7 day established tumors with gp96-secreting LLC-ova leads to complete tumor rejection. Tumors did not recur during the 6 weeks follow up period.

Clearly B deficient mice in this model tumor system are able to mount a tumor rejection response upon gp96-immunization in the presence of an elevated frequency of tumor specific precursor CTL (OT-I). Tumor rejection was dependent on both components since in the absence of adoptively transferred OT-I the anti tumor response to LLC-ova-gp96-Ig was significantly diminished (FIG. 17B). Similarly OT-I alone could not reject LLC-ova without immunization (FIG. 17A). Reconstitution of B cells in B cell deficient mice by transfer of w.t. B cells abolished the ability of gp96 to reject established tumors (FIG. 17C). Clearly the absence of normal B cells is responsible for the enhanced tumor rejection response in B deficient mice.

Enhanced CD8 CTL Clonal Expansion in B Deficient Mice:

The increased ability of gp96-based immunization to reject established LLC-ova tumors in B deficient mice suggested increased CD8 CTL activation. Using gfp-marked OT-I cells we compared the clonal expansion of OT-I cells after immunization of B deficient and w.t. mice. OT-I cells were adoptively transferred i.v. and after a two day equilibration period the mice were injected with LLC-ova-gp96-Ig. The frequency of gfp-OT-I was determined in the peritoneal cavity and in draining mesenteric and para-aortal lymph nodes on day 5, 7 and 12 after immunization. There are essentially no OT-I in the peritoneal cavity prior to immunization and their frequency in draining lymph nodes is 0.5% in the CD8 gate. As reported previously tumor secreted gp96 mediates strong CD8 CTL expansion in w.t. mice which is maximal on day 5. LLC-ova not secreting gp96-Ig does not expand OT-I. Expansion is followed by contraction during the next week (FIG. 15). In B deficient mice CD8 CTL expansion is consistently increased to approximately twice the number seen in w.t. mice.

Reconstitution of B deficient mice with w.t. B cells results in CD8 responses that are phenotypically indistinguishable from w.t. mice. Intraperitoneal immunization with gp96-secreting tumor cells results in the recruitment of large numbers of immune cells including B cells, dendritic cells and NK cells. In w.t. mice B cell accumulation coincides kinetically with CD8 CTL expansion, both taking place maximally between day 3 to 5. DC and NK cells are recruited into the peritoneal cavity during the first 48 hours after gp96-Ig immunization. In the absence of B cells the recruitment of DC and NK cells increased, while reconstitution of B cell deficient mice with w.t. B cells restored w.t. level recruitment of DC and NK cells.

Purification and Adoptive Transfer of OT-I Cells and CD19+ B Cells:

Pooled single cell suspension of splenocytes and lymph node cells were obtained from gfp-OT-I mice and were depleted of red blood cells by ammonium chloride lysis. Gfp-OT-I cells were sorted by positive column selection using anti-CD8a magnetic microbeads and a MACS (Miltenyi Biotec, Auburn, Calif.) according to manufacture's instructions. The purity of isolated OT-I cells was more than 95% of CD8 positive, as determined by flow cytometric analysis. Va2 and VP5.1.2 expressions on purified cells were quantified by flow cytometry before injection. For purification of B cells, CD19+ cells were purified under the same procedures with anti-CD19 microbeads. To reconstitute B cells in pMT mice, 10' purified cells were adoptively transferred through tail veins 2 days before inoculation of LLC-ova cells.

Tumor Inoculation and Treatment Protocol:

Non-irradiated LLC or LLC-ova cells were injected s.c. in 200 pl PBS into the flanks of mice. Five days after the inoculation of LLC-ova cells (day 5), $10^6$ purified OT-I were injected through tail veins in a volume of 0.3 ml PBS. On day 7, mice were immunized with i.p. injection of non-irradiated lo6 LLC-ova-gp96-Ig cells in a volume of 0.5 ml PBS. As non-treatment control, mice were treated with PBS on day 5 and 7. The size of tumors was measured in two dimensions twice per week for at least 20 days. To address OT-I expansion, mice were immunized with i.p. injection of 4×10~ non-irradiated EG7-gp96-Ig cells, after adoptively transfer of $10^6$ gfp-OT-I. To assess the tumor growth in RituximabR-treated human CD20 transgenic mice, mice were treated with i.p injection of 1 mg RituximabR in 0.5 ml PBS or PBS alone on day 4. Except for the Rituximabn treatment, experimental details were as under the same protocol mentioned above.

Flow Cytometric Analysis:

After timed intervals, cells were harvested from mesenteric and para-aorta lymph nodes (dLN) and peritoneal cavity at the indicated times. To examine the depletion of B cells expressing human CD20 after Rituximab® treatment, peripheral blood cells were obtained a week after injection. Red blood cells were removed from samples by ammonium chloride lysis. First, one million cells were incubated for 10 min at 4° C. with anti-CD16132 mAb in PBS containing 0.5% BSA (PBA) to block FcR binding. Thereafter, cells were incubated in the indicated antibodies for 30 min. Samples were analyzed on a FACScan (Becton Dickinson) with CELL Quest software (BD Bioscience). Total number of the indicated immune cells per each tissue was calculated from the percentage of targeted cells and total number of cells in each tissue. Statistical Analysis Significant difference in tumor growth was evaluated by a repeated ANOVA test Values of $p<0.05$ were considered to indicate statistical significance.

What is claimed is:

1. A method of reducing the growth rate of an established cancerous tumor in a subject, the method comprising the step of administering to the subject a vaccine comprising cancer cells secreting gp96, wherein the cancer cells: (i) have been transfected with a vector comprising a nucleic acid encoding a secreted form of gp96 which lacks a KDEL endoplasmic reticulum retention sequence, (ii) are of the same type as the established tumor, and (iii) are a source of tumor-specific peptides that are also expressed by the established tumor; and
wherein the vaccine is administered to the subject multiple times at least once every 3 to 4 days until the growth rate of the established tumor has been reduced.

2. The method of claim 1, wherein the vaccine is administered to the subject once daily.

3. The method of claim 1, wherein the vaccine is administered to the subject twice daily.

4. The method of claim 1, wherein the vaccine is administered to the subject thrice daily.

5. The method of claim 1, wherein the subject has been treated with an agent that depletes B cells.

6. The method of claim 1, further comprising administering to the subject an adjuvant, wherein the adjuvant is bacille Calmette-Guérin (BCG).

7. The method of claim 6, wherein the subject is administered the vaccine and the adjuvant over a period of at least 6 weeks.

8. The method of claim 6, wherein the cells are allogeneic to the subject.

9. The method of claim 6, wherein the cancer is bladder cancer.

10. The method of claim 1, wherein the subject is administered the vaccine over a period of at least 6 weeks.

11. The method of claim 1, wherein the cells are allogeneic to the subject.

12. The method of claim 1, wherein the cancer is bladder cancer.

* * * * *